(12) United States Patent
Lynn et al.

(10) Patent No.: US 11,874,286 B1
(45) Date of Patent: *Jan. 16, 2024

(54) SYSTEM AND METHOD FOR TARGET SUBSTANCE IDENTIFICATION

(71) Applicant: Hound Labs, Inc., Oakland, CA (US)

(72) Inventors: Michael Scott Lynn, Piedmont, CA (US); Hamilton Roger Tang, Los Altos, CA (US); Kate L. Bechtel, Pleasant Hill, CA (US); Peter A. Holst, Los Altos, CA (US); Jacob A. Wolf, Oakland, CA (US); Kevin M. Limtao, Milpitas, CA (US)

(73) Assignee: Hound Labs, Inc., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/249,817

(22) Filed: Mar. 15, 2021

Related U.S. Application Data

(63) Continuation of application No. 15/943,123, filed on Apr. 2, 2018, now Pat. No. 10,955,428, which is a continuation of application No. 15/217,264, filed on Jul. 22, 2016, now Pat. No. 9,933,445.

(60) Provisional application No. 62/351,821, filed on Jun. 17, 2016, provisional application No. 62/351,858, filed on Jun. 17, 2016, provisional application No. 62/337,286, filed on May 16, 2016.

(51) Int. Cl.
| | |
|---|---|
| *G01N 33/497* | (2006.01) |
| *G01N 33/94* | (2006.01) |
| *A61B 5/097* | (2006.01) |
| *A61B 5/08* | (2006.01) |
| *A61B 5/00* | (2006.01) |
| *B01L 3/00* | (2006.01) |
| *G01N 21/77* | (2006.01) |

(52) U.S. Cl.
CPC ........... *G01N 33/948* (2013.01); *A61B 5/082* (2013.01); *A61B 5/097* (2013.01); *A61B 5/4845* (2013.01); *B01L 3/502738* (2013.01); *G01N 2021/7786* (2013.01)

(58) Field of Classification Search
CPC ....... A61B 5/097; A61B 5/085; G01N 33/948
See application file for complete search history.

(56) References Cited

U.S. PATENT DOCUMENTS

| | | | |
|---|---|---|---|
| 3,086,833 | A | 4/1963 | Streck |
| 3,393,108 | A | 7/1968 | Jones |
| 3,676,072 | A | 7/1972 | Krivis |
| 4,133,202 | A | 1/1979 | Marple |
| 4,232,667 | A | 11/1980 | Chalon et al. |
| 4,288,344 | A | 9/1981 | Reiss |
| 4,771,005 | A | 9/1988 | Spiro |
| 4,796,475 | A | 1/1989 | Marpel |

(Continued)

FOREIGN PATENT DOCUMENTS

| | | |
|---|---|---|
| EP | 132313 | 9/1991 |
| EP | 2498093 A1 | 9/2012 |

(Continued)

OTHER PUBLICATIONS

U.S. Appl. No. 14/997,405, Office Action dated Jan. 9, 2017.

(Continued)

*Primary Examiner* — P. Kathryn Wright
(74) *Attorney, Agent, or Firm* — Mahamedi IP Law LLP

(57) ABSTRACT

Systems and techniques for detecting a target substance, such as THC, in a breath constituent sample are provided.

14 Claims, 38 Drawing Sheets

(56) References Cited

U.S. PATENT DOCUMENTS

| | | |
|---|---|---|
| 4,926,679 A | 5/1990 | Dewhurst |
| 5,026,027 A | 6/1991 | Hamilton |
| 5,103,857 A | 4/1992 | Kuhn et al. |
| 5,140,993 A | 8/1992 | Opekun, Jr. et al. |
| 5,196,306 A | 3/1993 | Bobrow et al. |
| 5,230,866 A | 7/1993 | Shartle et al. |
| 5,361,771 A | 11/1994 | Craine et al. |
| 5,438,980 A | 8/1995 | Phillips |
| 5,583,001 A | 12/1996 | Bobrow et al. |
| 5,589,346 A | 12/1996 | Kanan et al. |
| 5,731,158 A | 3/1998 | Bobrow et al. |
| 5,922,610 A | 7/1999 | Alving et al. |
| 6,040,191 A | 3/2000 | Grow |
| 6,067,983 A | 5/2000 | Stenzler |
| 6,326,159 B1 | 12/2001 | Ullman et al. |
| 6,460,539 B1 | 10/2002 | Japuntich et al. |
| 6,537,823 B1 | 3/2003 | Smith |
| 6,582,376 B2 | 6/2003 | Baghdassarian |
| 6,605,444 B1 | 8/2003 | Klein et al. |
| 6,727,067 B2 | 4/2004 | Russman et al. |
| 6,780,617 B2 | 8/2004 | Chen |
| 6,964,862 B2 | 11/2005 | Chen |
| 7,059,349 B2 | 6/2006 | Breda |
| 7,337,072 B2 | 2/2008 | Chen |
| 7,364,553 B2 | 4/2008 | Paz et al. |
| 7,547,285 B2 | 6/2009 | Kline |
| 7,718,421 B2 | 5/2010 | Chen et al. |
| 7,799,521 B2 | 9/2010 | Chen |
| 7,833,489 B2 | 11/2010 | Chen |
| 7,935,504 B2 | 5/2011 | Chen |
| 8,148,116 B2 | 4/2012 | Chen |
| 8,237,118 B2 | 8/2012 | Prox et al. |
| 8,586,932 B2 | 11/2013 | Rousso et al. |
| 8,705,029 B2 | 4/2014 | Palmskog et al. |
| 8,707,758 B2 | 4/2014 | Keays |
| 8,936,933 B2 | 1/2015 | Chen et al. |
| 8,955,366 B2 | 2/2015 | Abraham-Fuchs et al. |
| 9,239,323 B2 | 1/2016 | Keays |
| 9,429,564 B2 | 8/2016 | Beck |
| 9,617,582 B2 | 4/2017 | Milton et al. |
| 9,662,652 B2 | 5/2017 | Chen |
| 9,708,599 B2 | 7/2017 | Chen et al. |
| 9,709,581 B1 | 7/2017 | Gordon et al. |
| 9,709,582 B1 | 7/2017 | Gordon et al. |
| 9,726,684 B1 | 8/2017 | Gordon et al. |
| 9,921,234 B1 | 3/2018 | Lynn et al. |
| 9,933,445 B1 | 4/2018 | Lynn et al. |
| 9,945,878 B1 | 4/2018 | Gordon et al. |
| 9,970,950 B1 | 5/2018 | Lynn et al. |
| 9,976,944 B1 | 5/2018 | Olin et al. |
| 10,226,201 B2 | 3/2019 | Ahmad et al. |
| 10,247,742 B1 | 4/2019 | Lynn et al. |
| 10,408,850 B1 | 9/2019 | Gordon et al. |
| 10,443,050 B2 | 10/2019 | Chen et al. |
| 10,557,563 B2 | 2/2020 | Thurau |
| 10,641,783 B2 | 5/2020 | Lynn et al. |
| 10,955,428 B2 | 3/2021 | Lynn et al. |
| 11,026,596 B1 | 6/2021 | Lynn et al. |
| 11,187,711 B1 | 11/2021 | Lynn et al. |
| 11,426,097 B1 | 8/2022 | Lynn et al. |
| 2002/0177232 A1 | 11/2002 | Melker et al. |
| 2003/0153844 A1 | 8/2003 | Smith |
| 2003/0190259 A1 | 10/2003 | Alley |
| 2004/0043479 A1 | 3/2004 | Briscoe et al. |
| 2005/0105077 A1 | 5/2005 | Padmanabhan et al. |
| 2005/0137491 A1 | 6/2005 | Paz et al. |
| 2005/0279181 A1 | 12/2005 | Trakumas et al. |
| 2006/0094123 A1 | 5/2006 | Day et al. |
| 2006/0195040 A1 | 8/2006 | Nason et al. |
| 2006/0257941 A1 | 11/2006 | McDevitt et al. |
| 2007/0031283 A1 | 2/2007 | Davis et al. |
| 2007/0077660 A1 | 4/2007 | Glas |
| 2008/0004542 A1 | 1/2008 | Allen et al. |
| 2008/0038154 A1 | 2/2008 | Longbottom et al. |
| 2008/0045825 A1 | 2/2008 | Melker et al. |
| 2008/0050839 A1 | 2/2008 | Suslick et al. |
| 2009/0017555 A1 | 1/2009 | Jehanli et al. |
| 2010/0297635 A1 | 11/2010 | Olin et al. |
| 2011/0086364 A1 | 4/2011 | Takkinen et al. |
| 2011/0167932 A1 | 7/2011 | Thornburg et al. |
| 2012/0302907 A1 | 11/2012 | Palmskog et al. |
| 2012/0329142 A1 | 12/2012 | Battrell et al. |
| 2013/0006068 A1 | 1/2013 | Gemer et al. |
| 2013/0011859 A1 | 1/2013 | Putnam et al. |
| 2013/0021153 A1 | 1/2013 | Keays |
| 2013/0102018 A1 | 4/2013 | Schentag et al. |
| 2013/0165806 A1 | 6/2013 | Wondka et al. |
| 2013/0319239 A1 | 12/2013 | Takenaka et al. |
| 2014/0094391 A1 | 4/2014 | McDevitt et al. |
| 2014/0120633 A1 | 5/2014 | Gandini et al. |
| 2014/0276100 A1 | 9/2014 | Satterfield et al. |
| 2014/0288454 A1 | 9/2014 | Paz et al. |
| 2014/0296089 A1 | 10/2014 | Holmes et al. |
| 2014/0311215 A1 | 10/2014 | Keays et al. |
| 2014/0366609 A1 | 12/2014 | Beck et al. |
| 2015/0025407 A1 | 1/2015 | Eichler et al. |
| 2015/0033824 A1 | 2/2015 | Hammarlund et al. |
| 2015/0065901 A1 | 3/2015 | Bhatnagar et al. |
| 2015/0265184 A1 | 9/2015 | Wondka et al. |
| 2015/0305651 A1 | 10/2015 | Attariwala et al. |
| 2015/0313608 A1 | 11/2015 | Baudenbacher et al. |
| 2015/0369830 A1 | 12/2015 | Crichlow |
| 2016/0000358 A1 | 1/2016 | Lundin et al. |
| 2016/0032798 A1 | 2/2016 | Herman et al. |
| 2016/0055359 A1 | 2/2016 | Jensen et al. |
| 2016/0069810 A1 | 3/2016 | Walavalkar et al. |
| 2016/0069919 A1 | 3/2016 | Holmes et al. |
| 2016/0256656 A1 | 9/2016 | Glenn et al. |
| 2016/0299125 A1 | 10/2016 | Cristoni et al. |
| 2017/0023546 A1 | 1/2017 | Holmes et al. |
| 2017/0122851 A1 | 5/2017 | Thatcher et al. |
| 2017/0128692 A1 | 5/2017 | Christopher et al. |
| 2017/0184609 A1 | 6/2017 | Milton et al. |
| 2017/0197213 A1 | 7/2017 | Nielsen et al. |
| 2017/0303822 A1 | 10/2017 | Allsworth et al. |
| 2017/0303823 A1 | 10/2017 | Allsworth et al. |
| 2018/0038798 A1 | 2/2018 | Zhang et al. |
| 2018/0120278 A1 | 5/2018 | Hoorfar et al. |
| 2018/0224471 A1 | 8/2018 | Lynn et al. |
| 2018/0238916 A1 | 8/2018 | Lynn et al. |
| 2018/0243523 A1 | 8/2018 | Nason et al. |
| 2018/0306775 A1 | 10/2018 | Beck et al. |
| 2019/0039069 A1 | 2/2019 | Marshall et al. |
| 2019/0160460 A1 | 5/2019 | Keatch et al. |
| 2020/0124625 A1 | 4/2020 | Dunlop et al. |
| 2020/0147333 A1 | 5/2020 | Stoll et al. |
| 2020/0182892 A1 | 6/2020 | Lynn et al. |
| 2020/0245898 A1 | 8/2020 | Heanue et al. |
| 2020/0245899 A1 | 8/2020 | Heanue et al. |
| 2020/0278275 A1 | 9/2020 | Turgul et al. |
| 2020/0300876 A1 | 9/2020 | Lynn et al. |
| 2020/0397340 A1 | 12/2020 | Dweik |
| 2021/0330516 A1 | 10/2021 | Letourneau et al. |

FOREIGN PATENT DOCUMENTS

| | | |
|---|---|---|
| EP | 2762880 A1 | 8/2014 |
| EP | 2781917 | 9/2014 |
| WO | 9014043 A1 | 11/1990 |
| WO | 2006/083269 | 8/2006 |
| WO | 2011029889 A1 | 3/2011 |
| WO | 2016065300 A1 | 4/2016 |
| WO | 2018076099 A1 | 5/2018 |
| WO | 2018185164 A1 | 10/2018 |
| WO | 2018211280 A1 | 11/2018 |
| WO | 2019011750 A1 | 1/2019 |

OTHER PUBLICATIONS

U.S. Appl. No. 14/997,405, Notice of Allowance dated May 10, 2017.

U.S. Appl. No. 14/997,405, Corrected Notice of Allowability dated Jun. 15, 2017.

(56) References Cited

OTHER PUBLICATIONS

U.S. Appl. No. 15/143,379, Office Action dated Oct. 25, 2016.
U.S. Appl. No. 15/143,379, Notice of Allowance dated Mar. 21, 2017.
U.S. Appl. No. 15/143,379, Notice of Allowability dated Jun. 13, 2017.
U.S. Appl. No. 15/143,328, Office Action dated Sep. 1, 2016.
U.S. Appl. No. 15/143,328, Notice of Allowance dated Feb. 10, 2017.
U.S. Appl. No. 15/143,328, Notice of Allowability dated May 18, 2017.
U.S. Appl. No. 15/143,328, Notice of Allowance dated Jun. 14, 2017.
U.S. Appl. No. 15/650,518, Office Action dated Oct. 4, 2017.
U.S. Appl. No. 15/650,518, Notice of Allowance dated Feb. 1, 2018.
U.S. Appl. No. 14/641,412, Office Action dated May 19, 2016.
U.S. Appl. No. 14/641,412, Final Office Action dated Dec. 5, 2016.
U.S. Appl. No. 14/641,412, Office Action dated Jun. 26, 2017.
U.S. Appl. No. 14/641,412, Notice of Allowance dated Jan. 9, 2018.
U.S. Appl. No. 15/217,151, Office Action dated Jan. 9, 2017.
U.S. Appl. No. 15/217,151, Office Action dated May 16, 2017.
U.S. Appl. No. 15/217,151, Final Office Action dated Oct. 30, 2017.
U.S. Appl. No. 15/217,151, Notice of Allowance dated Dec. 22, 2017.
U.S. Appl. No. 15/217,264, Office Action dated Oct. 24, 2016.
U.S. Appl. No. 15/217,264, Office Action dated Mar. 20, 2017.
U.S. Appl. No. 15/217,264, Final Office Action dated Aug. 16, 2017.
U.S. Appl. No. 15/217,264, Notice of Allowance dated Nov. 16, 2017.
Adams, I.B. et al., "Cannabis: pharmacology and toxicology in animals and humans," Addiction, Nov. 1996;91 (11):1585-614, PubMed abstract 8972919.
Al-Asmari, Ahmed et al., "Method for the quantification of diamorphine and its metabolites in pediatric plasma samples by liquid chromatography—tandem mass spectrometry," Journal of Analytical Toxicology, vol. 34, May 2010.
Atkinson, H.C. et al., "Drugs in human milk. Clinical pharmacokinetic considerations." Clin Pharmacokinet. Apr. 1988;14(4):217-40, PubMed abstract 3292101.
Azorlosa, J.L. et al., "Marijuana smoking: effect of varying delta 9-tetrahydrocannabinol content and number of puffs," J. Pharmacol. Exper. Ther 1992;261:114, abstract.
Bailey, J.R. et al., "Fetal disposition of delta 9-tetrahydrocannabinol (THC) during late pegnancy in the rhesus monkey," Toxicol Appl Pharmacol. Sep. 15, 1987;90(2):315-21, abstract.
Baker, D. et al., "Cannabinoids control spasticity and tremor in a multiple sclerosis model," Nature, Mar. 2, 2000;404(6773):84-7, abstract.
Balabanova, S. et al., "Detection of drugs in sweat," Belt Gerichtl Med. 1990;48:45-9, abstract.
Bashir, W. et al., "Spectrophotometric Determination of Acetone in Acetic Acid", Microchemical Journal, 1983, 28, pp. 77-81.
Beck, Olof et al., "Detection of Delta9-tetrahydrocannabinol in exhaled breath collected from cannabis users," Journal of Analytical Toxicology, vol. 35, Oct. 2011.
Benowitz, Neal L. et al., "Metabolic and psychophysiologic studies of cannabidiol-hexobarbital interaction," Clinical Pharmacology and Therapeutics (1980) 28, 115-120, abstract.
Blanc, Jennifer A. et al., "Adsorption losses from urine-based cannabinoid calibrators during routine use," Clin. Chem. 39/8, 1705-1712 (1993).
Bloom, A.S., Effect of delta9-tetrahydrocannabinol on the synthesis of dopamine and norepinephrine in mouse brain synaptosomes, J Pharmocol Exp Ther. Apr. 1982;221(1):97-103.
Bornheim, Lester M. et al., "Characterization of cytochrome P450 3A inactivation by cannabidiol: possible involvement of cannabidiol-hydroxyquinone as a P450 inactivator," Chem. Res. Toxicol., 1998, 11 (10), pp. 1209-0450.
Bornheim, L.M. et al., "Human hepatic microsomal metabolism of delta 1-tetrahydrocannabinol," Drug Metab Dispos. Mar.-Apr. 1992;20(2):241-6, PubMed abstract 1352216.
Brenneisen, R. et al., "The effect of orally and rectally administered delta 9-tetrahydrocannabinol on spaticity: a pilot study with 2 patients," Int J Clin Pharmocol Ther. Oct. 1996;34(10):446-52.
Brunet, B. et al., "Validation of large white pig as an animal model for the study of cannabinoids metabolism: application to the study of THC distribution in issues," Forensic Sci Int. Sep. 12, 2006;161(2-3):169-74, PubMed abstract 16859848.
Burstein, S. et al., "Isolation and characterization of two major urinary metabolites of 1-tetrahydrocannabinol," Science, Apr. 28, 1972;176(4033):422-3, PubMed abstract 5026162.
Cami, J. et al., "Effect of subject expectancy on the THC intoxication and disposition from smoked hashish cigarettes," Pharmacology Biochemistry and Behavior, vol. 40, Issue 1, Sep. 1991, pp. 115-119.
Challapalli, P.V. et al., "In vitro experiment optimization for measuring tetrahydrocannabinol skin permeation," Int J Pharm. 2002 Jul 25;241(2):329-39, PubMed abstract 12100860.
Chaturvedi, Arvind K., "Postmortem aviation forensic toxicology: an overview," Journal of Analytical Toxicology, vol. 34, May 2010.
"The Chemistry of Phenols," ZVi Rappoport, editor, © 2003 John Wiley & Sons, Ltd. ISBN: 0-471-49737-1.
Chiang, C. Nora et al., "Prenatal drug exposure: kinetics and dynamics," NIDA Research Monograph 60, 1985.
Christophersen, Asbjorg Solberg et al., "Tetrahydrocannabinol stability in whole blood: plastic versus glass containers," Journal of Analytical Toxicology, vol. 10, Jul./Aug. 1986.
Cirimele, V. et al., "Testing human hair for cannabis. III. Rapid screening procedure for the simultaneous identification of delta9-tetrahydrocannabinol, cannabinol, and cannabidiol," Journal of Analytical Toxicology, vol. 20, Jan./Feb. 1996.
Cone, Edward J. et al., "In vivo adulteration: excess fluid ingestion causes false-negative marijuana and cocaine urine test results," Journal of Analytical Toxicology, vol. 22, Oct. 1998.
Cone, Edward J. et al., "Marijuana-laced brownies: behavioral effects, physiologic effects, and urinalysis in humans following ingestion," Journal of Analytical Toxicology, vol. 12, Jul./Aug. 1988.
Cone, Edward J. et al., "Passive inhalation of maiijuana smoke: urinalysis and room air levels of delta-9-tetrahydrocannabinol," Juornal of Analytical Toxicology, vol. 11, May/Jun. 1987.
Crouch, Dennis J. et al., "An evaluation of selected oral fluid point-of-collection drug-testing devices," Journal of Analytical Toxicology, vol. 29, May/Jun. 2005.
Crouch, D.J., "Oral fluid collection: the neglected variable in oral fluid testing," Forensic Sci Int. Jun. 10, 2005;150(2-3):165-73, PubMed abstract 15899565.
Day, David et al., "Detection of THCA in oral fluid by GC-MS-MS," Journal of Analytical Toxicology, vol. 30, Nov./Dec. 2006.
D'Sourza, Deepak Cyril et al., "The psychotomimetic effects of intravenous delta-9-tetrahydrocannabinol in healthy individuals: implications for psychosis," Neuropsychophannacology (2004) 29, 1558-1572.
Ellis, G.M. Jr. et al., "Excretion patterns of cannabiniod metabolites after last use in a group of chronic users," Clin Pharmacol Ther. Nov. 1985;38(5):572-8, PubMed abstract 3902318.
Ellis, George M. Jr. et al. "Excretion patterns of cannabinoid metabilites after last use," 420 Magazine, Oct. 4, 2011, downloaded from https://www.420magazine.com/forums/drug-testing-urine/153724.
ElSohly, M. et al., "Potency trends of Delta9-THC and other cannabinoids in confiscated marijuana from 1980-1997," Journal of Forensic Sciences, vol. 45, No. 1, 2000, pp. 24-30.
Feng, Shixia et al., "Simultaneous analysis of Delta9-THC and its major metabolites in urine, plasma, and meconium by GC-MS using an immunoaffinity extraction procedure," Journal of Analytical Toxicology, vol. 24, Sep. 2000.
Fraser, A.D. et al., "Monitoring urinary excretion of cannabinoids by fluorescence-polarization immunoassay: a cannabiniod-to-creatinine ratio study," Ther Drug Monit. Dec. 2002;24(6):746-50, PubMed abstract 12451292.

(56) References Cited

OTHER PUBLICATIONS

Fraser, A.D. et al., "Urinary excretion profiles of 11-nor9-carboxy-delta9-tetrahydrocannabinol and 11-hydroxy-delta9-THC: cannabinoid metabolites to creatinine ratio study IV," Forensic Sci Int. Jul. 16, 2004;143(2-3):147-52, PubMed abstract 15240035.
Fraser, A.D. et al., "Urinary excretion profiles of 11-nor-9-carboxy-Delta9-tetrahydrocannabinol. Study III. A Delta9-THC-COOH to creatinine ratio study," Forensic Sci Int. Nov. 26, 2003;137(2-3):196-202, PubMed abstract 14609657.
Garrett, E.R. et al., "Pharmacokinetics of delta9-tetrahydrocannabinol in dogs," J Pharm Sci. Mar. 1977;66(3):395-407, PubMed abstract 845807.
Garrett, Edward R. et al., "Physicochemical properties, solubility, and protein binding of Delta9-tetrahydrocannabinol," J Pharm Sci. Jul. 1974;63(7):1056-64, abstract.
Gjerde, Hallvard et al., "Comparison of drug concentrations in blood and oral fluid collected with the Intercept® sampling device," Journal of Analytical Toxicology, vol. 34, May 2010.
Gjerde, H. et al., "Incidence of alcohol and drugs in fatally injured car drivers in Norway," Accid Anal Prev. Aug. 1993;25(4):479-83, PubMed abstract 8357462.
Goodwin, R.S. et al., "Delta(9)-tetrahydrocannabinol, 11-hydroxy-delta(9)-tetrahydrocannabinol and 11-nor-9-carboxy-delta(9)-tetrahydrocannabinol in human plasma after controlled oral administration of cannabinoids," Ther Drug Monit. Aug. 2006;28(4):545-51, PubMed abstract 16885723.
Green, Mitchell D. et al., "Glucuronidation of opioids, carboxylic acid-containing drugs, and hydroxylated xenobiotics catalyzed by expressed monkey UDP-glucuronosyltransferase 2B9 protein," Drug Metabolism and Disposition, vol. 25, No. 12, (1997).
Gross, Stanley J. et al., "Detection of recent cannabis use by saliva Delta9-THC radioimmunoassay," Journal of Analytical Toxicology, vol. 9, Jan./Feb. 1985.
Grotenhermen, F., "Pharmacokinetics and pharmacodynamics of cannabinids," Clin Pharmacokinet. 2003;42(4):327-60, PubMed abstract 12648025.
Gustafson, Richard A. et al., "Urinary cannabinoid detection times after controlled oral administration of Delta9-tetrahydrocannabinol to humans," Clinical Chemistry 49:7, 1114-1124 (2003).
Gustafson, Richard A. et al., "Urinary pharmacokinetics of 11-Nor-9-carboxy-delta9-tetrahydrocannabinol after controlled oral delat9-tetrahydrocannabinol administration," Journal of Analytical Toxicology, vol. 28, Apr. 2004.
Gustafson, R.A. et al., "Validated method for the simultaneous determination of Delta 9-tetrahydrocannabinol (THC), 11-hydroxy-THC and 11-nor-9-carboxy-THC in human plasma using solid phase extraction and gas chromatography—mass spectrometry with positive chemical ionization," J. Chromatogr B Analyt Technol Biomed Life Sci, Dec. 5, 2003;798(1):145-54, PubMed abstract 14630369.
Guy, G.W. et al., "A phase I, double blind, three-way crossover study to assess the pharmacokinetic profile of cannabis based medicine extract (CBME) administered sublingually in variant cannabinoid ratios in normal healthy male volunteers (GWPK0215)," Journal of Cannabis Therapeutics, vol. 3, No. 4, 2003, pp. 121-152.
Hall, B.J. et al., "Determination of cannabinoids in water and human saliva by solid-phase microextraction and quadrupole ion trap gas chromatography/mass spectrometry," Anal chem. May 1, 1998;70(9):1788-96, PubMed abstract 9599579.
Halldin, M.M. et al., "Identification of in vitro metabolites of delta 1-tetrahydrocannabinol formed by human livers," Drug Metab Dispos. Jul.-Aug. 1982;10(4):297-301, PubMed abstract 6126323.
Hampson, A.J. et al., "Cannabidiol and (-)delta9-tetrahydrocannabinol are neuroprotective antioxidants," Proc Natl Acad Sci U.S.A. Jul. 7, 1998; 95(14): 8268-8273.
Hanson, V.W. et al., "Comparison of 3H- and 125I-radioimmunoassay and gas chromatography/mass spectrometry for the determination of delta9-tetrahydrocannabinol and cannabinoids in blood and serum," Journal of Analytical Toxicology, vol. 7, Mar./Apr. 1983.
Harder, S. et al., "Concentration-effect relationship of delta-9-tetrahydrocannabiol and prediction of psychotropic effects after smoking marijuana," Int J Clin Pharmacol Ther. Apr. 1997;35(4):155-9, PubMed abstract 9112136.
Harvey, D.J. et al., "Metabolites of cannabidiol identified in human urine," Xenobiotic, Mar. 1990;20(3):303-20, PubMed abstract 2336840.
Hawks, Richard L., "The Analysis of Cannabinoids in Biological Fluids," NIDA Research Monograph 42, 1982.
Hazekamp, Arno et al., "Cannabis; extracting the medicine," thesis/dissertation 2007.
"Information for health care professionals: cannabis (marihuana, marijuana) and the cannabinoids," Health Canada, Feb. 2013.
Heishman, Stephen J. et al., "Effects of tetrahydrocannabinol content on marijuana smoking behavior, subjective reports, and performance," Pharmacology Biochemistry and Behavior, vol. 34, Issue 1, Sep. 1989, pp. 173-179, abstract.
Himes, Sarah K. et al., "Cannabinoids in exhaled breath following controlled administration of smoked cannabis," Clinical chemistry 59:12 1780-1789 (2013).
Huang, Wei et al., "Simultaneous determination of delta9-tetrahydrocannabinol and 11-nor-9-carboxy-delta9-tetrahydrocannabinol in human plasma by solid-phase extraction and gas chromatography—negative ion chemical ionization-mass spectrometry," Journal of Analytical Toxicology, vol. 25, Oct. 2001.
Huestis, Marilyn A. et al., "Blood cannabinoids. I. Absorption of THC and formation of 11-OH-THC and THCCOOH during and after smoking marijuana," Journal of Analytical Toxicology, vol. 16, Sep./Oct. 1992.
Huestis, Marilyn A. et al., "Blood cannabinoids. II. Models for the prediction of time of marijuana exposure from plasma concentraitons of delta9-tetrahydrocannabinol (THC) and 11-nor-9-carboxy-delta9-tetrahydrocannabinol (THCCOOH)," Journal of Analytical Toxicology, vol. 16, Sep./Oct. 1992.
Huestis, Marilyn A. et al., "Cannabinoid concentrations in hair from documented cannabis users," Forensic Sci Int. Jul. 4, 2007; 169(2-3): 129-136.
Huestis, Marilyn A. et al., "Alternative testing matrices," chapter 11 of the Drug Abuse Handbook, 1998 CRC Press LLC, ISBN 0-8493-2637-0.
Huestis, M.A. et al., "Characterization of the absorption phase of marijuana smoking," Clin Pharmacol Ther. Jul. 1992;52(1):31-41, PubMed abstract 1320536.
Huestis, Marilyn A. et al., "Detection times of marijuana metabolites in urine by immunoassay and GC-MS," Journal of Analytical Toxicology, vol. 19, Oct. 1995.
Huestis, Marilyn A. et al., "Differentiating new marijuana use from residual drug excretion in occasional marijuana users," Journal of Analytical Toxicology, vol. 22, Oct. 1998.
Huestis, Marilyn A. et al., "Estimating the time of last cannabis use from plasma delta9-tetrahydrocannabinol and 11-nor-9-carboxy-delta9-tetrahydrocannabinol concentrations," Clinical Chemistry 51:12 2289-2295 (2005).
Huestis, Marilyn A., "Human cannabinoid pharmacokinetics," Chem Biodivers. Aug. 2007; 4(8): 1770-1804.
Huestis, Marilyn A. et al., "Relationship of delta9-tetrahydrocannabinol concentrations in oral fluid and plasma after controlled administration of smoked cannabis," Journal of Analytical Toxicology, vol. 28, Sep. 2004.
Huestis, Marilyn A. et al., "Urinary excretion profiles of 11-nor-9-carboxy-delta9-tetrahydrocannabinol in humans after single smoked doses of marijuana," Journal of Analytical Toxicology, vol. 20, Oct. 1996.
Hunt, C.A. et al., "Evidence that cannabidiol does not significantly alter the pharmacokinetics of tetrahydrocannabinol in man," J Pharmacokinet Biopharm. Jun. 1981;9(3):245-60, PubMed abstract 6270295.
Hunt, C.A. et al., "Tolerance and disposition of tetrahydrocannabinol in man," J Pharmacol Exp Ther. Oct. 1980;215(1):35-44, PubMed abstract 6256518.
Iribame, C. et al., "Involvement of cytochrome P450 3A4 enzyme in the N-demethylation of methadone in human liver microsomes," Chem Res Toxicol. Mar. 1996;9(2):365-73, PubMed abstract 8839037.

(56) References Cited

OTHER PUBLICATIONS

Jehanli, A. et al., "Blind trials of an onsite saliva drug test for maiijuana and opiates," J Forensic Sci. Sep. 2001;46(5):1214-20, PubMed 11569567.

Joern, William A., "Surface adsorption of the urinary marijuana carboxy metabolite: the problem and a partial solution," Letter to the Editor, Journal of Analytical Toxicology, vol. 16, Nov./Dec. 1992.

Johansson, E. et al., "Determination of delta 1-tetrahydrocannabinol in human fat biopsies from marihuana users by gas chromatography—mass spectrometry," Biomed Chromatogr. Jan. 1989;3(1):35-8, PubMed abstract 2539872.

Johansson, E. et al., "Prolonged apparent half-life of delta 1-tetrahydrocannabinol in plasma of chronic marijuana users," J Pharm Pharmacol. May 1988;40(5):374-5, PubMed abstract 2899638.

Johannson, E. et al., "Terminal elimination plasma half-life of delta 1-tetrahydrocannabinol (delta 1-THC) in heavy users of maiijuana," Eur J Clin Pharmacol. 1989;37(3):273-7, PubMed abstract 2558889.

Johansson, Eva et al., "Urinary excretion half-life of deltal-tetrahydrocannabinol-7-oic acid in heavy marijuana users after smoking," Journal of Analytical Toxicology, vol. 13, Jul./Aug. 1989.

Kadehijian, Leo, "Syva has been a leading developer and manufacturer of drugs-of-abuse tests for more than 30 years," Cannabinoid Issues: Passive inhalation, excretion patterns, and retention times, test result interpretation, Siemens Healthcare Diagnostics Inc., 2009.

Kelly, Peggy et al., "Metabolism of tetrahydrocannabinol in frequent and infrequent marijuana users," Journal of Analytical Toxicology, vol. 16, Jul./Aug. 1992.

Kemp, Philip M. et al., "Cannabinoids in Humans. II. The influence of three methods of hydrolysis on the concentration of THC and two metabolites in urine," Journal of Analytical Toxicology, vol. 19, Sep. 1995.

Kemp, Philip M. et al., "Cannabinoids in Humans. I. Analysis of delta9-tetrahydrocannabinol and six metabolites in plasma and urine using GC-MS," Journal of Analytical Toxicology, vol. 19, Sep. 1995.

Kidwell, David A. et al., "Testing for drugs of abuse in saliva and sweat," Journal of Chromatography B: Biomedical Sciences and Applications, vol. 713, Issue 1, Aug. 21, 1998, pp. 111-135, abstract.

Kintz, Pascal et al., "Detection of cannabis in oral fluid (saliva) and forehead wipes (sweat) from impaired drivers," Journal of Analytical Toxicology, vol. 24, Oct. 2000.

Kintz, Pascal et al., "Sweat testing for heroin and metabolites in a heroin maintenance program," Clinical Chemistry 43:5, 736-739 (1997).

Kintz, P. et al., "Testing human hair for cannabis. II. Identification of TCD-COOH by GC-MS-NCI as a unique proof," J Forensic Sci. Jul. 1995;40(4):619-22, PubMed abstract 7595299.

Kovatsi, Leda et al., "Development and validation of a high-performance liquid chromatography method for the evaluation of niflumic acid cross-reactivity of two commercial immunoassays for cannabinoids in urine," Journal of Analytical Toxicology, vol. 34, May 2010.

Kreuz, D.S. et al., "Delta-9-tetrahydrocannabinol: localization in body fat," Science, Jan. 26, 1973;179(4071):391-3, PubMed abstract 4682965.

Krishna, D.R. et al., "Extrahepatic metabolism of drugs in humans," Clin. Pharmacokinet. Feb. 1994;26(2):144-60, PubMed abstract 8162658.

Lafolie, P. et al., "Importance of creatinine analyses of urine when screening for abused drugs," Clin. Chem. 37/11, 1927-1931 (1991).

Laloup, M. et al., "Correlation of delta9-tetrahydrocannabinol concentrations determined by LC-MS-MS in oral fluid and plasma from impaired drivers and evaluation of the on-site Drager Drug Test," Forensic Sci Int. Sep. 12, 2006;161(2-3):175-9, PubMed abstract 16842950.

Law, B. et al., "Forensic aspects of the metabolism and excretion of cannabinoids following oral ingestion of cannabis resin," J Pharm Pharmacol. May 1984;36(5):289-94, PubMed abstract 6145762.

Lee, Sooyeun et al., "Estimation of the measurement uncertainty by the bottom-up approach for the determination of methamphetamine and amphetamine in urine," Journal of Analytical Toxicology, vol. 34, May 2010.

Lemberger, L. et al., "11-hydroxy-9-tetrahydrocannabinol: pharmacology, disposition, and metabolism of a major metabolite of marihuana in man," Science. Jul. 7, 1972;177(4043):62-4, PubMed abstract 5041775.

Lemberger, L. et al., "Delta-9-tetrahydrocannabinol: metabolism and disposition in long-term marihuana smokers," Science. Jul. 2, 1971;173(3991):72-4, PubMed abstract 5087483.

Lemberger, L. et al., "Marihuana: studies on the disposition and metabolism of delta-9-tetrahydrocannabinol in man," Science. Dec. 18, 1970;170(3964):1320-2, PubMed. abstract 5479011.

Lindgren, J.E. et al., "Clinical effects and plasma levels of delta 9-tetrahydrocannabinol (delta 9-THC) in heavy and light users of cannabis," Psychopharmacology (Berl). 1981;74(3):208-12, PubMed 6267648.

Malfait, A.M. "The nonpsychoactive cannabis constituent cannabidiol is an oral anti-arthritic therapeutic in murine collagen-induced arthritis," Proc Natl Acad Sci USA Aug. 15, 2000;97(17):9561-9566.

Manno, Joseph E. et al., "Temporal indication of marijuana use can be estimated from plasma and urine concentrations of delta9-tetrahydrocannabinol, 11-hydroxy-delta9-tetrahydrocannabinol, and 11-nor-delta9-tetrahydrocannabinol-9-carboxylic acid," Journal of Analytical Toxicology, vol. 25, Oct. 2001.

Manolis, Antony et al., "The detection of delta9-tetrahydrocannabinol in the breath of human subjects," Clinical Biochem. 16,229 (1983).

"Marihuana '84," Proceedings of the Oxford Symposium on Cannabis, D.J. Harvy, editor, IRL Press, Oxford 1984.

Martin, B.R. et al., "3H-delta9-tetrahydrocannabinol distribution in pregnant dogs and their fetuses," Res Commun Chem Pathol Pharmacol. Jul. 1977;17(3):457-70, PubMed abstract 897339.

Mason, A.P. et al., "Cannabis: pharmacology and interpretation of effects," J Forensic Sci. Jul. 1985;30(3):615-31, PubMed abstract 2993473.

Mason, A.P. et al., "Ethanol, marijuana, and other drug use in 600 drivers killed in single-vehicle crashes in North Carolina, 1978-1981," J Forensic Sci. Oct. 1984;29(4):987-1026, PubMed abstract 6502125.

Matsunaga, T. et al., "Metabolism of delta 9-tetrahydrocannabinol by cytochrome P450 isozymes purified from hepatic microsomes of monkeys," Life Sci. 1995;56(23-24):2089-95, PubMed abstract 7776836.

Mattes, R.D. et al., "Bypassing the first-pass effect for the therapeutic use of cannabinoids," Pharmacol Biochem Behav. Mar. 1993;44(3):745-7, PubMed abstract 8383856.

Mattes, R.D. et al., "Cannabinoids and appetite stimulation," Pharmacol Biochem Behav. Sep. 1994;49(1):187-95, PubMed abstract 7816872.

McBurney, L.J. et al., "GC/MS and EMIT analyses for delta9-tetrahydrocannabinol metabolites in plasma and urine of human subjects," Journal of Analytical Toxicology, vol. 10, Mar./Apr. 1986.

Mechoulam, Raphael et al., "Cannabidiol: an overview of some chemical and pharmacological aspects. Part I: chemical aspects," Chemistry and Physics of Lipids 121 (2002) 35-43.

Mechoulam, Raphael, "Plant cannabinoids: a neglected pharmacological treasure trove," Br J Pharmacol. Dec. 2005; 146(7): 913-915.

Meier, H. et al., "Cannabis poisoning after eating salad," Schweiz Med Wochenschr. Feb. 8, 1997;127(6):214-8, PubMed abstract 9157527.

Menkes, D.B. et al., "Salivary THC following cannabis smoking correlates with subjective intoxication and heart rate," Psychopharmacology (Berl). 1991;103(2):277-9, PubMed abstract 1851311.

Mijuriya, Tod H., "Cannabis as a substitute for alcohol: a harm-reduction approach," Journal of Cannabis Therapeutics, vol. 4(1) 2004.

(56) References Cited

OTHER PUBLICATIONS

Milman, Garry et al., "Simultaneous quantification of cannabinoids and metabolites in oral fluid by two-dimensional gas chromatography mass spectrometry," J Chromatogr A. Feb. 26, 2010; 1217(9): 1513-1521.

Moeller, M.R. et al., "Simultaneous quantitation of delta-9-tetrahydrocannabinol (THC) and 11-nor-9-carboxy-delta-9-tetrahydrocannabinol (THC-COOH) in serum by GC/MS using deuterated internal standards and its application to a smoking study and forensic cases," J Forensic Sci. Jul. 1992;37(4):969-83, PubMed abstract 1324293.

Moldoveanu, Serban C. et al., "Differences in the chemical composition of the particulate phase of inhaled and exhaled cigarette mainstream smoke," Contributions to Tobacco Research 22(4), 290 (2007).

Moore, Christine et al., "Analytical procedure for the determination of the marijuana metabolite 11-nor-delta9-tetrahydrocannabinol-9-carboxylic acid in oral fluid specimens," Journal of Analytical Toxicology, vol. 30, Sep. 2006.

Moore, Christine et al., "Application of two-dimensional gas chromatography with electron capture chemical ionization mass spectrometry to the detection of 11-nor-delta9-tetrahydrocannabino1-9-carboxylic acid (THC-COOH) in hair," Journal of Analytical Toxicology, vol. 30, Apr. 2006.

Moore, Christine et al., "Detection of the marijuana metabolite 11-nor-delta9-tetrahydrocannabino1-9-carboxylic acid in oral fluid specimens and its contribution to positive results in screening assays," Journal of Analytical Toxicology, vol. 30, Sep. 2006.

Moore, Christine et al., "The determination of 11-nor-delta9-tetrahydrocannabino1-9-carboxylic acid (THC-COOH) in hair using negative ion gas chromatography-mass spectrometry and high-volume injection," Journal of Analytical Toxicology, vol. 25, Oct. 2001.

Morland, J. et al., "Cannabinoids in blood and urine after passive inhalation of cannabis smoke," J Forensic Sci. Oct. 1985;30(4):997-1002, PubMed abstract 2999292.

Mule, S.J. et al., "Active and realistic passive marijuana exposure tested by three immunoassays and GC/MS in urine," Journal of Analytical Toxicology, vol. 12, May/Jun. 1988.

Mura, P. et al., "Evaluation of six rapid tests for screening of cannabis in sweat, saliva and tears," Acta Clin Belg. 1999;53 Suppl 1:35-8, PubMed abstract 10216980.

Mura, P. et al., "THC can be detected in brain while absent in blood," Letter to the Editor, Journal of Analytical Toxicology, vol. 29, Nov./Dec. 2005.

Nadulski T. et al., "Randomized, double-blind, placebo-controlled study about the effects of cannabidiol (CBD) on the pharmacokinetics of Delat9-tetrahydrocannabinol (THC) after oral application of THC verses standardized cannabis extract," Ther Drug Monit. Dec. 2005;27(6):799-810.

Nadulski T. et al., "Simultaneous and sensitive analysis of THC, 11-OH-THC, THC-COOH, CBD, and CBN by GC-MS in plasma after oral application of small doses of THC and cannabis extract," Journal of Analytical Toxicology, vol. 29, Nov./Dec. 2005.

Nahas, Gabriel G. et al., "Pharmacokinetics of THC in brain and testis, male gametotoxicity and premature apoptosis of spermatozoa," Human Psycopharmacology: Clinical and Experimental, vol. 17, Issue 2, pp. 103-113, Mar. 2002, abstract.

Niedbala, R. Sam et al., "Detection of marijuana use by oral fluid and urine analysis following single-dose administration of smoked and oral marijuana," Journal of Analytical Toxicology, vol. 25, Jul./Aug. 2001.

Niedbala, R. Sam et al., "Passive cannabis smoke exposure and oral fluid testing. II. Two studies of extreme cannabis smoke exposure in a motor vehicle," Journal of Analytical Toxicology, vol. 29, Oct. 2005.

Ohlsson, A. et al., "Plasma delta-9 tetrahydrocannabinol concentrations and clinical effects after oral and intravenous administration and smoking," Clin Pharmacol Ther. Sep. 1980;28(3):409-16, PubMed abstract 6250760.

Ohlsson, Agneta et al., "Single dose kinetics of deuterium labelled deltal-tetrahydrocnnabinol in heavy and light cannabis users," Biological Mass Spectrometry, vol. 9, Issue 1, pp. 6-10, Jan. 1982, abstract.

Owens, S. Michael et al., I Radioimmunoassay of delta-9-tetrahydrocannabinol in blood and plasma with a solid-phase second-antibody separation method, Clin. Chem. 27/4, 619-624 (1981).

Peel, H.W. et al., "Detection of drugs in saliva of impaired drivers," J Forensic Sci. Jan. 1984;29(1):185-9, PubMed abstract 6366113.

Perez-Reyes, M. et al., "The clinical pharmacology and dynamics of marihuana cigarette smoking," J Clin Pharmacol. Aug.-Sep. 1981;21(8-9 Suppl):2015-2075, PubMed abstract 6271825.

Perez-Reyes, M. et al., "Comparison of effects of marihuana cigarettes to three different potencies," Clin Pharmacol Ther. May 1982;31(5):617-24, PubMed abstract 6280918.

Perez-Reyes, M. et al., "Intravenous injection in man of 9-tetrahydrocannabinol and 11-OH-9-tetrahydrocannabinol," Science. Aug. 18, 1972;177(4049):633-5, PubMed abstract 4558903.

Piao, Wen et al., "Development of azo-based fluorescent probes to detect different levels of hypoxia," Angew. Chem. Int. Ed. 2013, 52, 13028-13032.

Quintela, Oscar et al., "Recovery of drugs of abuse from the immunalysis quantisal™ oral fluid collection device," Journal of Analytical Toxicology, vol. 30, Oct. 2006.

Rahim S.A. et al., "Colorimetric determination of ethanol in the presence of methanol and other species in aqueous solution," Talanta. Nov. 1992;39(11):1489-91, PubMed abstract 18965558.

Rohrich, J. et al., "Concentrations of delta9-tetrahydrocannabinol and 11-nor-9-carboxytetrahydrocannabinol in blood and urine after passive exposure to cannabis smoke in a coffee shop," Journal of Analytical Toxicology, vol. 34, May 2010.

Russo, E. et al., "A tale of two cannabinoids: the therapeutic rational for combining tetrahydrocannabinol and cannabidiol," Med Hypotheses. 2006;66(2):234-46, PubMed abstract 16209908.

Samyn N. et al., "On-site testing of saliva and sweat with Drugwipe and determination of concentrations of drugs of abuse in saliva, plasma and urine of suspected users," Int J Legal Med. 2000;113(3):150-4, PubMed abstract 10876986.

Scheuplein, Robert J., "Mechanism of percutaneous absorption. II. Transient diffusion and the relative importance of various routes of skin penetration," J. Invest. Dermatol 1967;48:79.

Schwartz, Richard H. et al., "Laboratory detection of marijuana use, Experience with a photometric immunoassay to measure urinary cannabinoids," Aj J Dis Child. 1985;139(11):1093-1096, abstract.

Schwilke, Eugene W. et al., "Delta9-tetrahydrocannabinol (THC), 11-hydroxy-THC, and 11-nor-9-carboxy-THC plasma pharmacokinetics during and after continuous high-dose oral THC," Clinical Chemistry 55:12 2180-2189 (2009).

Shaw, Leslie M. et al., "Ultrasensitive measurement of delta-9-tetrahydrocannabinol with a high energy dynode detector and electron-capture negative chemical-ionization mass spectrometry," Clin. Chem. 37/12, 2062-2068 (1991).

Skopp, G. et al., "Partition coefficient, blood to plasma ratio, protein binding and short-term stability of 11-nor-Delta(9)-carboxy tetrahydrocannabinol glucuronide," Forensic Sci Int. Mar. 28, 2002;126(1):17-23, PubMed abstract 11955826.

Soares, J.R. et al., "Significant developments in radioimmune methods applied to delta9-THC and its 9-substituted metabolites," Analysis of Cannabinoids Research Monograph 42, NIDA 1982.

Stinchcomb, A.L. et al., "Human skin permeation of Delta8-tetrahydrocannabinol, cannabidiol and cannbinol," J Pharm Pharmacol. Mar. 2004;56(3):291-7, PubMed abstract 15025853.

Strano-Rossi, Sabina et al., "Analysis of stimulants in oral fluid and urine by gas chromatography—mass spectrometry II: Pseudophedrine," Journal of Analytical Toxicology, vol. 34, May 2010.

Tan, Chongxiao et al., "Direct detection of delta9-tetrahydrocannabinol in aqueous samples using a homogeneous increasing fluorescence immunoassay (HiFi)," Anal Bioaanal Chem, 2010. 8 pgs.

Teshima, N. et al, "Determination of acetone in breath", Analytica Chimica Acta, 2005, 535, pp. 189-199.

Toennes, Stefan W. et al., "Pharmacokinetic properties of delta9-tetrahydrocannabinol in oral fluid of occasional and chronic users," Journal of Analytical Toxicology, vol. 34, May 2010.

(56) References Cited

OTHER PUBLICATIONS

Turner, Carton E. et al., "Constituents of cannabis sativa 1. XVII. A review of the natural constituents," J. Nat. Prod. 1980;43:169.
Valiveti, S. et al., "In vitro/in vivo correlation studies for transdermal delta 8-THC development," J Pharm Sci. May 2004;93(5):1154-64, PubMed abstract 15067692.
Van der Kooy, F. et al., "Cannabis smoke condensate I: The effect of different preparation methods on tetrahydrocannabinol levels," Inhalation Toxicology, 20:801804, 2008.
Vinciguerra, V. et al., "Inhalation marijuana as an antiemetic for cancer chemotherapy," NY State J Med. Oct. 1988;88(10):525-7.
Wall, M.E. et al., "The metabolism of delta 9-tetrahydrocannabinol and related cannabinoids in man," J Clin Pharmacol. Aug.-Sep. 1981;21 (8-9 Suppl):178S-189S, PubMed abstract 6271823.
Wall, M.E. et al., "Metabolism, disposition, and kinetics of delta-9-tetrahydrocannabinol in men and women," Clin Pharmacol Ther. Sep. 1983;34(3):352-63, PubMed abstract 6309462.
Walsh, J. Michael et al., "An evaluation of rapid point-of-collection oral fluid drug-testing devices," Journal of Analytical Toxicology, vol. 27, Oct. 2003.
Watanabe, K. et al., "Brain microsomal oxidation of delta 8- and delta 9-tetrahydrocannabinol," Biochem Biophys Res Commun. Nov. 30, 1988;157(1):75-80, PubMed abstract 2848522.
Widman, M. et al., "Metabolism of delta 1-tetrahydrocannabinol by the isolated perfused dog lung. Comparison with in vitro liver matabolism." J Phar Pharmacol. Nov. 1975;27(11):842-8, PubMed abstract 1493.
Williams, P.L. et al., "Identification in human urine of delta 9-tetrahydrocannabinol-11-oic acid glucuronide: a tetrahydrocannabinol metabolite," J Pharm Pharmacol. Jul. 1980;32(7):445-8, PubMed abstract 6105177.
Wingert, William E., "Lowering cutoffs for initial and confirmation testing for cocaine and marijuana: large-scale study of effects on the rates of drug-positive results," Clinical Chemistry 43:1 100-103 (1997).
Zajicek, J. et al., "Cannabinoids for treatment of spasticity and other symptoms related to multiple sclerosis (CAMS study): multicentre randomised placebo-controlled trial," Lancet. Nov. 8, 2003;362(9395):1517-26, abstract.
Zias, Joe et al., "Early medical use of cannabis," Nature; May 20, 1993; 363,6426; Research Library Core p. 215.
Zuardi, A.W. et al., "Action of cannabidiol on the anxiety and other effects produced by delta 9-THC in normal subjects," Psychopharmacology (Berl). 1982;76(3):245-50, PubMed abstract 6285406.
International Search Report dated Jan. 23, 2020, for International Patent Application No. PCT/US2019/060342, 2 pages.
Jokerst JV, Chen Z, Xu L, Nolley R, Chang E, Mitchell B, Brooks JD, Gambhir SS. A magnetic bead-based sensor for the quantification of multiple prostate cancer biomarkers. PloS One. (Sep. 30, 2015), 10(9):e0139484. (15 pages).
Karst, Matthias et al., "Analgesic effect of the synthetic cannabinoid CT-3 on chronic neuropathic pain," JAMA. 2003;290(13):1757-1762.
Klejnowski, K et al. "Number Size Distribution of Ambient Particles in a Typical Urban Site: The First Polish Assessment Based on Long-Term (9 Months) Measurements", The Scientific World Journal, (Oct. 2013), 2013(1):539568.
Kodavanti, U.P. "Respiratory toxicity biomarkers", In Biomarkers in Toxicology, (Jan. 1, 2014) (pp. 217-239). Academic Press.
Krenke, K. et al., "Inflammatory cytokines in exhaled breath condensate in children with inflammatory bowel diseases", Pediatric pulmonology, (Dec. 2014), 49(12):1190-5.
Le Ru EC, Blackie E, Meyer M, Etchegoin PG. Surface enhanced Raman scattering enhancement factors: a comprehensive study. The Journal of Physical Chemistry C. Sep. 20, 2007;111(37):13794-803.
Massachusetts Probation Service, "Probations Plan to Strengthen Drug Testing", Apr. 15, 2016 (Year: 2016).
Oguma, T., et al., "Clinical contributions of exhaled volatile organic compounds in the diagnosis of lung cancer", PloS one, (Apr. 6, 2017), 12(4):e0174802.
Olmon RL, Slovick B, Johnson TW, Shelton D, Oh SH, Boreman GD, Raschke MB. "Optical dielectric function of gold", Physical Review B. Dec. 28, 2012;86(23):235147.
Pardon, G, et al., "Aerosol sampling using an electrostatic precipitator integrated with a microfluidic interface", Sensors and Actuators B: Chemical. Feb. 2015, vol. 212, pp. 344-352.
Perez-Reyes, Mario, "Marijuana smoking: factors that influence the bioavailability of tetrahydrocannabinol," NIDA Monograph 1990,99:42.
PerkinElmer Inc., "TSA Signal Amplification (TSA) Systems," Document No. 007703_01, 16 pages, accessed at berkinelmer.com/lab-solutions/resources/docs/BRO_tsasignalamplification systems.pdf.
Prodromidis, M.I., "Impedimetric immunosensors—A review", Electrochimica Acta, (May 30, 2010), 55(14):4227-33.
Saalberg, Yannick and Marcus Wolff, "VOC breath biomarkers in lung cancer", Clinica Chimica Acta, (Aug. 1, 2016), 459:5-9.
Samitas, K., et al., "Exhaled cysteinyl-leukotrienes and 8-isoprostane in patients with asthma and their relation to clinical severity", Respiratory medicine, (May 1, 2009), 103(5):750-6.
Sarafian, Theodor et al., "Inhaled marijuana smoke disrupts mitochondrial energetics in pulmonary epithelial cells in vivo," Am J Physiol Lung Cell Mol Physiol, 2006, 290.L1202-L1209. (Year:2006).
Sarah Milliken, "Self-assembled vertically aligned Au nanorod arrays for surface-enhanced Raman scattering (SERS) detection of Cannabinol", Jan. 12, 2018 (Year: 2018).
Sean I. Hwang, "Tetrahydrocannabinol Detection Using Semiconductor-Enriched Single-Walled Carbon Nanotube Chemiresistors", 2019 hereafter Hwang (Year: 2019).
Sezin Yuksel, "Trace detection of tetrahydrocannabinol (THC) with a SERS-based capillary platform prepared by the in situ microwave synthesis of AgNPs", May 24, 2016 (Year: 2016).
Sigma, "How Proximity Ligation Assays (PLA) Work".
Sivashanmugan K, Squire K, Tan A, Zhao Y, Kraai JA, Rorrer GL, Wang AX. "Trace detection of tetrahydrocannabinol in body fluid via surface-enhanced Raman scattering and principal component analysis", ACS sensors. Mar. 25, 2019;4(4):1109-17.
Stevenson H, Bacon A, Joseph KM, Gwandaru WR, Bhide A, Sankhala D, Dhamu VN, Prasad S. "A rapid response electrochemical biosensor for detecting THC in saliva", Scientific reports. Sep. 3, 2019; 9(1):1-11. (11 pages) // 9:12701 https://doi.org/10.1038/s41598-019-49185-y.
Stiles PL, Dieringer JA, Shah NC, Van Duyne RP. "Surface-enhanced Raman spectroscopy", Annu. Rev. Anal. Chem . . . Jul. 19, 2008;1:601-26.
Switz, N. A., et al., "Low-Cost Mobile Phone Microscopy with a Reversed Mobile Phone Camera Lens", PloS one, (May 22, 2014), 9(5):e95330. 7 pages.
Townsend, Doug, Ian Eustis, Mark Lewis, Steven Rodgers, Kevin Smith, Ariel Bohman, C. T. Shelton, and C. A. Sacramento. "The Determination of Total THC and CBD Content in Cannabis Flower by Fourier Transform Near Infrared Spectroscopy." (2018); Document No. 014329_01, 5 pages, accessed at perkinelmer.com/lab-solutions/resources/docs/app_determination_of_thc_and_cbd_cannabisflower.pdf.
Ullman EF, Kirakossian H, Switchenko AC, Ishkanian J, Ericson M, Wartchow CA, Pirio M, Pease J, Irvin BR, Singh S, Singh R. "Luminescent oxygen channeling assay (LOCI): sensitive, broadly applicable homogeneous immunoassay method", Clinical chemistry. Sep. 1, 1996;42(9):1518-26.
Vahimaa P et al., "Surface-Enhanced Raman Spectroscopy (SERS)," Institute of Photonics at the University of Eastern Finland, accessible at sway.com/s/XtgAoh8F5QewSEFL/embed.
Wan, G.H., et al., "Cysteinyl leukotriene levels correlate with 8-isoprostane levels in exhaled breath condensates of atopic and healthy children", Pediatric research (Nov. 2013), 74(5):584.
Wang, AX, Kong X. Review of recent progress of plasmonic materials and nano-structures for surface-enhanced Raman scattering. Materials. Jun. 2015;8(6):3024-52.
Wiegand, D.M. et al., "Evaluation of police officers exposure to secondhand cannabis smoke at open-air stadium events", NIOSH health hazard evaluation report ; HHE 2017-0174-335, (Mar. 2019), https://www.cdc.gov/niosh/hhe/reports/pdfs/2017-0174-3335.pdf.

(56) References Cited

OTHER PUBLICATIONS

Written Opinion of the Searching Authority dated Apr. 6, 2020, for International Patent Application No. PCT/US2020/13553, 7 pages.
Written Opinion of the Searching Authority dated Jan. 23, 2020, for International Patent Application No. PCT/US2019/060342, 9 pages.
Yang HU, DArchangel J, Sundheimer ML, Tucker E, Boreman GD, Raschke MB. "Optical dielectric function of silver", Physical Review B. Jun. 22, 2015;91(23):235137.
Zanconato, S., et al., "Leukotrienes and 8-isoprostane in exhaled breath condensate of children with stable and unstable asthma", Journal of Allergy and Clinical Immunology, (Feb. 1, 2004), 113(2):257-63.
Zhou, J., "Review of recent developments in determining volatile organic compounds in exhaled breath as biomarkers for lung cancer diagnosis", Analytica chimica acta, (Dec. 15, 2017), 996:1-9.
Zhu, H.J., Wang JS, Markowitz JS, Donovan JL, Gibson BB, Gefroh HA, DeVane CL., "Characterization of P-glycoprotein inhibition by major cannabinoids from marijuana", Journal of Pharmacology and Experimental Therapeutics. May 1, 2006,317(2):850-7.
"Drug detection, health monitoring etc.", SensAbues AB—Innovation, downloaded on Mar. 25, 2019 from http://sensabues.com/innovation.
"Exhaled breath biological sample matrix. EB", SensAbues AB—Product, downloaded on Mar. 25, 2019 from http://sensabues.com/product.
"Exhaled breath sampling company", SensAbues AB—About, downloaded on Mar. 25, 2019 from http://sensabues.com/about.
"FAIMS Breathalyzer Device", downloaded on Mar. 25, 2019 from https://algernonpharmaceuticals.com/faims-breathalyzer-device/.
"Low cost, non-invasive and non-intrusive", SensAbues AB—Benefits, downloaded on Mar. 25, 2019 from http://sensabues.com/benefits.
"N.S. woman who tested positive for pot when she wasnt high to challenge roadside testing laws," CBC Radio, posted Apr. 3, 2019. 6 pages.
"Owlstone—About", downloaded on Mar. 25, 2019 from https://www.owlstonemedical.com/about/.
"Owlstone—EVOC Probes", downloaded on Mar. 25, 2019 from https://www.owlstonemedical.com/science-technology/evoc-probes/.
"Owlstone—FAIMS technology", downloaded on Mar. 25, 2019 from https://www.owlstonemedical.com/science-technology/faims-technology/.
"Owlstone—Research case studies", downloaded on Mar. 25, 2019 from https://www.owlstonemedical.com/science-technology/research-case-studies/.
"Owlstone Medical—Active Clinical Pipeline", downloaded on Mar. 25, 2019 from https://www.owlstonemedical.com/clinical-pipeline/.
"Owlstone Medical—Products", downloaded on Mar. 21, 2019 from https://www.owlstonemedical.com/products/.
"Owlstone Medical—The Home of Breath Biopsy: A Breathalyzer for Disease", downloaded on Mar. 25, 2019 from https://www.owlstonemedical.com/#.
"Owlstone Medical—The Home of Breath Biopsy: Breath Biopsy—VOC Biomarkers", downloaded on Mar. 25, 2019 from https://www.owlstonemedical.com/#.
"Pexa—About PExA", downloaded on Mar. 25, 2019 from http://pexa.se/en/about-pexa/.
"Pexa—Analysis", downloaded on Mar. 25, 2019 from http://pexa.se/en/product-services/analysis/.
"Pexa—Business Concept Vision", downloaded on Mar. 25, 2019 from http://pexa.se/en/about-pexa/business-concept-vision/.
"Pexa—History", downloaded on Mar. 25, 2019 from http://pexa.se/en/about-pexa/history/.
"Pexa—How PExA works", downloaded on Mar. 25, 2019 from http://pexa.se/en/product-services/how-pexa-works/.
"Pexa—Particles in Exhaled Air", downloaded on Mar. 25, 2019 from http://pexa.se/en/.

"Pexa—PExA 2.0", downloaded on Mar. 25, 2019 from http://pexa.se/en/product-services/pexa-2-0/.
"Pexa—Product Services", downloaded on Mar. 25, 2019 from http://pexa.se/en/product-services/.
"Pexa—Product-Sheet", Sep. 2016.
"Pexa—Research & Development", downloaded on Mar. 25, 2019 from http://pexa.se/en/product-services/research-development/.
"Pexa—Research areas", downloaded on Mar. 25, 2019 from http://pexa.se/en/respiratory-research/research-areas/.
"Pexa—Respiratory Research Needs", downloaded on Mar. 25, 2019 from http://pexa.se/en/respiratory-research/.
"Pexa—The importance of early diagnosis", downloaded on Mar. 25, 2019 from http://pexa.se/en/respiratory-research/the-importance-of-early-diagnosis/.
"Pexa—The search for new biomarkers", downloaded on Mar. 25, 2019 from http://pexa.se/en/respiratory-research/the-search-for-new-biomarkers/.
"SensAbues AB—Next generation drug detection and health monitoring", SensAbues AB—Home, downloaded on Mar. 25, 2019 from http://sensabues.com/home.
"Volatile Organic Compounds (VOC) as non-invasive biomarkers for a range of diseases", downloaded on Mar. 25, 2019 from https://www.owlstonemedical.com/science-technology/voc-biomarkers/.
Alexander, Brentan R., "Design of a microbreather for two-phase microchannel devices", Dissertation submitted to Massachusetts Institute of Technology. Dept. of Mechanical Engineering, (Jun. 2008), 59 pages.
Aliberti, S, et al., "Serum and exhaled breath condensate inflammatory cytokines in community-acquired pneumonia: a prospective cohort study", Pneumonia (Nathan), (Jun. 23, 2016), 8:8. doi: 10.1186/s41479-016-0009-7. eCollection 2016.
Andrews, Travis M., "Breathalyzers of the Future Today," The Atlantic, Jun. 27, 2013. Downloaded from the Internet on Feb. 4, 2019, http://www.theatlantic.com/health/archive/2013/06/breathalyzers-of-the-future-today/277249/.
Bajaj, P., and F.T. Ishmael, "Exhaled breath condensates as a source for biomarkers for characterization of inflammatory lung diseases", Journal of Analytical Sciences, Methods and Instrumentation, (Mar. 20, 2013), 3(01):17.
Beaudet L, Rodriguez-Suarez R, Venne MH, Caron M, Bedard J, Brechler V, Parent S, Bielefeld-Sevigny M. "AlphaLISA immunoassays: the no-wash alternative to ELISAs for research and drug discovery", Nature Methods, (Dec. 2008), 5(12):an8-9.
Beck, O., et al., "Detection of drugs of abuse in exhaled breath using a device for rapid collection: comparison with plasma, urine and self-reporting in 47 drug users" Journal of breath research, (Apr. 25, 2013), 7(2):026006.
Carpenter, C.T., Price PV, Christman BW. Exhaled breath condensate isoprostanes are elevated in patients with acute lung injury or ARDS. Chest. Dec. 1, 1998;114(6):1653-9.
Cecinato, A., Balducci C, Perilli M., "Illicit psychotropic substances in the air: The state-of-art", Sci Total Environ, (Jan. 1, 2016), 539:1-6. doi: 10.1016/j.scitotenv.2015.08.051. Epub Sep. 8, 2015. PMID: 26360454.
Chuah K, Wu Y, Vivekchand SR, Gaus K, Reece PJ, Micolich AP, Gooding JJ. "Nanopore blockade sensors for ultrasensitive detection of proteins in complex biological samples", Nature communications, (May 8, 2019), 10(1):1-9. (9 pages).
Coucke et al., "Tetrahydrocannabinol concentrations in exhaled breath and physiological effects following cannabis intake—A pilot study using illicit cannabis", Clinical Biochemistry, 2016, pp. 1072-1077.
D'Ambrosio, M. et al., "Point-of-care quantification of blood-borne filarial parasites with a mobile phone microscope", Science Translational Medicine (May 6, 2015), vol. 7, Issue 286, pp. 286re4. 10 pages.
Doran, GS, Deans R, De Filippis C, Kostakis C, Howitt JA., "Work place drug testing of police officers after THC exposure during large volume cannabis seizures", Forensic Sci Int. (Jun. 2017), 275:224-233. doi: 10.1016/j.forsciint.2017.03.023. Epub Apr. 2, 2017. PMID: 28412574.

(56) References Cited

OTHER PUBLICATIONS

Dunk, et al., "Development of a Portable Marijuana Breathalyzer", (Mar. 2018), URL=http://https://houndlabs.com/wp-content/uploads/2018/03/Hound-TRT-Pittcon-Poster.pdf.

Emelyanov, A., et al., "Elevated concentrations of exhaled hydrogen peroxide in asthmatic patients", Chest, (Oct. 1, 2001), 120(4):1136-9.

Gramse G, Dols-Perez A, Edwards MA, Fumagalli L, Gomila G. Nanoscale measurement of the dielectric constant of supported lipid bilayers in aqueous solutions with electrostatic force microscopy. Biophysical journal. Mar. 19, 2013;104(6):1257-62.

Grob NM, Aytekin M, Dweik RA. "Biomarkers in exhaled breath condensate: a review of collection, processing and analysis", Journal of breath research, (Sep. 8, 2008), 2(3):037004.

Hasan, R.A., et al., "Lipoxin A4 and 8-isoprostane in the exhaled breath condensate of children hospitalized for status asthmaticus", Pediatric critical care medicine: a journal of the Society of Critical Care Medicine and the World Federation of Pediatric Intensive and Critical Care Societies, (Mar. 2012), 13(2):141.

International Preliminary Report on Patentability dated Jul. 27, 2021, for International Patent Application No. PCT/US2020/13553, 8 pages.

International Preliminary Report on Patentability dated May 11, 2021, for International Patent Application No. PCT/US2019/060342, 9 pages.

International Search Report dated Apr. 6, 2020, for International Patent Application No. PCT/US2020/13553, 2 pages.

SYSTEM AND METHOD FOR TARGET SUBSTANCE IDENTIFICATION

CROSS REFERENCE TO RELATED APPLICATIONS

This application is a continuation of U.S. patent application Ser. No. 15/943,123, filed on Apr. 2, 2018, and titled "SYSTEM AND METHOD FOR TARGET SUBSTANCE IDENTIFICATION," which issued on Mar. 23, 2021, as U.S. Pat. No. 10,955,428 and which is a continuation of U.S. patent application Ser. No. 15/217,264, filed on Jul. 22, 2016, and titled "SYSTEM AND METHOD FOR TARGET SUBSTANCE IDENTIFICATION," which issued as U.S. Pat. No. 9,933,445, on Apr. 3, 2018, which itself claims benefit of priority under 35 U.S.C. § 119(e) to U.S. Provisional Patent Application No. 62/337,286, filed May 16, 2016, and titled "BREATH COLLECTOR MODULE," U.S. Provisional Patent Application No. 62/351,858, filed Jun. 17, 2016, and titled "COMPOSITIONS AND METHODS FOR DETECTION OF TARGET CONSTITUENT IN EXHALED BREATH," and U.S. Provisional Patent Application No. 62/351,821, filed Jun. 17, 2016, and titled "SYSTEM AND METHOD FOR TARGET SUBSTANCE IDENTIFICATION"; this application is also related to U.S. patent application Ser. No. 15/217,151, filed Jul. 22, 2016, and titled "COMPOSITIONS AND METHODS FOR DETECTION OF TARGET CONSTITUENT IN EXHALED BREATH," which also claims benefit of priority to U.S. Provisional Patent Application No. 62/351,858, filed Jun. 17, 2016; this application is also related to U.S. patent application Ser. No. 14/997,405, titled "METHOD, DEVICE AND SYSTEM FOR TARGET SUBSTANCE DETECTION" and filed Jan. 15, 2016, which claims priority benefit under 35 U.S.C. § 119(e) to U.S. Provisional Application Nos. 62/104,813, filed Jan. 18, 2015, and 62/107,331, filed Jan. 23, 2015, both of which are titled "METHOD, DEVICE AND SYSTEM FOR TARGET SUBSTANCE DETECTION," as well as to U.S. Provisional Application No. 62/277,854, filed Jan. 12, 2016, and titled "PORTABLE, HAND-HELD INSTRUMENT FOR DETECTION AND QUANTIFICATION OF CANNABINOIDS AND ALCOHOL IN EXHALED HUMAN BREATH"; all of these applications are hereby incorporated by reference herein in their entireties.

FIELD OF THE INVENTION

The present disclosure relates generally to analytical measurement devices, and more specifically to devices capable of measuring substances in exhaled human breath.

BACKGROUND

With legalization of marijuana expanding and the risk of marijuana-associated impaired driving increasing, it is anticipated by the present inventors that there will be an increased need for portable and accurate measurement devices for quantifying levels of cannabinoid compounds, such as tetrahydrocannabinol (THC), that are present in a person's breath, e.g., such as during a traffic stop for suspected driving-under-the-influence. THC detection poses significant challenges since the amounts of THC that may be present in an exhaled breath are quite minute—much more so than is the case with alcohol. Furthermore, THC detection in human breath is generally the only reliable way to determine if a suspected marijuana user is under the influence. Unlike with alcohol, which the body can purge in relatively short order, e.g., less than a day, THC compounds may be present in a person's body long after they are no longer under the influence of the THC. Thus, detection of THC via blood or urine sample may result in false positives. Testing for THC in breath at the roadside would be convenient, non-invasive, and leverages the wide acceptance of administering a breath test at the roadside, as is commonly employed for alcohol.

SUMMARY

Details of one or more implementations of the subject matter described in this specification are set forth in the accompanying drawings and the description below. Other features, aspects, and advantages will become apparent from the description, the drawings, and the claims.

In some implementations, a tetrahydrocannabinol (THC) detection system is provided that includes an elution port, a sample reservoir containing a sample solvent, an indicator chamber containing an indicator, a solvent reservoir, a buffer reservoir containing a basic buffer, an optical measurement chamber, and a plurality of valves that are configured to control fluid flow from or to the elution port, the sample reservoir, the indicator chamber, the solvent reservoir, and the optical measurement chamber. The plurality of valves may be arranged such that fluid flow between such components is controllable to permit a breath constituent sample to be conveyed from the elution port to the sample reservoir, permit at least a portion of the basic buffer to be combined with the breath constituent sample, permit at least a first portion of the indicator to be combined with the breath constituent sample to form a sample adduct with any THC that is present in the breath constituent sample, permit at least a first portion of the solvent to be combined with the sample adduct, and permit the combined sample adduct and solvent to be delivered to the optical measurement chamber.

In some implementations, the solvent in the solvent reservoir may be a mixture of methyl tertiary butyl ether and heptane.

In some implementations of the THC detection system, the system may further include a controller having one or more processors and a memory. The one or more processors may be communicatively connected with the memory, and the memory may store computer-executable instructions for controlling the one or more processors to control the plurality of valves to facilitate the conveying of the breath constituent sample from the elution port to the sample reservoir, the combining of the at least a first portion of the indicator with the breath constituent sample to form the sample adduct, the combining of the at least a first portion of the solvent with the sample adduct, and the delivering of the combined sample adduct and solvent to the optical measurement chamber.

In some implementations of the THC detection system, the elution port, the sample reservoir, the indicator chamber, the solvent reservoir, the optical measurement chamber, and the plurality of valves may be located in a common cartridge that is configured to be inserted into an analysis unit having an optical sensor system configured to obtain luminescence readings from the combined sample adduct and solvent from the optical measurement chamber. In some such implementations of the THC detection system, the system may further include an analysis station that is configured to receive the common cartridge, includes the optical sensor system, and includes actuators configured to independently actuate the sample reservoir and the solvent reservoir so as to drive fluids into and out of the sample reservoir and the solvent reservoir.

In some implementations of the THC detection system, the plurality of valves may be further arranged such that fluid flow between the components is controllable to deliver an eluent from the sample reservoir to the elution port before the breath constituent sample is conveyed to the sample reservoir. In some such implementations, the system may further include a handheld breath capture module configured to removably connect with the elution port, the handheld breath capture module including a mouthpiece, a saliva trap, and a catch media located between the saliva trap and the elution port when the handheld breath capture module is connected with the elution port. In some further such implementations, the catch media may be silica microbeads having nominal maximum dimensions of between 400 µm and 1500 µm, glass wool, activated charcoal granules, glass wool, layered mesh screens, or frits.

In some implementations of the THC detection system, the system may further include a controller having one or more processors and a memory. The one or more processors may be communicatively connected with the memory, and the memory may store computer-executable instructions for controlling the one or more processors to control the plurality of valves to facilitate the delivering of the eluent from the sample reservoir to the elution port, the conveying of the breath constituent sample from the elution port to the sample reservoir, the combining of the at least a first portion of the indicator with the breath constituent sample to form the sample adduct, the combining of the at least a first portion of the solvent with the sample adduct, and the delivering of the combined sample adduct and solvent to the optical measurement chamber.

In some implementations of the THC detection system, the system may further include an activation cell, and the plurality of valves may be further arranged such that fluid flow between the components is controllable to permit the combined sample adduct and solvent to be delivered to the activation cell prior to delivering the combined sample adduct and solvent to the optical measurement chamber.

In some implementations of the THC detection system, the system may further include a first calibration sample reservoir and a second calibration sample reservoir. In such implementations, the plurality of valves may be further arranged such that fluid flow between the components is controllable to permit at least a second portion of the indicator from the indicator chamber to be combined with a first calibration sample in the first calibration sample reservoir to form a first calibration sample adduct with any THC that is present in the first calibration sample, permit at least a second portion of the solvent to be combined with the first calibration sample adduct, permit the combined first calibration sample adduct and solvent to be delivered to the optical measurement chamber, permit at least a third portion of the indicator from the indicator chamber to be combined with a second calibration sample in the second calibration sample reservoir to form a second calibration sample adduct with any THC that is present in the second calibration sample, permit at least a third portion of the solvent to be combined with the second calibration sample adduct, and permit the combined second calibration sample adduct and solvent to be delivered to the optical measurement chamber. In some such implementations, the first calibration sample may contain no THC and the second calibration sample may contain a known amount of THC. In some alternative such implementations, the first calibration sample may contain a first known amount of THC and the second calibration sample may contain a second known amount of THC that is greater than the first known amount of THC.

In some implementations of the system, the system may further include a controller having one or more processors and a memory. In such implementations, the one or more processors may be communicatively connected with the memory and the memory may store computer-executable instructions for controlling the one or more processors to control the plurality of valves to facilitate the delivering of the eluent from the sample reservoir to the elution port, the conveying of the breath constituent sample from the elution port to the sample reservoir, the combining of the at least a first portion of the indicator with the breath constituent sample to form the sample adduct, the combining of the at least a first portion of the solvent with the sample adduct, the delivering of the combined sample adduct and solvent to the optical measurement chamber, the combining of the at least a second portion of the indicator with the first calibration sample to form the first calibration sample adduct, the combining of the at least a second portion of the solvent with the first calibration sample adduct, the delivering of the combined first calibration sample adduct and solvent to the optical measurement chamber, the combining of the at least a third portion of the indicator with the second calibration sample to form the second calibration sample adduct, the combining of the at least a third portion of the solvent with the second calibration sample adduct, and the delivering of the combined second calibration sample adduct and solvent to the optical measurement chamber.

In some such implementations, the THC detection system may further include a first activation cell and a second activation cell, and the plurality of valves may be further arranged such that fluid flow between the components is controllable to permit the combined sample adduct and solvent to be introduced into the first activation cell prior to delivering the combined sample adduct and solvent to the optical measurement chamber and permit the combined second calibration sample adduct and solvent to be delivered to the second activation cell prior to delivering the combined second calibration sample adduct and solvent to the optical measurement chamber.

In some implementations of the THC detection system, the system may further include an indicator solvent reservoir containing an indicator solvent. In such implementations, the indicator chamber may include a granular or powder indicator and the plurality of valves may be further arranged such that fluid flow between the components is controllable to permit the indicator solvent in the indicator solvent reservoir to be delivered to the indicator chamber in order to mix the indicator solvent with the granular or powder indicator to form the indicator. In some such implementations, the granular or powder indicator may include a functionalized fluorophore. In some further such implementations, the fluorophore may be a rhodamine, and in some specific such implementations, the fluorophore may be rhodamine 123.

In some implementations of the THC detection system, the indicator solvent may be hydrochloric acid.

In some implementations of the THC detection system, the indicator may be a diazo-functionalized reactant.

In some implementations of the THC detection system, the system may further include a controller having one or more processors and a memory. The one or more processors may be communicatively connected with the memory and the memory may store computer-executable instructions for controlling the one or more processors to control the plurality of valves to facilitate: the conveying of the breath constituent sample from the elution port to the sample reservoir, the delivering of the indicator solvent to the indicator chamber to form the indicator, the combining of the at least a first portion of the indicator with the breath constituent sample to form the sample adduct, the combining of the at least a first portion of the solvent with the sample adduct, and the delivering of the combined sample adduct and solvent to the optical measurement chamber.

In some implementations of the THC detection system, the system may further include a cleaning agent reservoir and the plurality of valves may be further arranged such that fluid flow between the components is controllable to permit a cleaning agent in the cleaning agent reservoir to be delivered to the optical measurement chamber. In some such implementations, the cleaning agent may be either ethanol or acetonitrile.

In some implementations of the THC detection system, the system may further include a mixing chamber and the plurality of valves may be further arranged such that fluid flow between the components is controllable to permit the sample adduct and the at least a first portion of the solvent to be delivered to the mixing chamber and then from the mixing chamber to the optical measurement chamber. In some such implementations of the system, the mixing chamber may include a short siphon and a long siphon that is longer than the short siphon, and the plurality of valves may be further arranged such that fluid flow between the components is controllable to permit the sample adduct and the at least a first portion of the solvent to be delivered to the mixing chamber via the long siphon and permit the combined sample adduct and solvent to be removed from the mixing chamber via the short siphon for delivery to the optical measurement chamber.

In some further such implementations of the system, the system may also include a controller having one or more processors and a memory. The one or more processors may be communicatively connected with the memory and the memory may store computer-executable instructions for controlling the one or more processors to control the plurality of valves to facilitate: the conveying of the breath constituent sample from the elution port to the sample reservoir, the combining of the at least a first portion of the indicator with the breath constituent sample to form the sample adduct, the combining of at least the first portion of the solvent with the sample adduct, the delivering of the sample adduct and the at least a first portion of the solvent to the mixing chamber, and the delivering of the combined sample adduct and solvent to the optical measurement chamber.

In some implementations of the THC detection system, the system may further include a pump and the plurality of valves may be further arranged such that fluid flow between the components is controllable to permit pressure from the pump to be applied to the mixing chamber so as to force the combined sample adduct and solvent into the short siphon.

The above implementations are only some of the implementations discussed herein, and do not constitute an exhaustive list of implementations consistent with the scope of this disclosure. Further implementations will be evident from the more detailed discussion provided by the entirety of this disclosure.

BRIEF DESCRIPTION OF THE DRAWINGS

The various implementations disclosed herein are illustrated by way of example, and not by way of limitation, in the figures of the accompanying drawings, in which like reference numerals refer to similar elements.

DETAILED DESCRIPTION

The analysis systems discussed herein generally employ a luminescence-based approach to measuring the amount of a target substance, e.g., THC, in a person's breath. At a high level, a desired quantity of a person's breath is flowed through some form of catch media, e.g., such as catch media in a small, portable, hand-held device, and then eluted; the resulting elution is then used as the "unknown" sample in the analysis system, and is subjected to one or more mixing, separation, and/or activation operations prior to being optically evaluated to determine an amount of THC that is present in the sample.

Quantitative detection of THC in human breath is challenging due to the extremely low concentration of THC in human breath and the presence of many common, similarly structured contaminants or chemical interferences. As disclosed herein, breath constituents from one or more (e.g., 1-3) exhalations may be captured with a handheld device for roadside analysis. Any THC in a breath sample taken with the device can be captured by adsorption on a catch medium or catch media. THC adsorbed on the catch medium may be eluted from the capture medium using a polar organic solvent. A basic buffer and an aqueous diazotized fluorophore solution may then be added to the capture solution to form a fluorescent-labeled THC adduct in a sample adduct solution having a basic pH.

After formation of the adduct solution, a nonpolar organic solvent may be added to the sample adduct solution, the resulting mixture vigorously mixed, and the mixture then allowed to separate into polar and nonpolar phase layers. Any fluorescent-labeled THC-adduct will be contained in the nonpolar layer, and thereby isolated by solvent extraction from molecular species that dissolved in polar, but not nonpolar solvents.

Once the sample adduct, if any, is isolated in the nonpolar fraction of the solvent extraction, it can then be detected and quantified by optical techniques, for example measuring the fluorescence of the fluorescent-labeled adduct and determining a quantity of any THC captured from the original breath sample based on the measured fluorescence.

Figure 1:
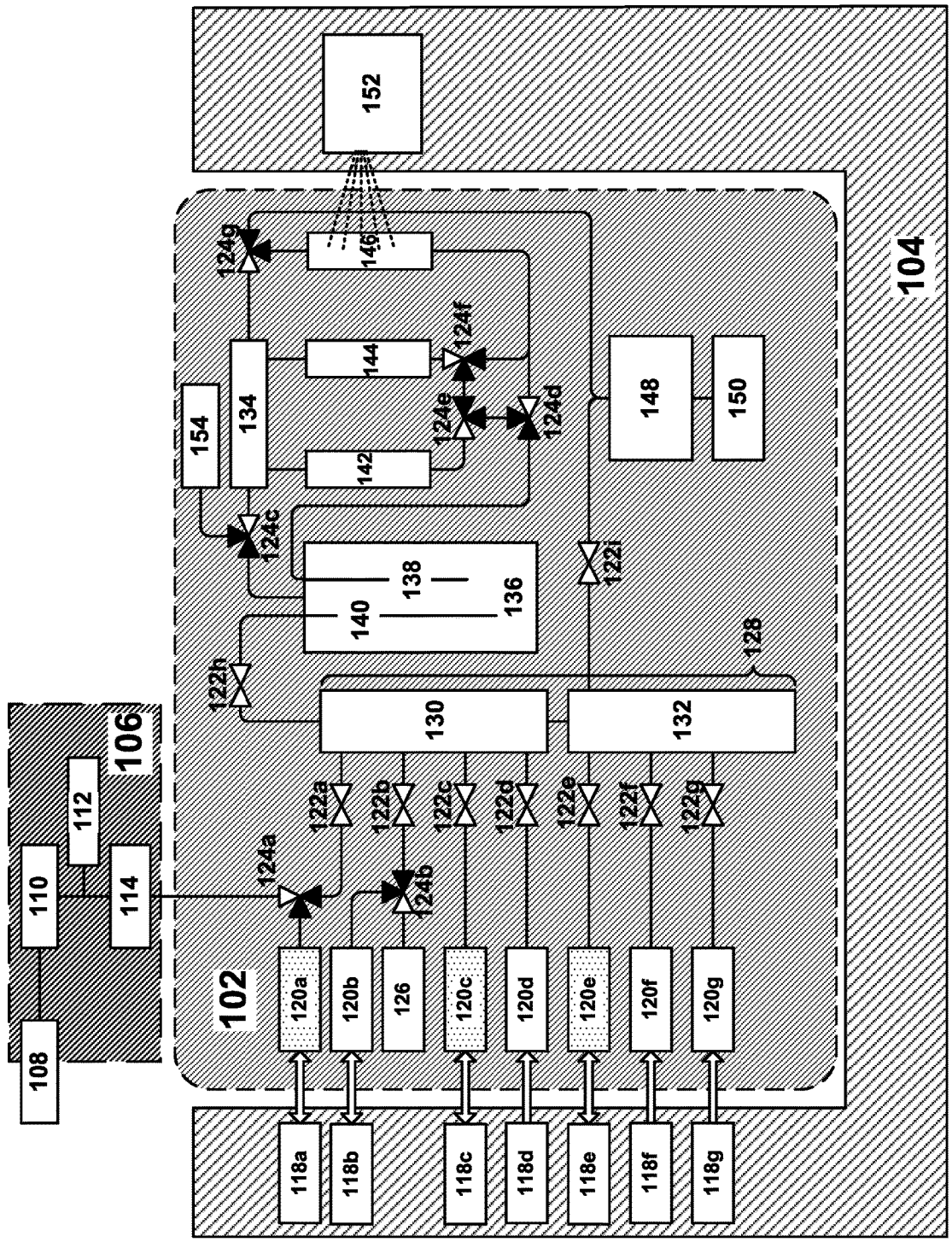
FIG. 1 depicts a schematic of an example target substance analysis system.

FIG. 1 depicts a schematic of an example target substance analysis system. In FIG. 1, the example target substance analysis system is configured to facilitate the detection of tetrahydrocannabinol (THC) in a person's breath, thereby allowing for "BREATHALYZER®" type testing for people suspected of being under the influence of THC. As will be appreciated from the following discussion, the detection of THC in a breath sample may involve a number of different steps, and it is to be understood that while these steps are described with respect to a particular embodiment of a THC analysis system, other embodiments falling within the scope of this disclosure may operate differently from the specific examples discussed but may nonetheless still fall within the scope of the disclosure.

In FIG. 1, the analysis system 100 includes components grouped into three general assemblies: a cartridge 102, a base station 104, and a breath capture module 106. These three assemblies may be interconnected or disconnected during operation to facilitate the analysis of a captured breath constituent sample. It is to be understood that other implementations of the concepts discussed herein may offer similar capabilities, but without one or more of such assemblies (or using similar, but different, assemblies).

In the depicted implementation, components relating to the collection of a breath constituent sample from a subject may be contained in a breath capture module (BCM) 106. Such a BCM may be designed to be relatively lightweight and may have features, such as a catch media 114, that are configured to promote the capture of breath constituents from a person's breath as the person exhales through the BCM 106. The BCM 106 may, for example, be a BCM such as those described in U.S. Patent Application No. 62/337,286, previously incorporated by reference herein. In some implementations, the BCM 106 may include a plurality of microbeads or microspheres, as discussed in U.S. Patent Application No. 62/337,286, that are sandwiched between and retained by two mesh screens. In some such implementations, a woven or fibrous filter media or membrane may be interposed between each mesh screen and the microbeads or microspheres; such a woven or fibrous filter media or membrane may provide further surface area onto which breath constituents may adsorb during sample collection and may enhance the ability of the BCM 106 to capture useful samples. For example, in some implementations, the BCM 106 may include one or more layers of filter media such as TECHNOSTAT® 90 PLUS, which is a meltblown synthetic fiber carried on a spunbond polypropylene backing material. TECHNOSTAT® 90 PLUS is manufactured by Hollingsworth & Vose of East Walpole, Massachusetts, and is distributed in the United States of America by Superior Felt & Filtration of McHenry, Illinois, at the time of this writing. In implementations utilizing TECHNOSTAT® 90 PLUS or a similar filter media, the BCM 106 may, in some instances, omit additional filter media such as microbeads and instead rely on one or more layers of the filter media. In some such implementations, the filter media may be sandwiched between mesh screens to provide support to the filter media and to prevent the filter media from getting dislodged. In other such implementations, the filter media may not be sandwiched between mesh screens but may be clamped in place directly, e.g., about the periphery of the filter media.

The BCM 106 may also include a mouthpiece 108, to allow the person to exhale into the BCM 106, and a saliva trap 110, which may prevent or hinder saliva or spittle from reaching the catch media 114. The BCM may also include electronics (not shown), such as one or more processors and a memory storing instructions for controlling the one or more processors, that may control or monitor operation of the BCM 106 and provide information regarding the progress of the sample collection using the BCM 106. For example, the BCM 106 may include a pressure sensor 112 that has a pressure measurement port that is interposed between the saliva trap 110 and the catch media 114 so as to monitor the pressure downstream of the saliva trap 110 and upstream of the catch media 114. The one or more processors may monitor the data from the pressure sensor and determine therefrom the amount of air that is blown into the mouthpiece 108, through the saliva trap 110, and then delivered to the catch media 114. When the amount of exhaled breath that passes through the BCM 106 exceeds a predetermined amount (as determined from the pressure sensor data, or from another sensor providing similar information), e.g., 3 liters, then the one or more processors may cause a signal to be provided that a sufficient sample has been collected, e.g., the BCM 106 may be caused to emit a "beep" or provide some other sort of indication that a sufficient sample has been collected.

After a breath constituent sample is collected in the BCM 106, the BCM 106 may be connected to the cartridge 102 to allow the breath constituent sample to be drawn out of the BCM 106 and analyzed by the analysis system 100.

The cartridge 102 may include a number of reservoirs that contain various chemicals used in the target substance detection techniques used by the analysis system 100. These reservoirs may be configured to allow the fluids contained in each reservoir to be independently dispensed, as needed, during the analysis process. In some cases, one or more the reservoirs may also be configured to allow fluids outside of the reservoirs to be drawn into the reservoir. In the depicted example analysis system 100, the reservoirs 120 take the form of syringes, each of which is actuated by a corresponding actuator 118. The actuators 118 may be located in the base station 104, which may be a larger unit that includes various "durable" systems or components, e.g., the actuators 118, an optical sensor 152, electronics (not shown), power supply components (not shown), etc. The cartridge, which may include various "consumable" elements, e.g., chemicals used during the analysis, may be removably insertable or connectable with the base station to allow for easy replacement of the consumable elements.

It is to be understood that while syringes and actuators are used in the depicted example system, other fluid storage and dispensing systems may be used in place of, or in addition to, such syringe-based systems. Such alternative implementations are to be understood as also being within the scope of this disclosure.

In the depicted example, each of the reservoirs 120 is connected to a common manifold 128 (which may, for example, be provided by two or more separate manifolds 130 and 132 that are linked together via a tube or other connection so as to form the common manifold 128; this was done to allow commercial off-the-shelf manifolds to be used, and could be avoided by custom-manufacturing a single, integrated manifold). Each such connection of a reservoir 120 to the manifold 128 may include a corresponding valve 122 that may be opened or closed to prevent fluid flow between the corresponding reservoir 120 and the manifold 128. In some instances, there may be an additional diverter or 3-way valve that is also interposed between some of the reservoirs 120 and the manifold 128 to allow the fluid that is stored in such reservoirs to be delivered not only to the manifold 128, but also alternatively to another location. In such scenarios, the functionality of the diverter valve and the shut-off valve may be combined into a single valve structure, e.g., a 3-way valve with an integral shut-off capability.

The common manifold may also be configured to allow fluids from the reservoirs 120 to be directed to one or more downstream components, such as a mixing chamber 136, a first activation cell 142, a second activation cell 144, an optical measurement chamber 146, a waste receptacle 148, or other downstream components.

FIGS. 2 through 25 depict the example analysis system of FIG. 1 during various operational phases, and will be referred to in the following discussion describing the operation of the example analysis system during a typical breath constituent analysis. For clarity, certain conventions are adopted in these Figures. For example, valves are represented by two or three triangles pointing towards a common center point; each triangle may represent a port on the valve—if a triangle is black, this indicates that fluid may flow through the port corresponding to that triangle; if a triangle is white, this indicates that fluid is prevented from flowing through the port corresponding to that triangle. Additionally, white arrows have been overlaid on flow paths to indicate the direction of fluid flow at that point in the analysis process.

Figure 2:
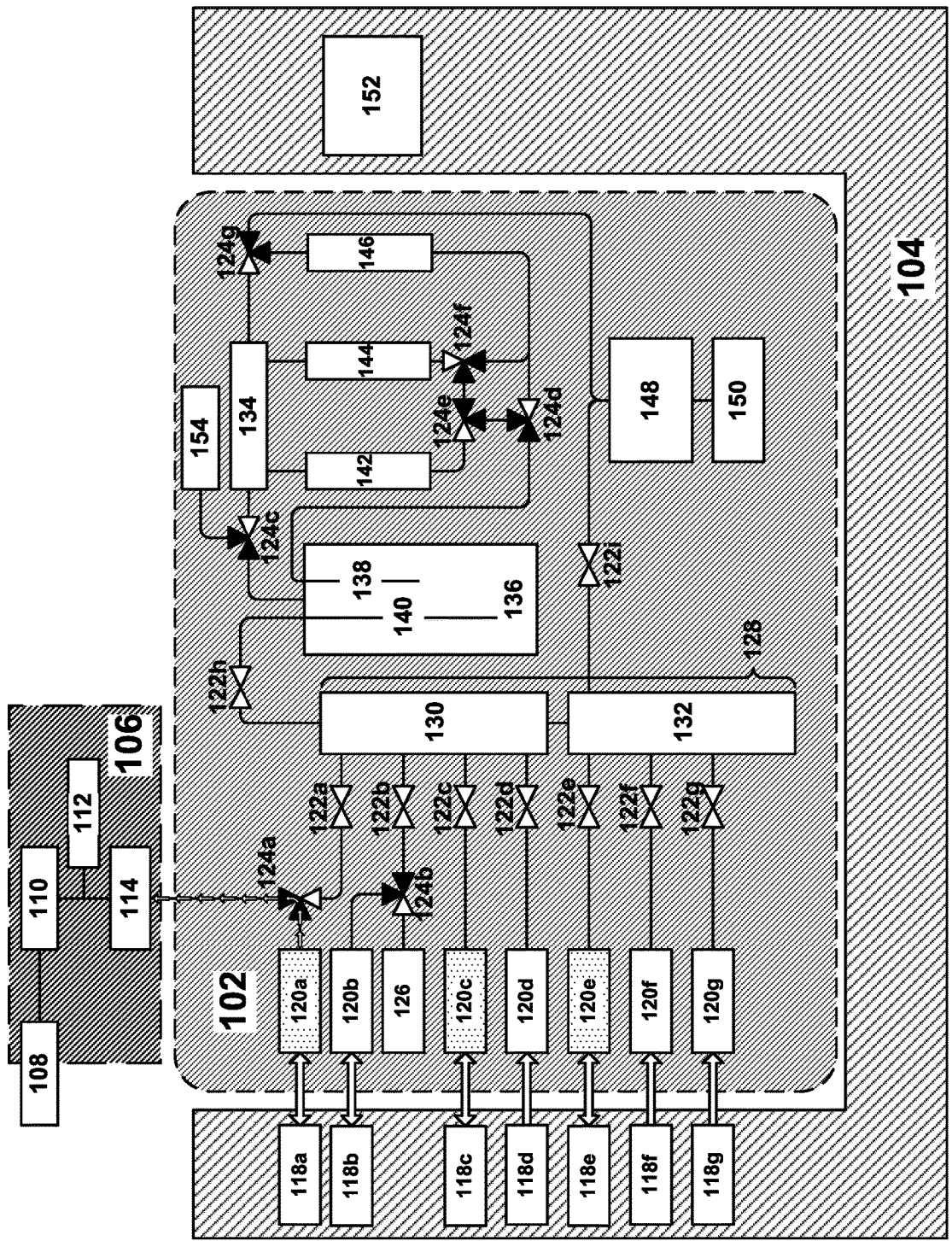
FIG. 2 depicts the example target substance analysis system of FIG. 1 during delivery of an eluent from a sample reservoir.

In FIG. 2, the analysis may begin with the collection of the breath constituent sample from the BCM 106. To begin with, the BCM 106 may be connected to an elution port in the cartridge 102 (or a similar port on the base station 104), and an eluent may be delivered from a sample reservoir 120*a* to the elution port and thereby to the catch media 114 of the BCM 106. For example, a three-way valve 124*a* may be actuated such that the sample reservoir 120*a* is in fluidic communication with the catch media 114. A sample actuator 118*a* may then be actuated so as to meter out a desired amount of eluent from the sample reservoir 120*a* and deliver the metered out amount of eluent to the catch media 114. For example, 250 μL of eluent may be dispensed from the sample reservoir 120*a* and delivered to the catch media 114.

Figure 3:
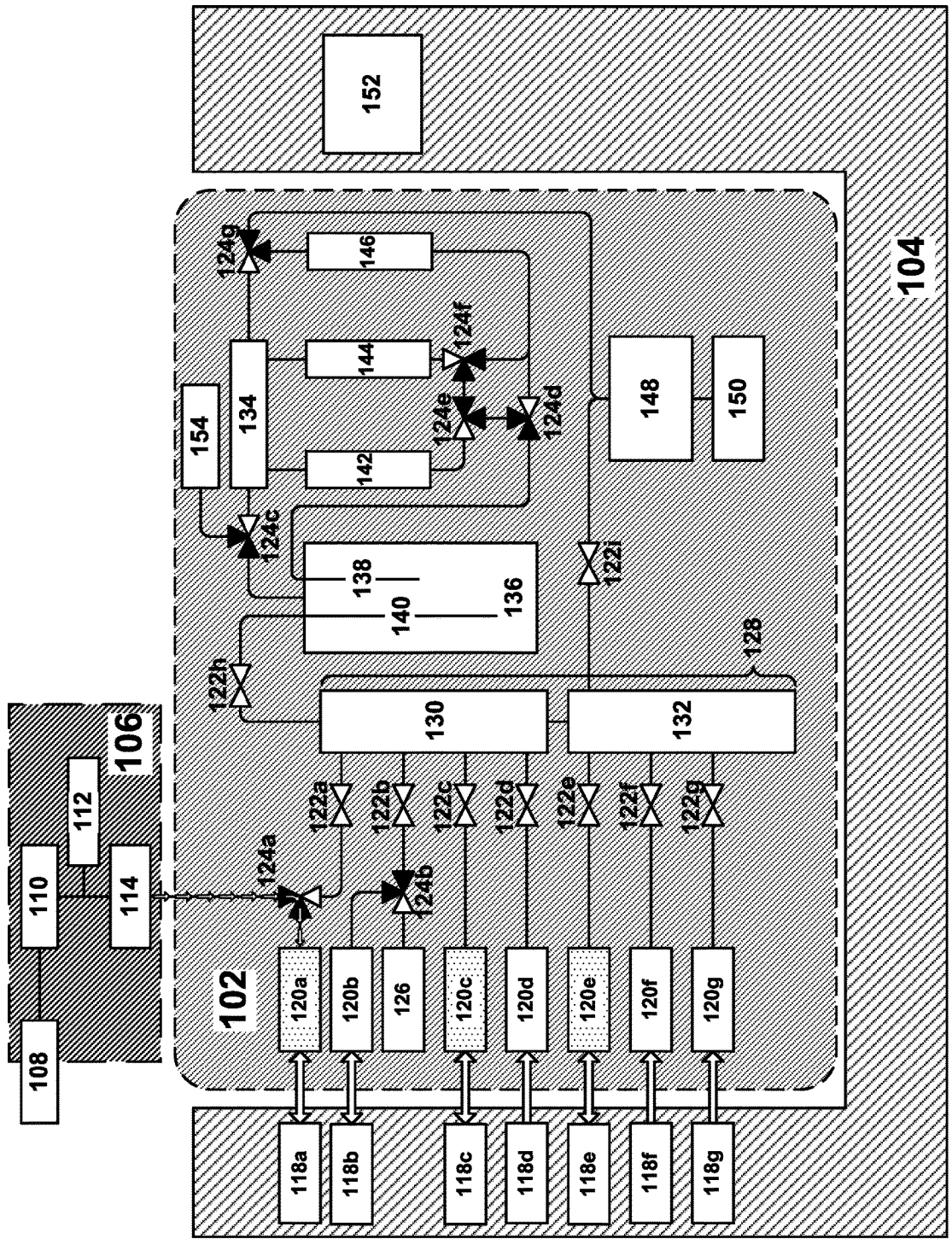
FIG. 3 depicts the example target substance analysis system of FIG. 1 during recovery of an eluted breath constituent sample.

The eluent, which may, for example, be ethanol (EtOH), may then be allowed soak the catch media 114, e.g., for approximately 30 seconds, so as to elute any breath constituents that have adsorbed onto the catch media 114 into the eluent. After the catch media 114 has been soaked by the eluent for a sufficiently long enough period of time to result in most of the breath constituents being eluted, the resulting eluent and eluted breath constituents may be withdrawn from the BCM 106 and returned to the sample reservoir 120*a*, as shown in FIG. 3. For example, this may be achieved by causing the sample actuator 118*a* to be operated in the reverse manner as it was while delivering the eluent from the sample reservoir 120*a* to the catch media 114, e.g., as in FIG.

2. It is to be understood that, if desired, the eluent may be returned to another reservoir (not pictured) which may be sterile or otherwise uncontaminated after collection—as such a solution would involve further components and complexity for little or no benefit, the implementation described herein returns the eluent and eluted breath constituents to the sample reservoir 120*a* to await further processing.

After the elution and collection of the breath constituent sample, the system may be operated so as to add an aqueous diazotized fluorophore solution to the eluted breath constituent sample to produce an adduct with THC molecules that may be in the breath constituent sample. In the present example analysis system, such an aqueous diazotized fluorophore solution may be generated by mixing an indicator solvent with a solid-phase indicator to create the aqueous diazotized fluorophore solution, although it is envisioned that such mixing may be unnecessary if alternative aqueous diazotized fluorophore solutions are used that are stable when in liquid form.

Figure 4:
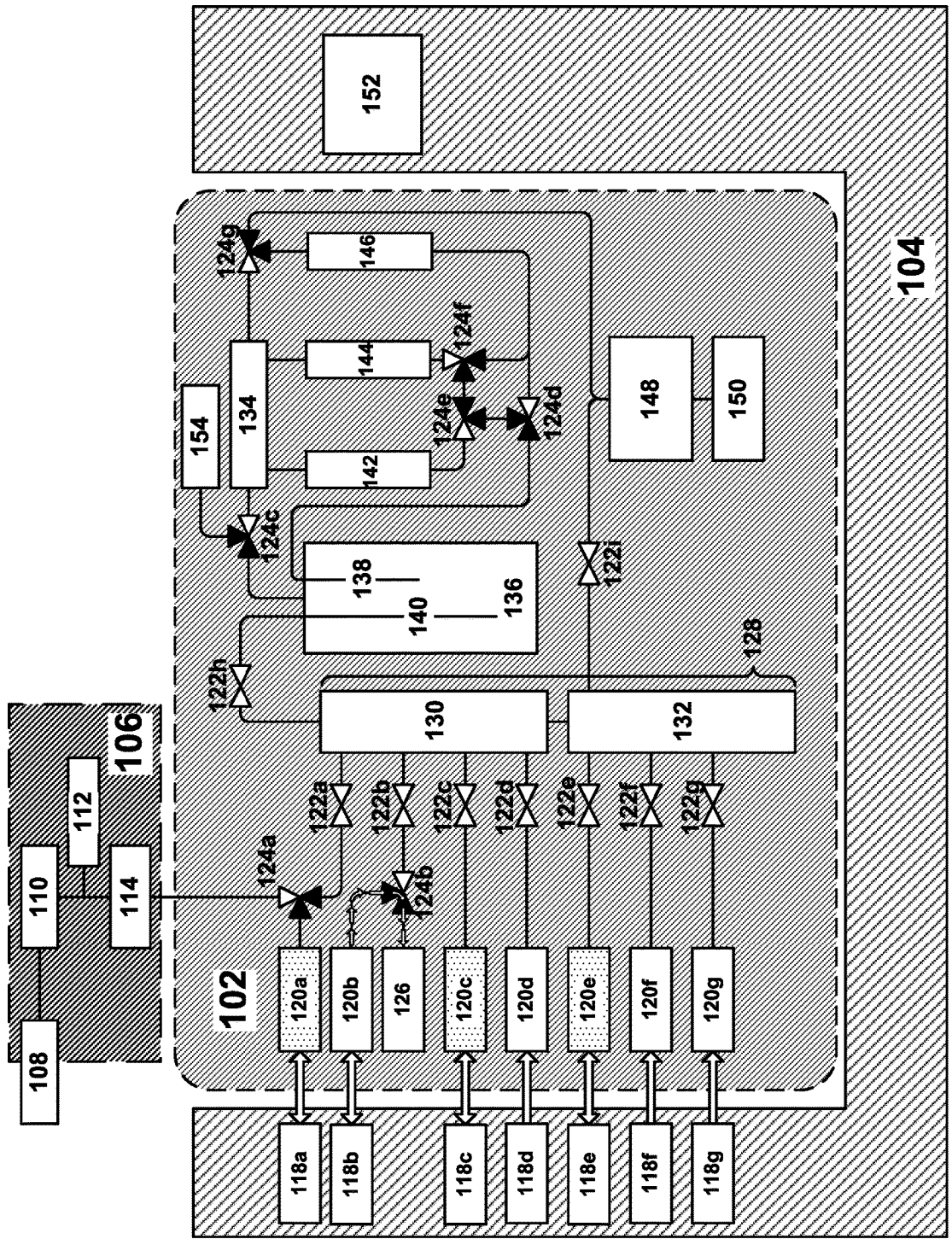
FIG. 4 depicts the example target substance analysis system of FIG. 1 during delivery of an indicator solvent to an indicator chamber.

The aqueous diazotized fluorophore solution may be produced just before, during, or just after the elution of the breath constituent sample from the catch media 114. For example, a three-way valve 124*b* may be actuated so as to put an indicator solvent reservoir 120*b* containing an indicator solvent in fluidic communication with an indicator chamber 126 containing a solid-phase indicator. The indicator solvent reservoir 120*b* containing the indicator solvent may be actuated by an indicator solvent actuator 118*b* so as to dispense a quantity of the indicator solvent into the indicator chamber 126 that contains the solid-phase indicator, as shown in FIG. 4. After the indicator solvent has been introduced into the indicator chamber 126, the solid-phase indicator may be allowed to dissolve into the indicator solvent for a long enough interval to produce a desired quantity of liquid-phase indicator.

Figure 5:
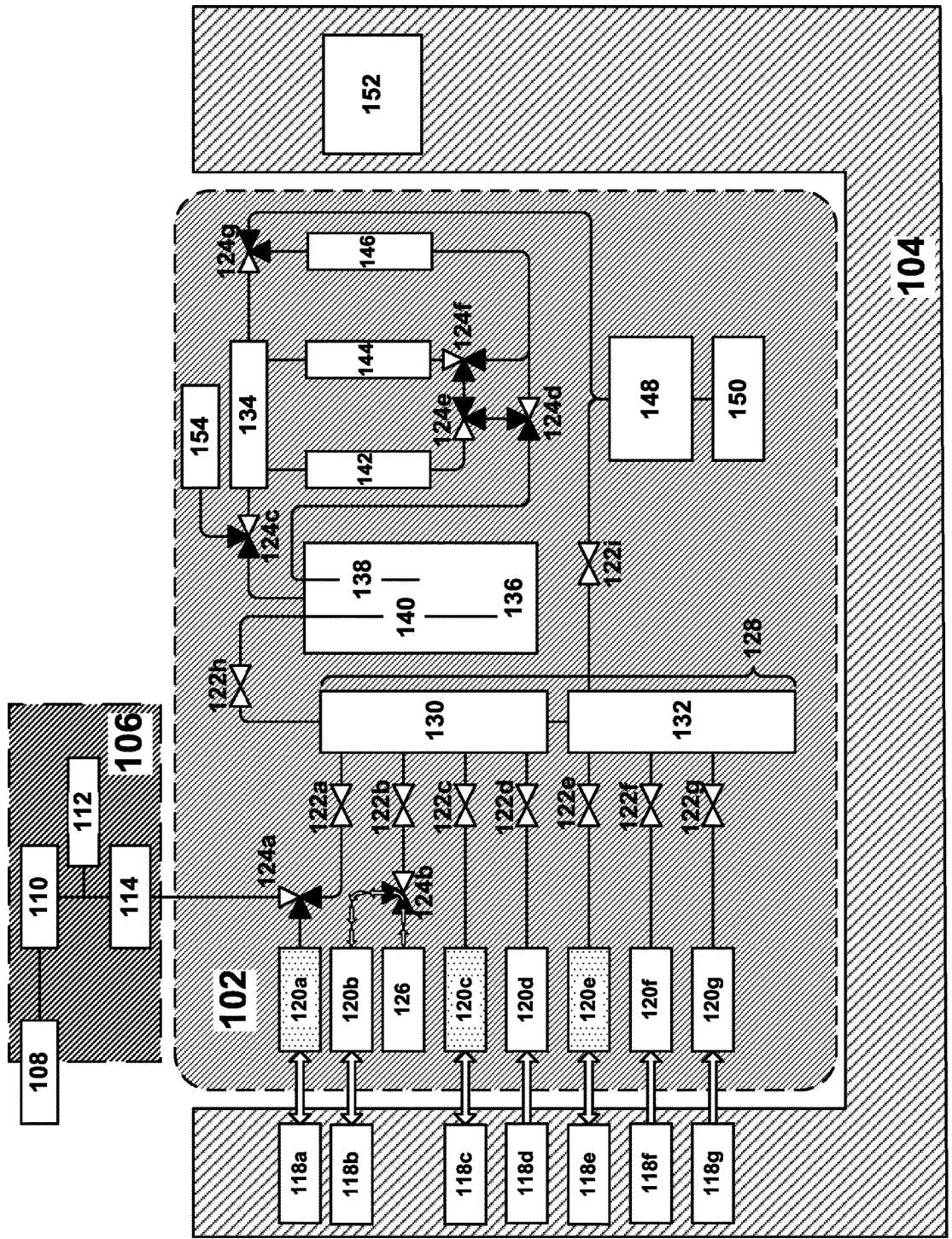
FIG. 5 depicts the example target substance analysis system of FIG. 1 during recovery of a liquid indicator from the indicator chamber.
Figure 6:
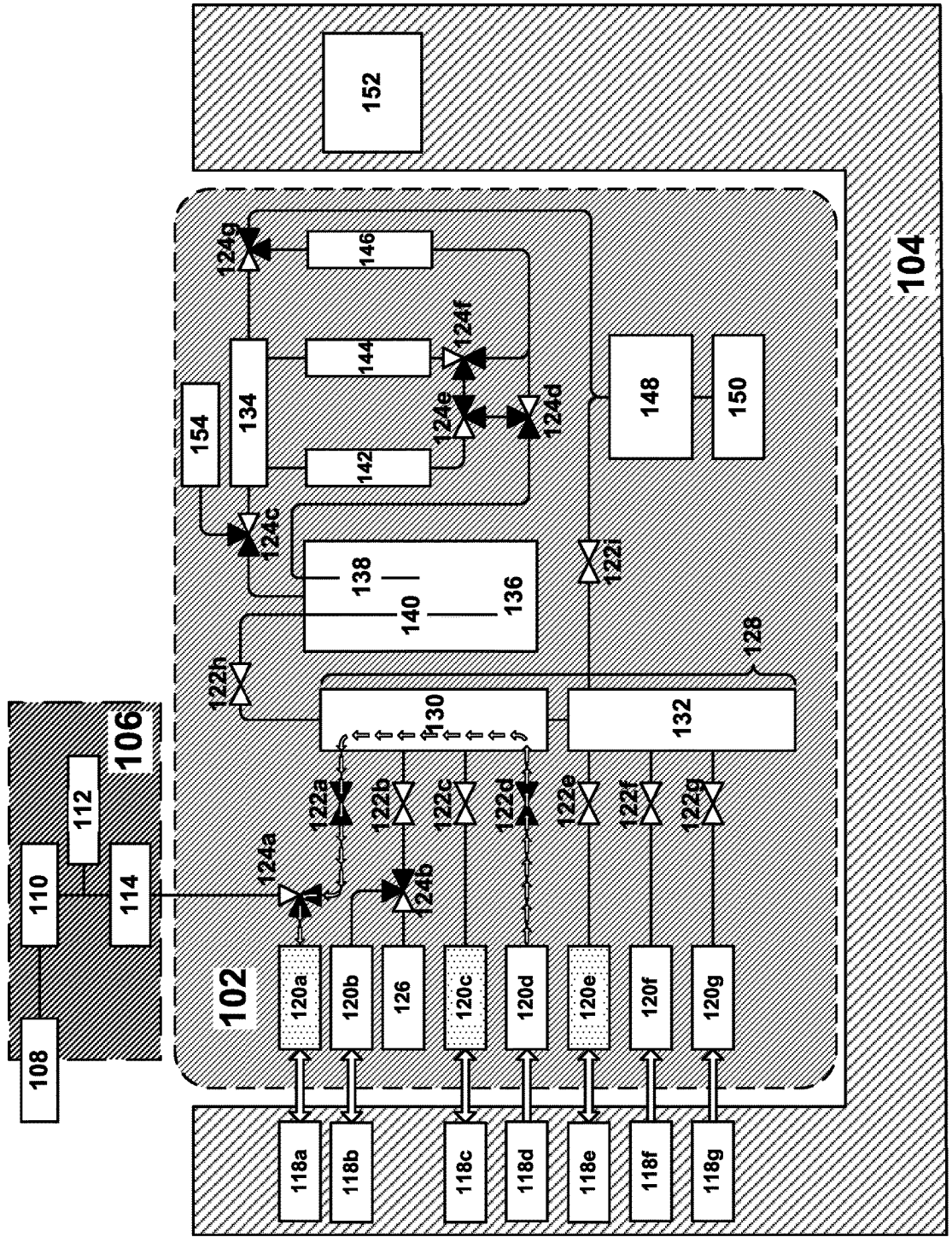
FIG. 6 depicts the example target substance analysis system of FIG. 1 during delivery of a basic buffer to the eluted breath constituent sample.
Figure 7:
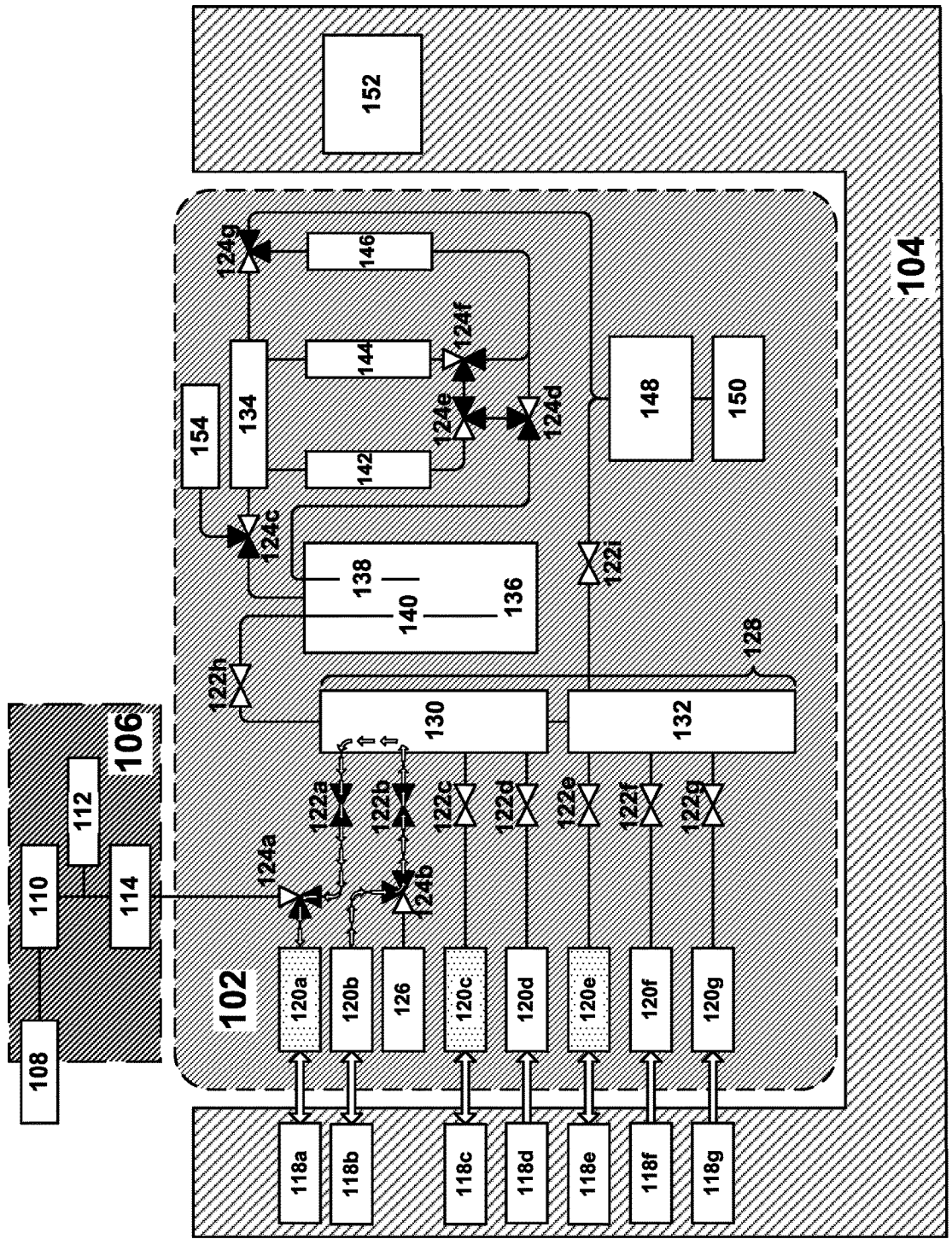
FIG. 7 depicts the example target substance analysis system of FIG. 1 during delivery of the indicator to the breath constituent sample.

The indicator solvent may be acidic, e.g., 100 µM hydrochloric acid (HCl), and may be added in sufficient quantity so as to produce enough indicator so as to be able to provide equal doses of indicator to the sample reservoir 120*a* and to one or more calibration sample reservoirs (if used). In the example analysis system of FIG. 1, at least 750 µL of indicator solvent may be added to the solid-phase indicator in the indicator chamber 126 to allow for the later delivery of 250 µL of liquid indicator to each of the three sample reservoirs. After sufficient dissolution time has elapsed, the liquid-phase indicator that is present in the indicator chamber 126 may be returned to the indicator solvent reservoir 120*b*, e.g., by actuating the indicator solvent actuator 118*b* in a reverse manner from how it was actuated in order to deliver the indicator solvent to the indicator chamber 126, as shown in FIG. 5. In some implementations, the indicator solvent actuator 118*b* may be repeatedly actuated so as to drive the mixture of indicator solvent and solid-phase (or dissolving) indicator into and out of the indicator solvent reservoir 120*b* so as to promote better mixing and dissolution between the indicator solvent and the solid-phase indicator.

Once the indicator has been formed and the breath constituent sample collected, the indicator may then be combined with the eluted breath constituent sample, as well as with any calibration samples that may be used in the analysis system, to form a fluorescent-labeled THC adduct that may later be used to determine the amount of THC present in each sample. In the example analysis system, two calibration samples are provided, although similar analysis systems may utilize more or less (or no) calibration samples, depending on the accuracy desired or whether alternative calibration mechanisms are used. In the present example analysis system, a negative calibration sample and a positive calibration sample are both used. The negative calibration sample has no THC present but includes a similar type and quantity of fluid as was used to elute the breath constituent sample, and may be stored, for example, in a first calibration sample reservoir 120*c*. Conversely, the positive calibration sample has a known amount of THC present in a similar type and quantity of fluid as was used to elute the breath constituent sample, and may be stored, for example, in a second calibration sample reservoir 120*e*. The positive calibration sample may have an amount of THC thought to be slightly higher, e.g., 10% higher, than the amount of THC that could reasonably be expected to be in an eluted breath constituent sample so that the fluorescent response of the breath constituent sample during the analysis is bracketed by the positive and negative calibration samples. However, it is to be understood that other implementations may, for example, include a non-zero negative control (not truly negative) or a positive control that is lower than the expected maximum quantity of THC that could reasonably be expected to be in the eluted breath constituent sample. For example, if the legal framework surrounding marijuana evolves to allow some amount of THC to be present in a person's breath before the person is considered to be "impaired," then the negative control may be pegged to this lower limit instead of zero.

Fluorescent-labeled THC adducts are stable when in a basic solution, but may rapidly degrade when exposed to an acidic environment. Conversely, the aqueous diazotized fluorophore solution may be stable in an acidic solution, e.g., such as when dissolved in hydrochloric acid. In order to increase the longevity of the THC adducts that may result from mixing of the liquid-phase indicator with the eluted breath constituent sample and/or the calibration samples, the eluted breath constituent sample and the calibration samples may be combined with a basic buffer that may prevent or mitigate the degradation of any THC adducts that are formed when the eluted breath constituent sample and/or the calibration samples are combined with the liquid-phase indicator, e.g., by raising the pH of the eluted breath constituent sample and/or the calibration samples sufficiently high enough that the subsequent addition of an acidic indicator solution to the eluted breath constituent sample and/or the calibration samples does not cause the THC adduct to degrade significantly (or at all).

In the case of the sample reservoir 120*a*, the buffer may be added after the elution process has completed and the eluted breath constituent sample has been retrieved from the BCM 106. This prevents the buffer from diluting the eluent, which may potentially reduce its effectiveness in eluting the breath constituents. The amount of buffer used may, in some implementations, be significantly larger than the amount of eluent, e.g., 500 µL of buffer may be added to 250 µL of eluent, so the buffer may be the dominant mixture component after combination. In order to prevent the buffer from potentially hindering the elution of the breath constituents from the BCM 106, the buffer may be added to the sample reservoir 120*a* after the breath constituents have already been eluted. For example, a buffer valve 122*d* and a sample valve 122*a* may be opened, and the 3-way valve 124*a* may be actuated to as to place the sample reservoir 120*a* into fluidic communication with the manifold 128. The buffer may then be delivered to the sample reservoir 120*a* by actuating a buffer actuator 118*d* that drives the buffer out of a buffer reservoir 120*d*.

In the case of the calibration sample reservoirs, the buffer may be introduced in a similar manner or may, as is the case in this implementation, be pre-loaded into the calibration sample reservoirs during cartridge assembly or preparation.

Figure 8:
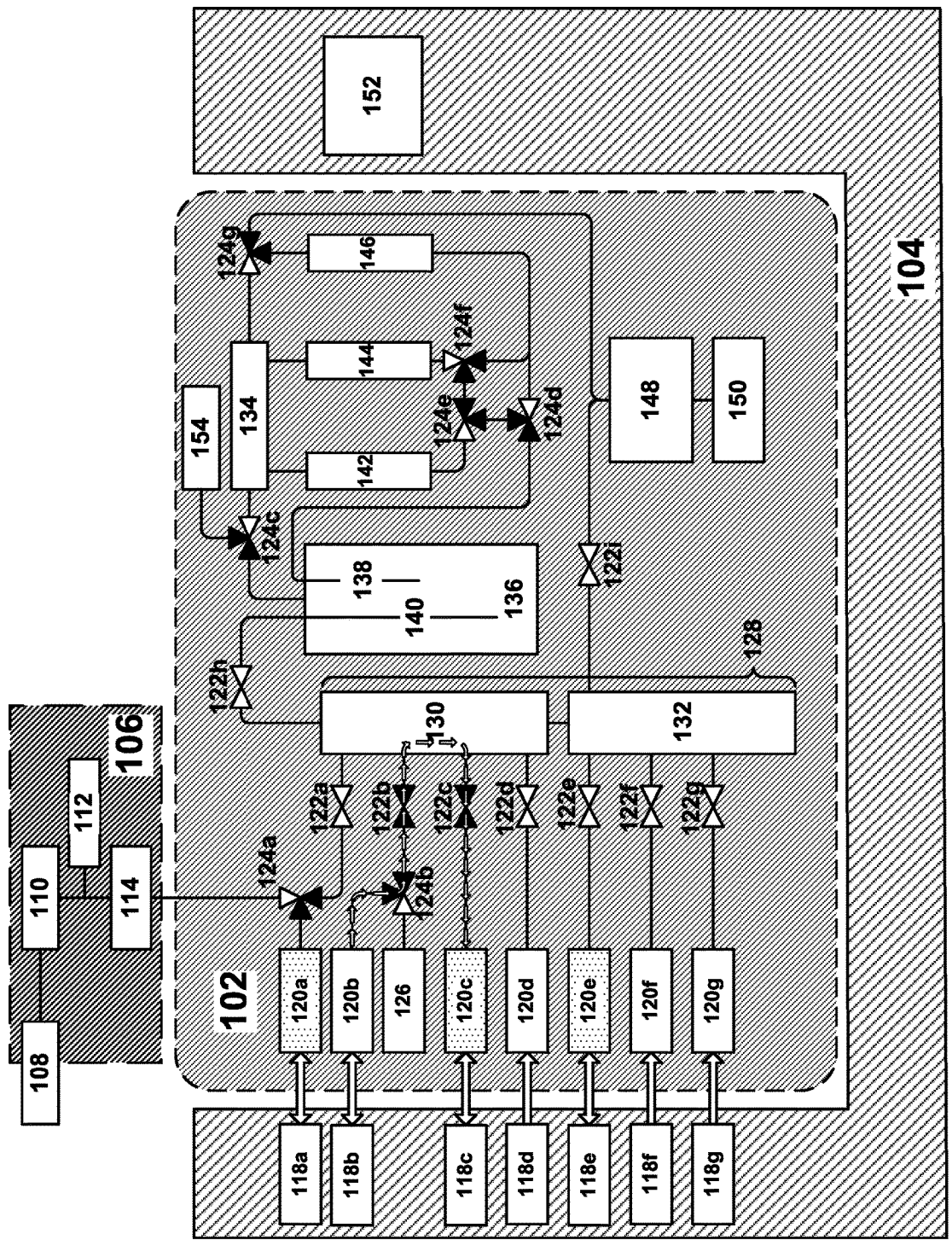
FIG. 8 depicts the example target substance analysis system of FIG. 1 during delivery of the indicator to a first calibration sample.
Figure 9:
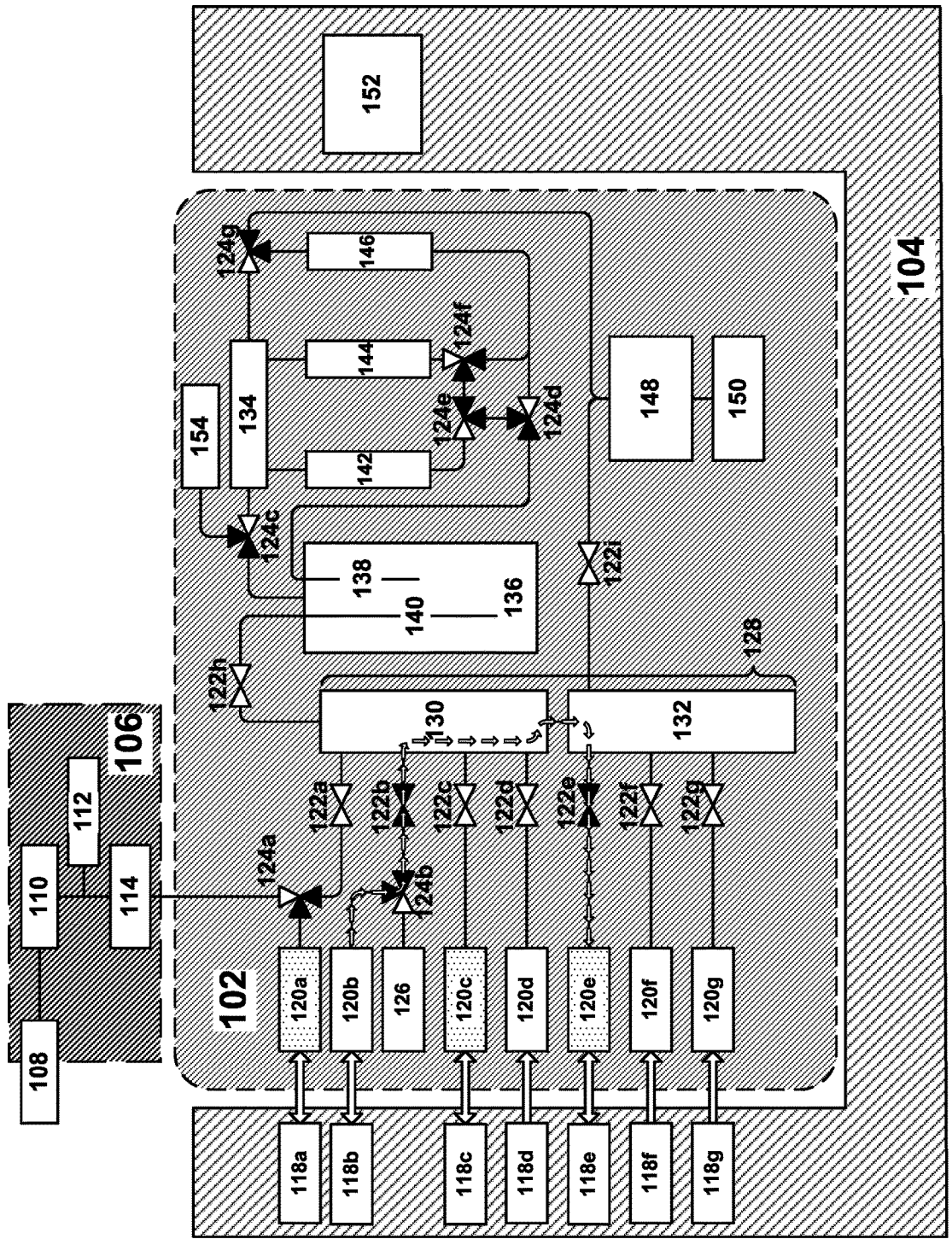
FIG. 9 depicts the example target substance analysis system of FIG. 1 during delivery of the indicator to a second calibration sample.

After the eluted breath constituent sample and/or the calibration samples have been provided with the buffer from the buffer reservoir 120d, the indicator solution from the indicator reservoir 120b may be dispensed to the sample reservoir 120a, the first calibration sample reservoir 120c, and the second calibration sample reservoir 120e. The distribution of the indicator to the sample reservoir 120a, the first calibration sample reservoir 120c, and the second calibration sample reservoir 120e may be performed simultaneously or sequentially, e.g., in sequence with each distribution of indicator occurring immediately after (or otherwise very close in time after) the previous distribution of indicator. For example, in FIG. 7, the 3-way valves 124a and 124b and the buffer valve 122a and an indicator solvent valve 122b have been actuated so as to put the sample reservoir 120a and the indicator solvent reservoir (now containing the liquid indicator solution) 120b, respectively, in fluidic communication with the manifold 128, thus allowing liquid-phase indicator to be pushed out of the indicator solvent reservoir 120b by the actuator 118b and into the sample reservoir 120a. Similarly, the indicator solvent valve 122b and the first calibration sample valve 122c may both be opened (and the other valves 122 on the manifold 128 closed) to put the indicator solvent reservoir 120b in fluidic communication with the first calibration sample reservoir 120c via the manifold 128, as shown in FIG. 8. A similar quantity of liquid indicator may then be delivered to the first calibration sample reservoir 120c by actuating the indicator solvent actuator 118b. The second calibration sample reservoir 120e may also be provided with liquid indicator in a similar manner, e.g., by opening the indicator solvent valve 122b and a second calibration sample valve 122e (and closing the other valves on the manifold 128), as shown in FIG. 9, and driving the liquid indicator from the indicator solvent reservoir into the second calibration sample reservoir 120e using the solvent indicator actuator 118b.

Once the liquid indicator has been added to the eluted sample in the sample reservoir 120a, as well as the first calibration sample reservoir 120c and the second calibration sample reservoir 120e, if used, the amount of THC adduct (if any) that is present in each of the samples may be evaluated. In the example implementation, this occurs in a serial fashion using a largely common set of components located downstream of the manifold 128; these components are washed in between analysis runs in order to prevent cross-contamination of the samples. In other implementations, separate, parallel downstream systems may be used instead, thereby preventing cross-contamination.

Figure 10:
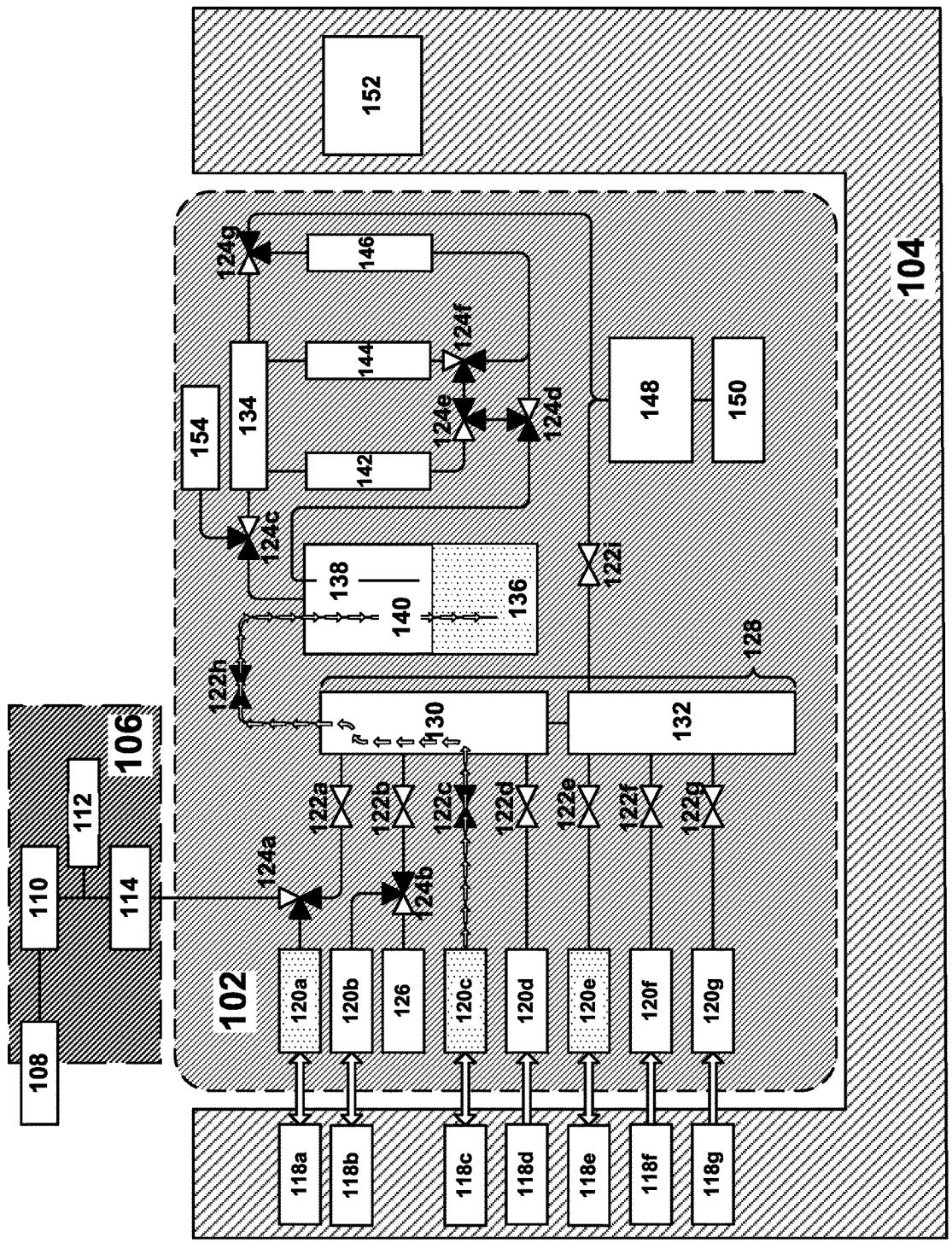
FIG. 10 depicts the example target substance analysis system of FIG. 1 during delivery of the combined indicator and first calibration sample to a mixing chamber.
Figure 11:
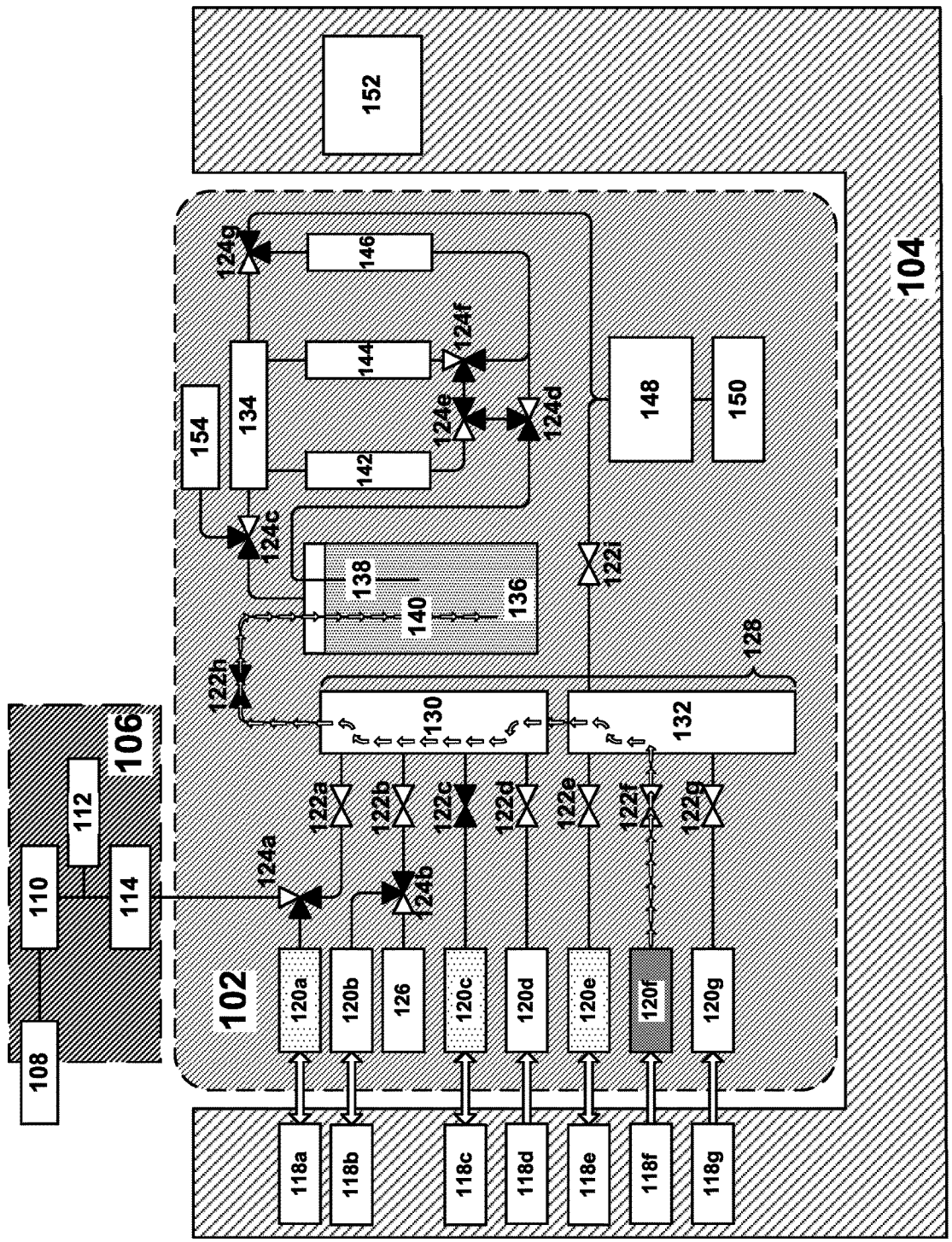
FIG. 11 depicts the example target substance analysis system of FIG. 1 during delivery of a solvent to the mixing chamber.

During operation of the example analysis system, the first calibration sample valve 122c and a manifold valve 122h may both be placed in open states to put the first calibration sample reservoir in fluidic communication with the manifold 128 and, via the manifold 128, a mixing chamber 136. This assumes that the first calibration sample is used; in implementations where such a calibration sample is not used, this portion of the process may be omitted. The first calibration sample, which is a negative calibration sample having no adduct in this case (since there is no THC in it), may then be delivered from the first calibration sample reservoir 120c to the mixing chamber 136 by actuating the first calibration sample actuator 118c, e.g., such as is shown in FIG. 10. Subsequent to the introduction of the first calibration sample to the mixing chamber, the first calibration sample valve 122c may be closed and a solvent valve 122f may be opened to put a solvent reservoir 120f into fluidic communication with the mixing chamber 136 via the manifold 128. A solvent actuator 118f may be actuated to cause the solvent reservoir 120f to dispense a solvent within the solvent reservoir 120f into the mixing chamber 136 via the manifold 128, as is shown in FIG. 11. The solvent, for example, may be a mixture of methyl tertiary butyl ether (MTBE) and heptane or a similar solvent. In some implementations, the delivery of the solvent and the sample (be it a calibration sample or the breath constituent sample) to the mixing chamber 136 may be done in alternating, piecemeal fashion so as to preliminarily mix the two fluids more effectively.

The mixing chamber 136 may serve a two-fold purpose—it may act as a temporary holding area or reservoir for the current sample in which mixing with the solvent may occur and it may also be used as a vessel in which polar/non-polar phase separation may be used in order to separate out a non-polar layer containing the THC adduct from a polar layer of the mixture. The mixing chamber may have multiple inlets into the chamber, e.g., a long siphon 140, a short siphon 138, and, in some cases, a pressurization inlet (not labeled, but connected to 3-way valve 124c). The long siphon 140 may extend to the bottom of the mixing chamber 136 such that the mixing chamber 136 may be completely drained by drawing whatever fluids are within the mixing chamber 136 out through the long siphon 140. The short siphon 138, however, may only extend partway down the mixing chamber 136—the length of the short siphon 138 may be designed such that the short siphon 138 extends nearly to the bottom (but not past the bottom) of the separation layer containing the THC adduct after separation has occurred. This allows the short siphon 138 to be used to siphon off the THC adduct after separation for further processing.

Figure 12:
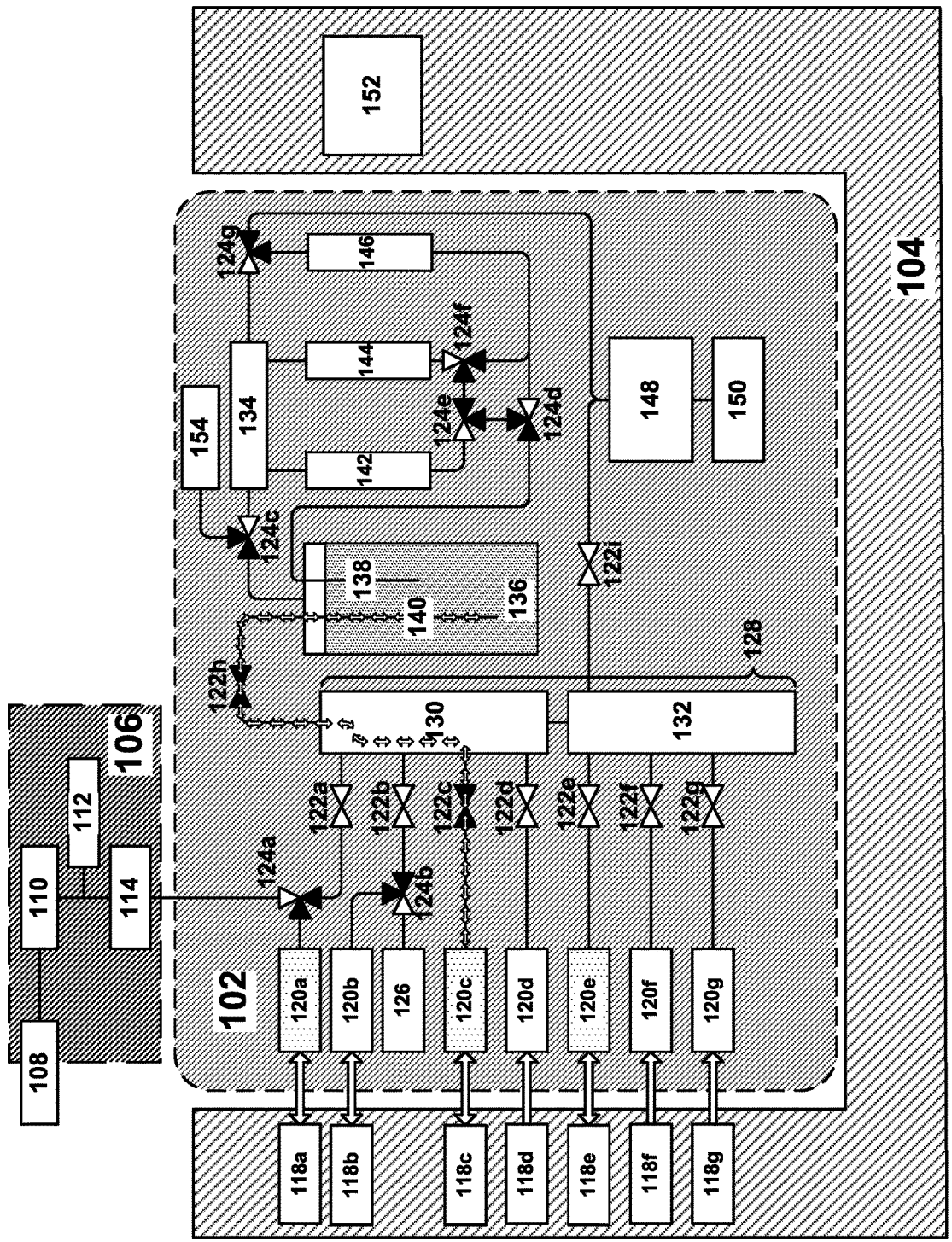
FIG. 12 depicts the example target substance analysis system of FIG. 1 during mixing of solvent and the combined indicator and first calibration sample.
Figure 13:
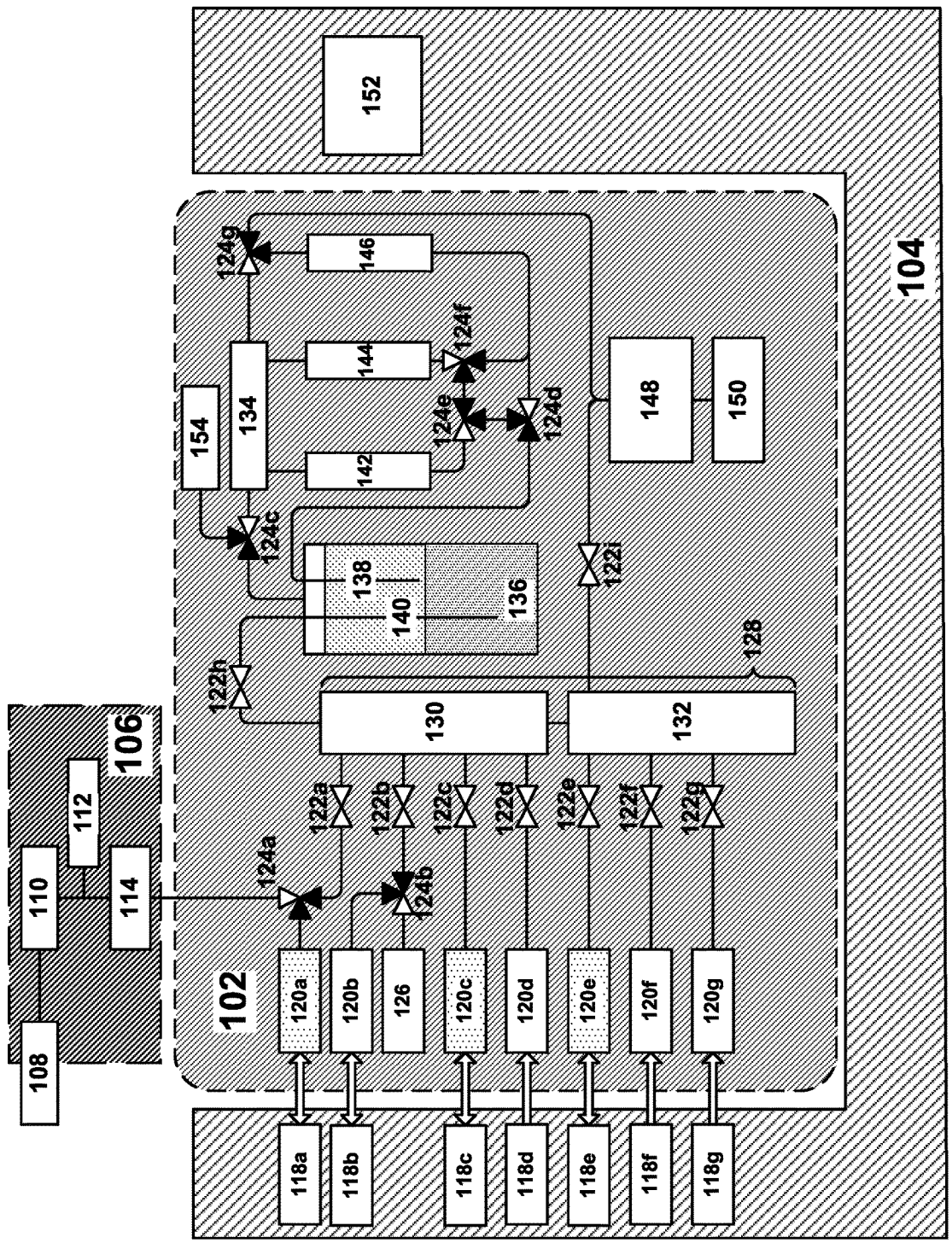
FIG. 13 depicts the example target substance analysis system of FIG. 1 during separation of the mixture in the mixing chamber.

After the combined first calibration sample and liquid indicator and the solvent are both delivered to the mixing chamber 136, the delivered mixture may be withdrawn and re-introduced into the mixing chamber 136 multiple times, e.g., by reciprocating the first calibration sample actuator 118c multiple times, thereby drawing the mixture back into the first calibration sample reservoir 120c and then re-delivering it to the mixing chamber 136 repeatedly, e.g., such as is shown in FIG. 12, which may agitate the mixture and further promote thorough and complete mixing of the solvent with the sample. After such mixing, the mixed solution may be allowed to rest within the mixing chamber 136 so that the mixed solution may separate out into polar and non-polar phases, e.g., such as is shown in FIG. 13.

Figure 14:
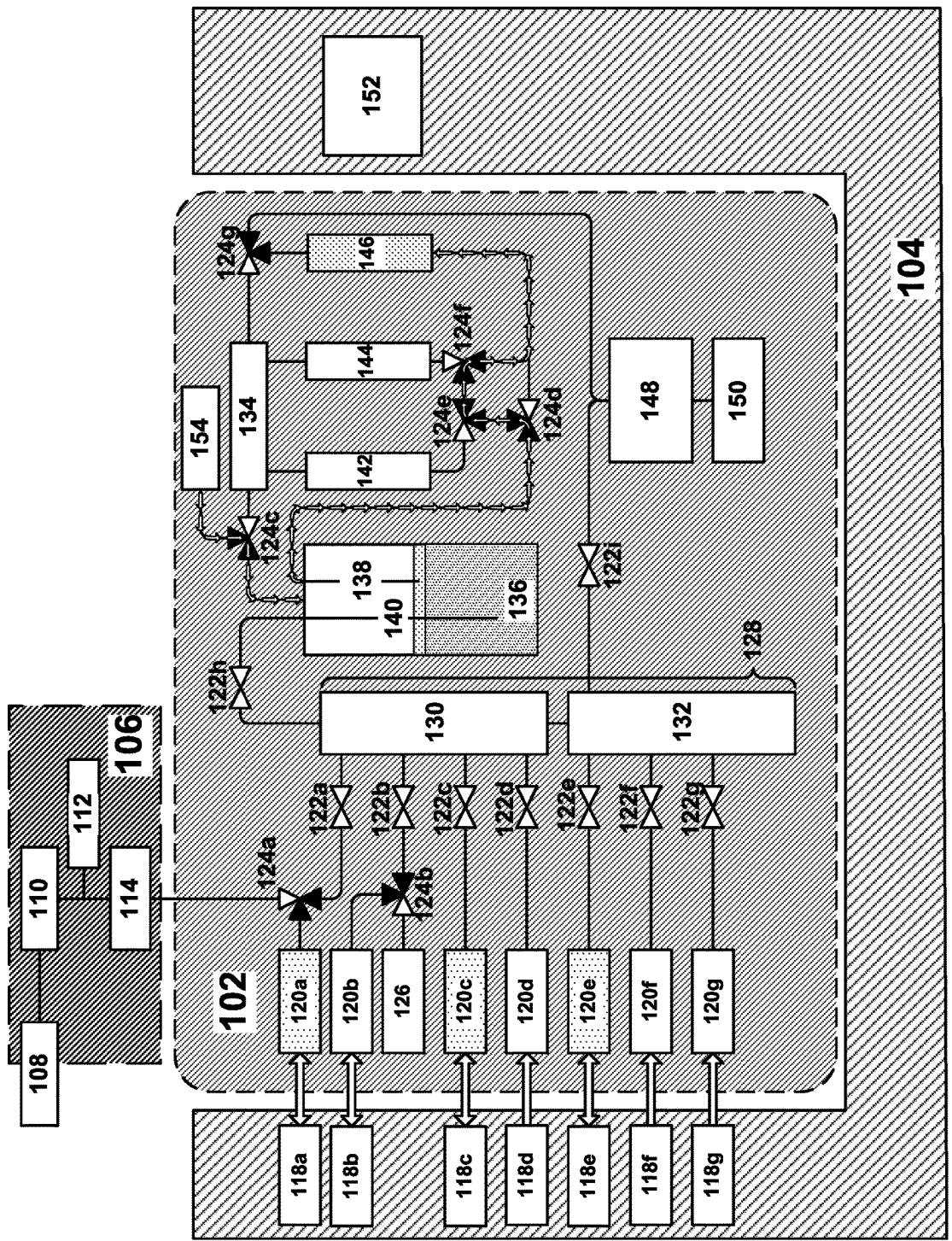
FIG. 14 depicts the example target substance analysis system of FIG. 1 during delivery of a separation layer to an optical measurement chamber.

Once the adduct/solvent/indicator solution has separated in the mixing chamber 136, the separated THC adduct may be delivered to the optical measurement chamber 146, as shown in FIG. 14. For example, 3-way valves 124d, 124e, and 124f may all be set so as to put the mixing chamber 136 in fluidic communication with the optical measurement chamber 146. Another 3-way valve 124c may be actuated so as to put an air pump 154 in fluidic communication with the mixing chamber 136; when the air pump 154 is actuated, the resulting pressure increase in the mixing chamber 136 may drive the separated THC adduct into the short siphon 138 and then into the optical measurement chamber 146.

Figure 15:
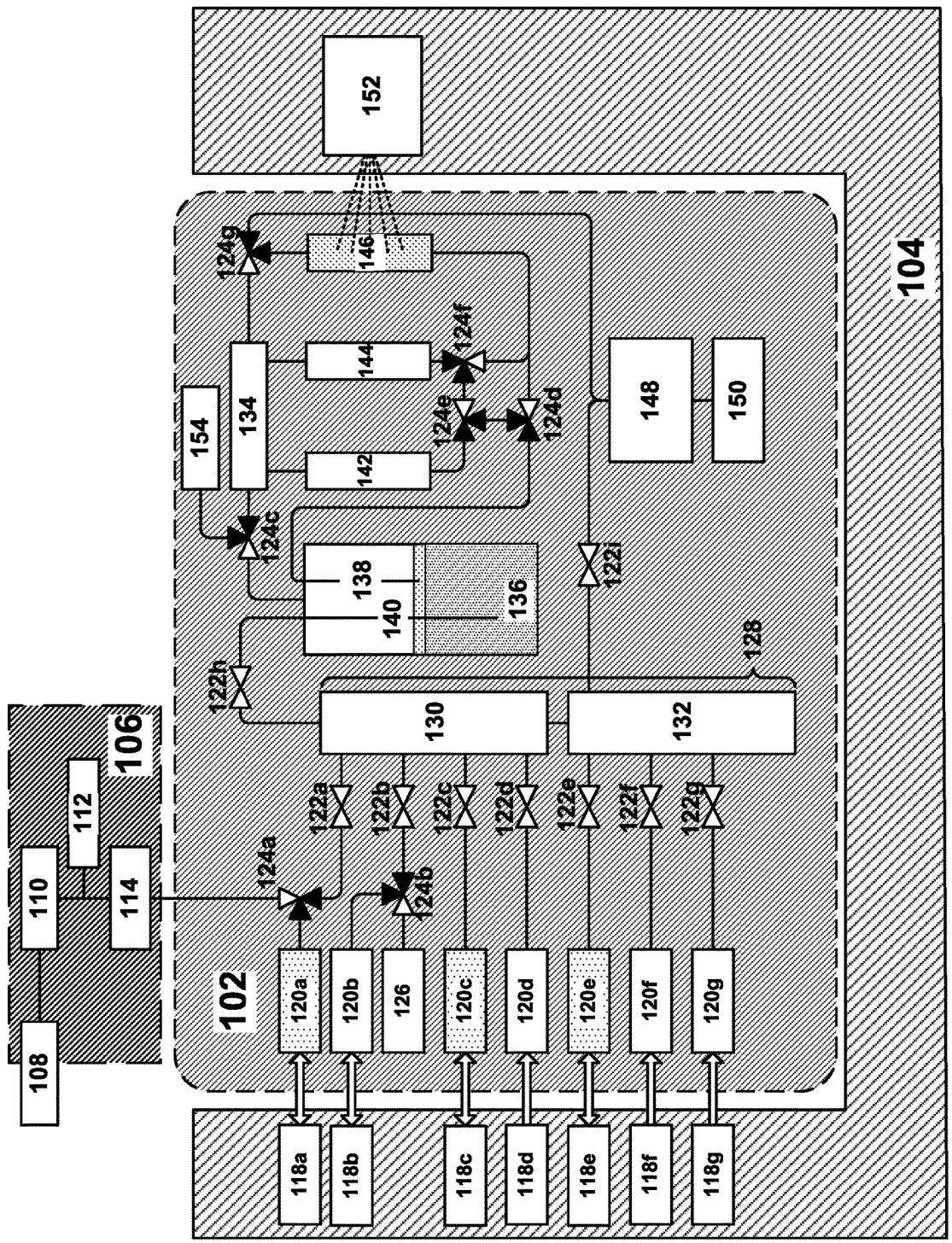
FIG. 15 depicts the example target substance analysis system of FIG. 1 during optical measurement of the contents of the optical measurement chamber.

After the first calibration sample is delivered to the optical measurement chamber 146, the first calibration sample may be optically measured to determine an amount of THC adduct, and thus an amount of THC, that is present in the first calibration sample, e.g., such as is shown in FIG. 15. Such optical measurement may be made by optically stimulating the adduct using light having a first set of wavelengths and then measuring the amount of light having a second set of wavelengths that is then emitted by the THC adduct in the sample in response to such optical stimulation.

Such optical measurement readings may involve a multi-step process. To begin with, the temperature of the optical sensor 152 may be measured for a brief period of time, e.g., 100 ms, and then an optical measurement may be obtained without any illumination of the sample in the optical measurement chamber 146, e.g., for a 100 ms period. The temperature reading may be used to assist in calibrating the output of the optical sensor 152, if necessary (for example, photosensor output voltage may depend on both photosensor temperature and the amount of light that is detected). Subsequent to such a "dark" reading, a "light" reading may be obtained, e.g., one in which the sample is illuminated by the optical source that is used. Again, this may be for a period of time, e.g., 100 ms. The "dark" reading, e.g., the average "dark" reading, may be subtracted from the "light" reading, e.g., the average "light" reading, in order to compensate for any noise-related effects that may affect the results.

In this example, the first calibration sample is a true negative sample, i.e., there is no THC present (and thus no adduct will be formed). Thus, the optical measurement will generally result in a reading of zero, although there may be some low-level luminescence at the frequencies of interest due, for example, to potential contaminants or other sources of light in the sample solution. If present, these low-level luminescence readings may serve as a baseline of what a "zero" reading should correspond to.

Figure 16:
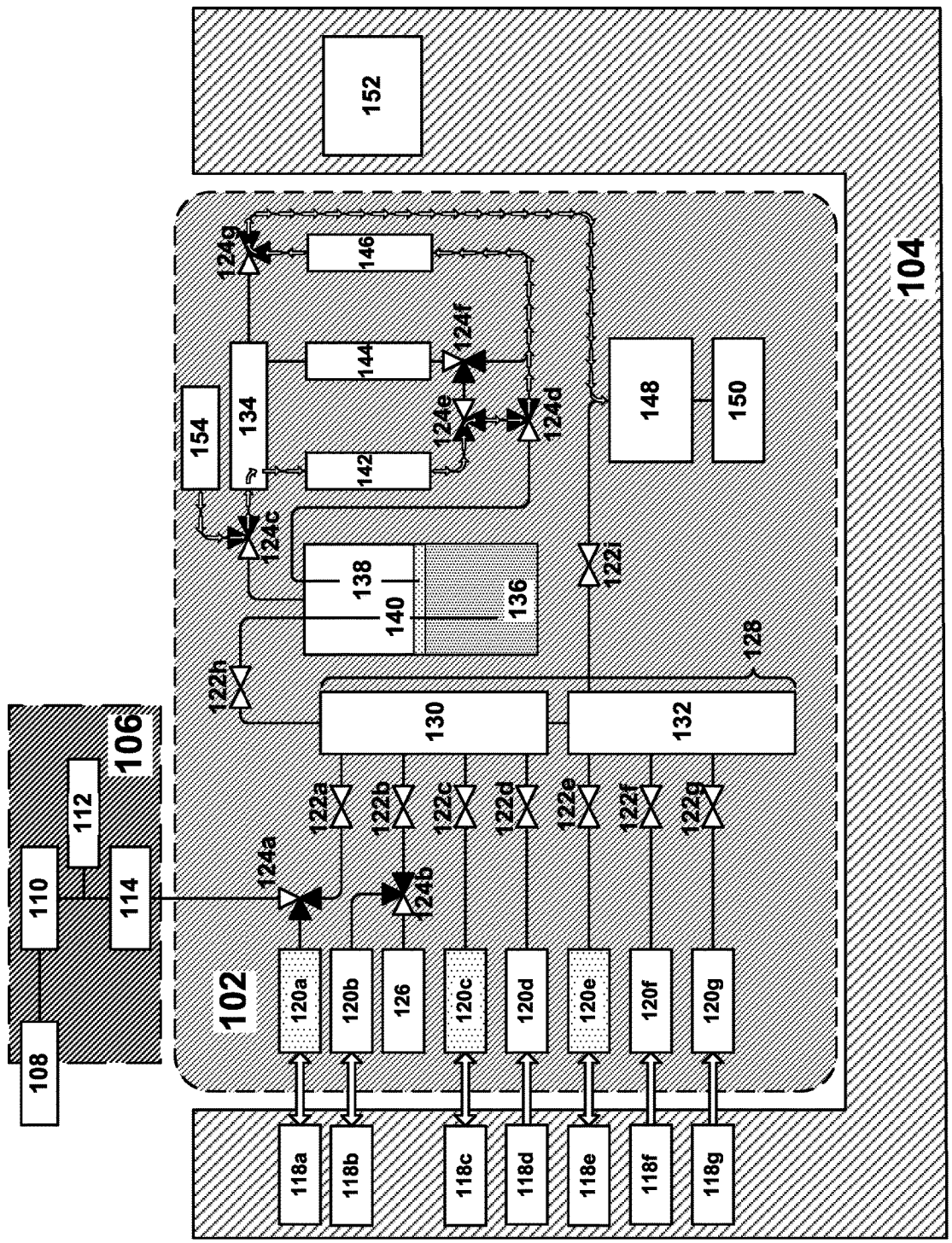
FIG. 16 depicts the example target substance analysis system of FIG. 1 during purging of the optical measurement chamber.
Figure 17:
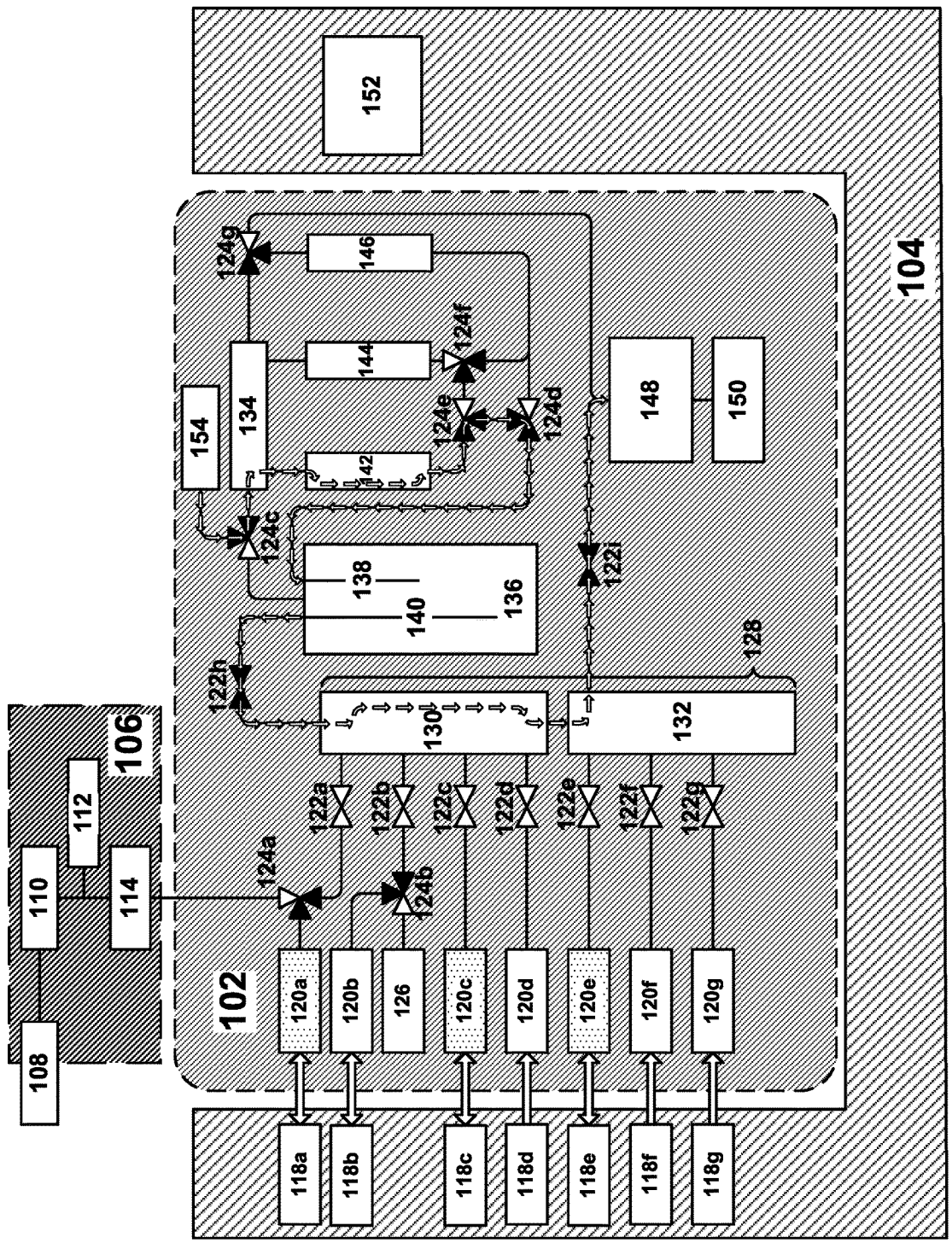
FIG. 17 depicts the example target substance analysis system of FIG. 1 during purging of another portion of the analysis system.

After the optical measurement has been obtained, the measured first calibration sample may be delivered from the optical measurement chamber 146 to a waste reservoir 148, as shown in FIG. 16. In this particular implementation, such a purge operation may be performed by adjusting 3-way valves 124c, 124d, and 124e such that the air pump 154 is in fluidic communication with the optical measurement chamber 146. Once such a fluidic connection has been made, the air pump 154 may be actuated so as to apply positive pressure to the optical measurement chamber 146, thereby driving the first calibration sample out of the optical measurement chamber 146 and into the waste reservoir 148. After the optical measurement chamber 146 has been purged, the mixing chamber 136 and the manifold 128 may be purged in a similar manner, such as is shown in FIG. 17. In this case, the three-way valve 124d may be actuated so as to divert air flow from the air pump 154 to the mixing chamber 136 via the short siphon 138, and the manifold valve 122h and a manifold waste valve 122i may be actuated so as to place the mixing chamber 136 in fluidic communication with the waste reservoir 148. The resulting air pressure may force the fluids in the mixing chamber 136 into the long siphon 140, thereby driving such fluids back through the manifold 128 and into the waste reservoir 148; a vent 150 may allow the air that is used for such purposes to escape while keeping the used sample in the waste reservoir 148.

After the first calibration sample solution has been purged from the optical measurement chamber 146, the manifold 128, the mixing chamber 136, the optical measurement chamber 146, and any other components that came into contact with the first calibration sample may be washed with a cleaning agent delivered from a cleaning agent reservoir 120g. Such cleaning may be accomplished by opening a cleaning agent valve 122g and then driving a cleaning agent out of the cleaning agent reservoir 120g using a cleaning agent actuator 118g. The various valves in the analysis system 100 may be actuated so as to route the cleaning agent through the various components with which the first calibration sample came into contact and then ultimately to the waste reservoir. Such routing may be similar to the manner in which the air from the air pump 154 was routed through the analysis system 100, e.g., such as depicted in FIGS. 16 and 17. After the cleaning agent is routed through the analysis system 100, the cleaned components of the analysis system 100 may be dried by flowing air from the air pump 154 along the same flow paths.

This same process, e.g., the steps depicted in FIGS. 10 through 17 (and the purge and cleaning steps), may be repeated, with some slight differences, for the eluted breath constituent sample and well as for the second calibration sample. Such further processing is discussed below.

Figure 18:
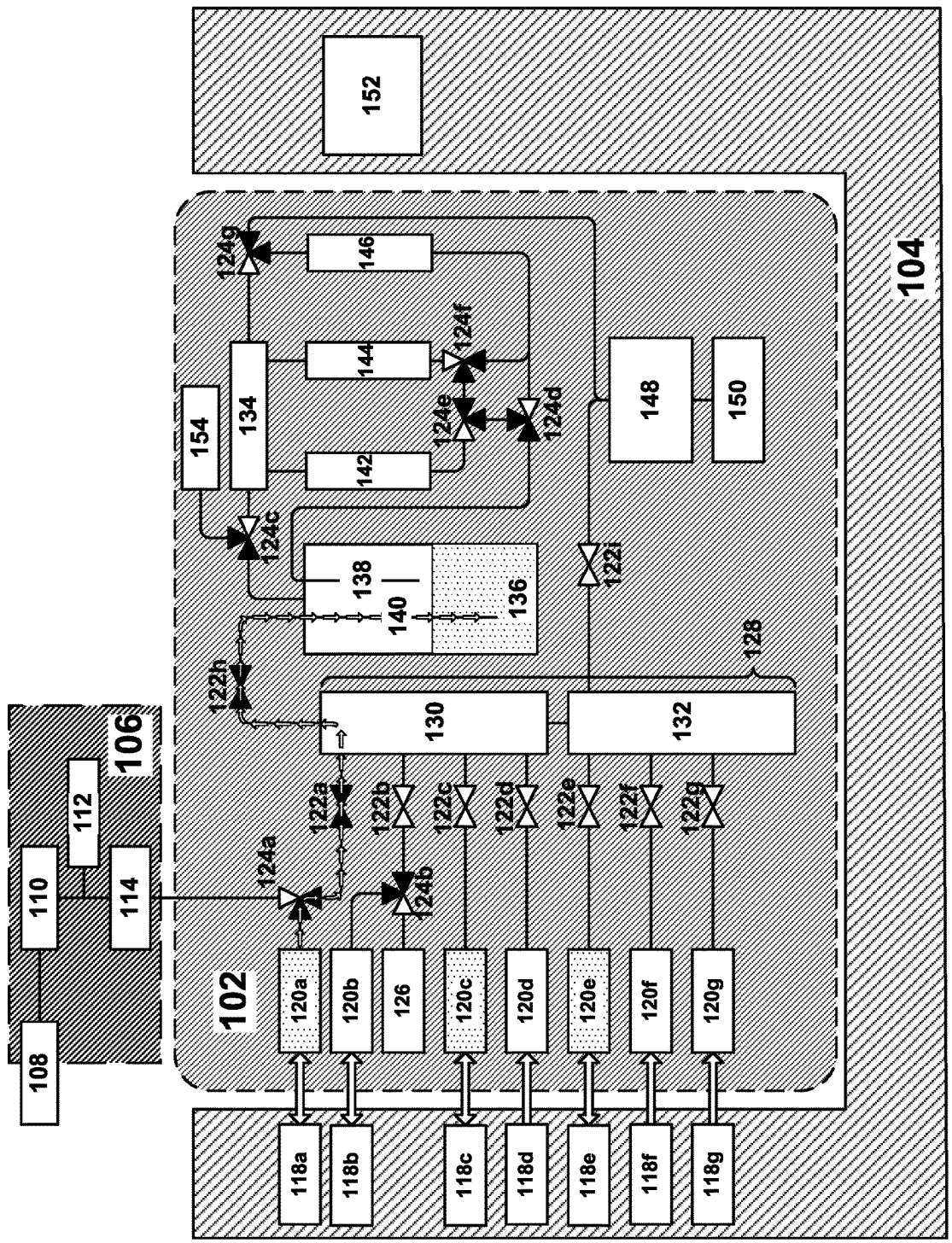
FIG. 18 depicts the example target substance analysis system of FIG. 1 during delivery of the combined indicator and sample to the mixing chamber.

After the optical measurement chamber 146 and the mixing chamber 136 are cleaned, the combined eluted breath constituent sample and liquid indicator may be delivered to the mixing chamber 136 from the sample reservoir 120a, e.g., by opening the sample valve 122a and the manifold valve 122h and actuating the sample actuator 118a (with the 3-way valve 124a actuated so as to place the sample reservoir 120a and the manifold 128 into fluidic communication. Thus, the combined eluted breath constituent sample and liquid indicator may be delivered to the mixing chamber 136, as shown in FIG. 18.

Figure 19:
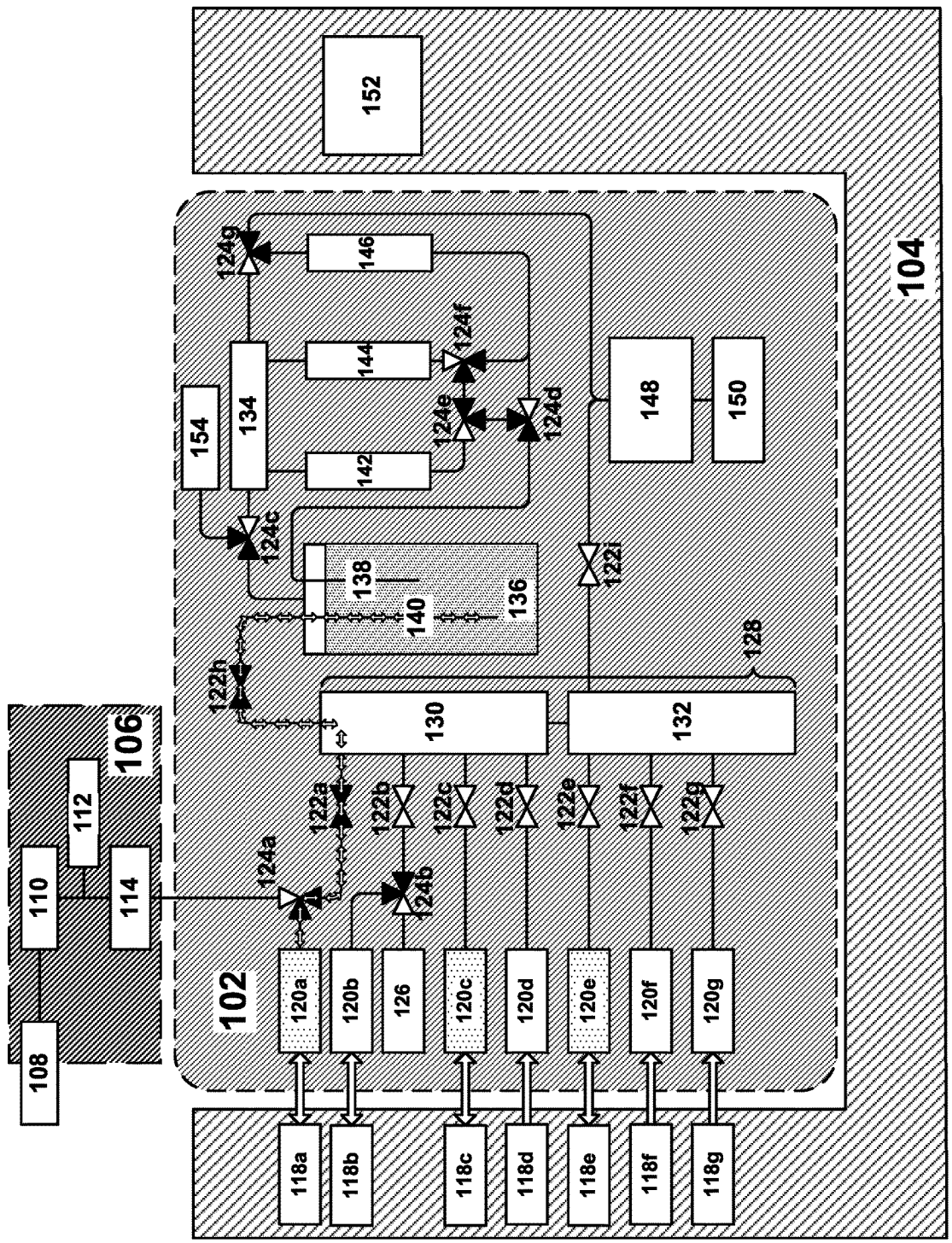
FIG. 19 depicts the example target substance analysis system of FIG. 1 during mixing of solvent and the combined indicator and sample.

Once the combined eluted breath constituent sample and liquid indicator have been delivered to the mixing chamber 136, the solvent from the solvent reservoir 120f may be delivered to the mixing chamber, essentially repeating the process depicted in FIG. 11. Once the solvent has been delivered to the mixing chamber 136, the solvent and the combined eluted breath constituent sample and liquid indicator may be mixed by reciprocating the sample actuator 118a to repeatedly draw the fluid in the mixing chamber 136 in and out of the sample reservoir 120a as shown in FIG. 19, similar to how the first calibration sample was mixed in FIG. 12.

Figure 20:
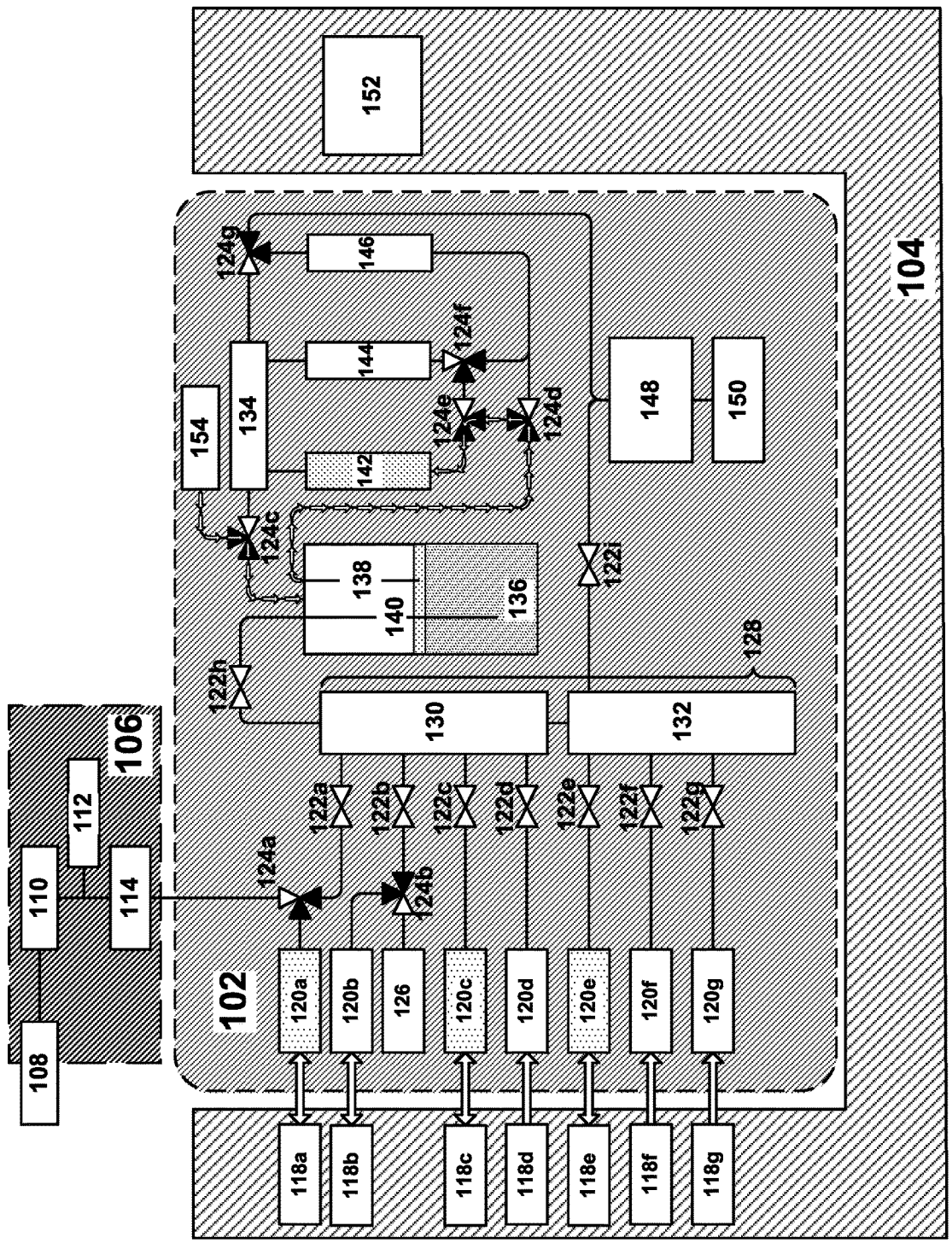
FIG. 20 depicts the example target substance analysis system of FIG. 1 during delivery of a separation layer from the mixing chamber to a first activation cell.

Once the mixing of the solvent and the combined eluted breath constituent sample and liquid indicator has been completed, the mixture may be allowed to separate, similar to the separation depicted in FIG. 13. Once the mixture has separated, the sample THC adduct may be siphoned off through the short siphon 138, e.g., by pressurizing the mixing chamber using the air pump 154. The valves 124d and 124e may be actuated such that the sample THC adduct is conveyed to the first activation cell 142, as shown in FIG. 20. The first activation cell 142 may be configured to activate the sample THC adduct, i.e., cause the THC adduct to transition to a state in which it is photo-reactive so that it will luminesce when stimulated with a particular wavelength or wavelengths of light. In some implementations, the first activation cell 142 may be coated with a hydrophobic coating or other coating that interacts with the sample THC adduct in order to activate it. In some implementations, the first activation cell may be a pipette tip produced using StarLab International GmbH's REPEL POLYMER TECHNOLOGY (RPT), (examples of such pipette tips are, for example, the "TIPONE® RPT" sold by USA Scientific, and, more specifically, the 1000 µL XL TIPONE® RPT, part number 1182-1830), which may be used to produce an optimized conventional polypropylene surface that is extremely hydrophobic; such pipettes have been tested and have proven to be effective at activating THC adducts such as rhodamine-123, as compared with other types of pipette tips that are not able to activate rhodamine-123. In some implementations, there may be one activation cell for each sample that has or may have THC in it, as the process of activating the THC adduct in a given sample may consume the coating or other catalyst that causes the activation.

Figure 21:
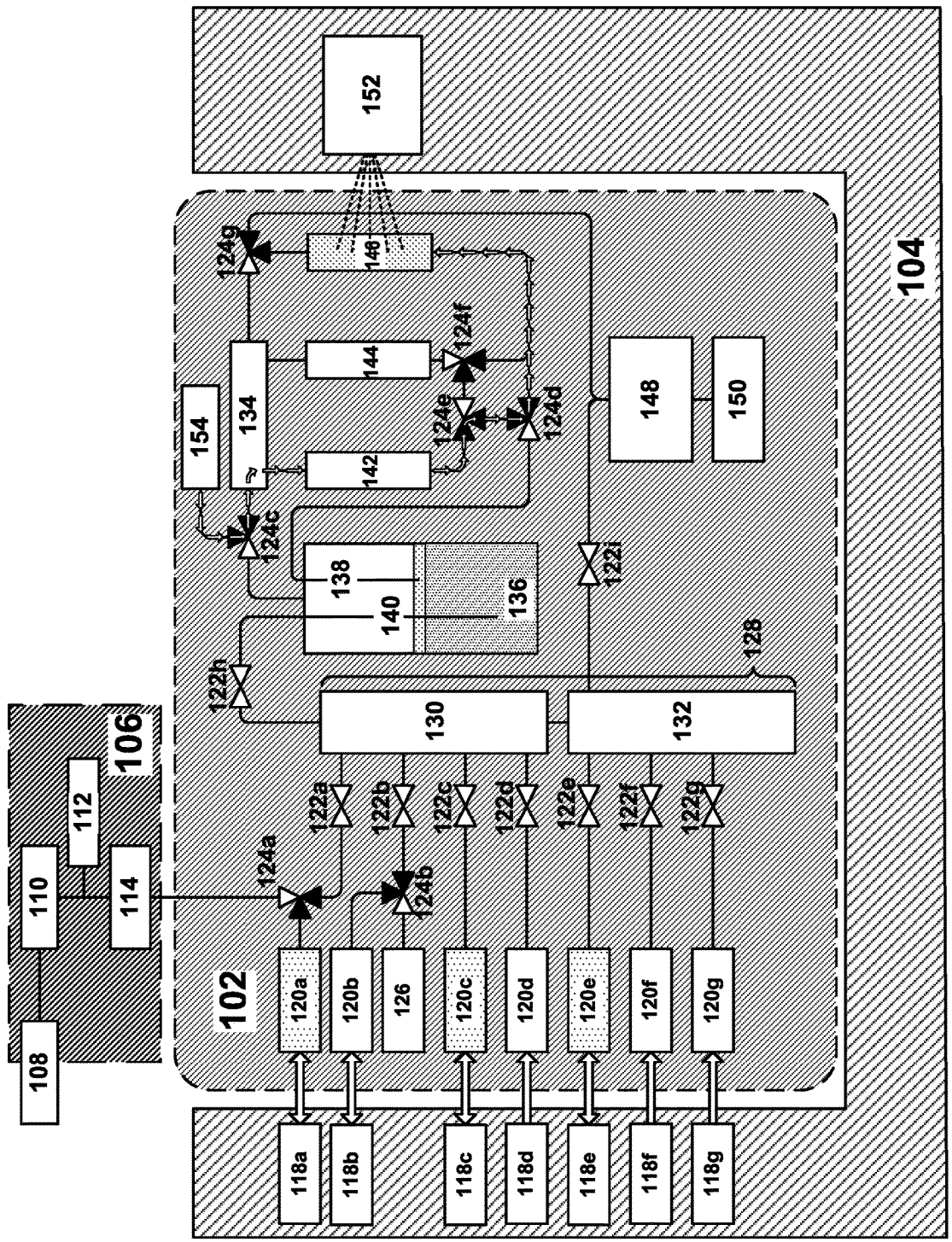
FIG. 21 depicts the example target substance analysis system of FIG. 1 during delivery of the separation layer in the first activation cell to the optical measurement chamber.

After the sample THC adduct has been activated in the first activation cell 142, the 3-way valve 124c may be actuated to put the air pump 154 in fluidic communication with the first activation cell 142 via a pneumatic manifold 134, and the 3-way valves 124e and 124d may be actuated so as to put the first activation cell 142 into fluidic communication with the optical measurement chamber 146. The sample THC adduct may then be driven out of the first activation cell 142 by air from the air pump 154, as shown in FIG. 21, and into the optical measurement cell 146. Once the sample THC adduct is in the optical measurement cell 146, a measurement of the amount of THC adduct that is within the optical measurement cell 146 may be obtained in the same manner as described above with respect to FIG. 15, and then the analysis system 100 may be purged and cleaned, as discussed above with respect to FIGS. 16 and 17, and cleaned and dried, as also discussed above.

After the sample THC adduct has been measured and routed to the waste reservoir 148, the second calibration sample may be analyzed. Such analysis may begin with the delivery of the second calibration sample to the mixing chamber 136. For example, a second calibration sample valve 122e may be opened and the second calibration sample actuator 118e may be actuated to drive the combined second calibration sample and liquid indicator into the mixing chamber via the long siphon 140.

Figure 22:
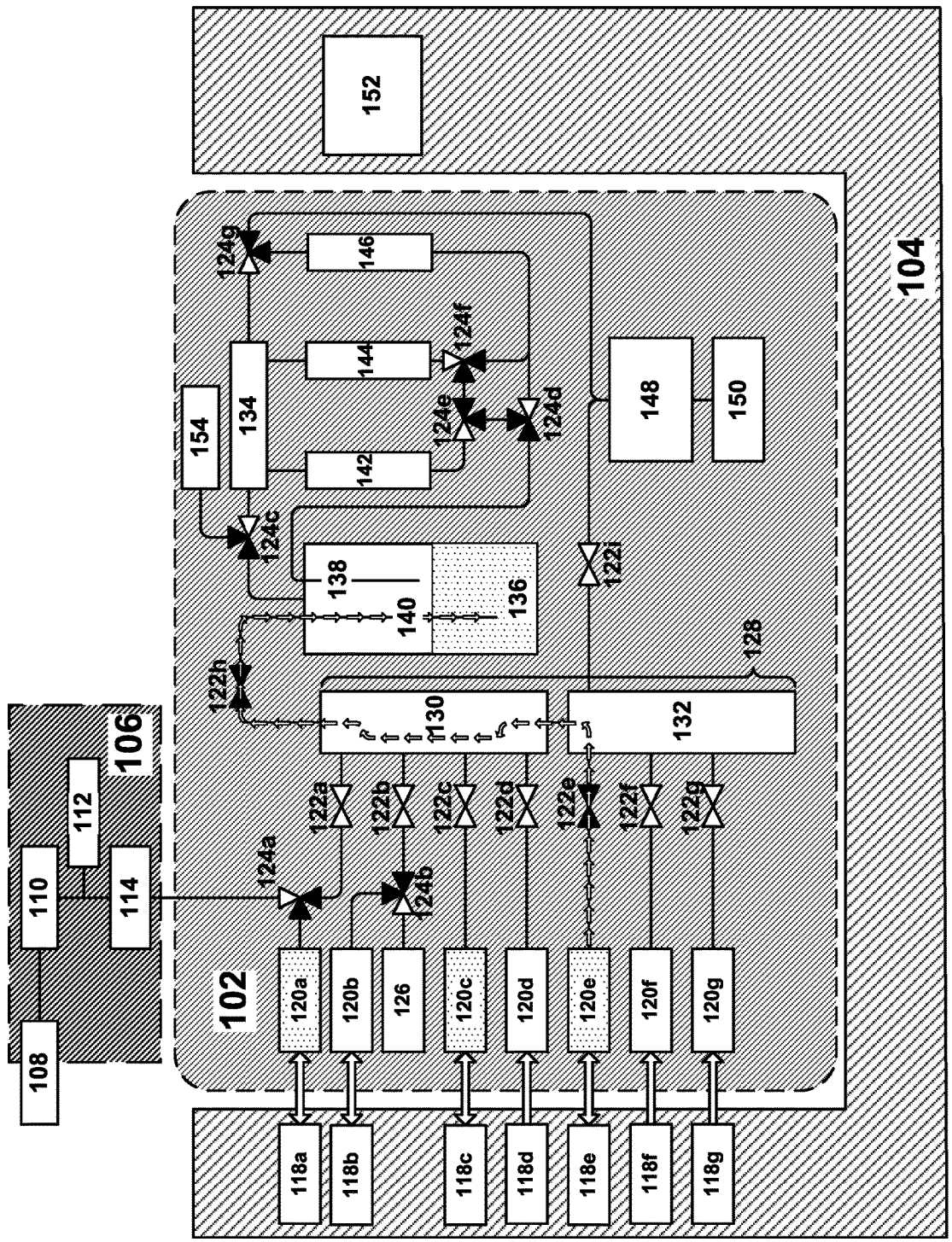
FIG. 22 depicts the example target substance analysis system of FIG. 1 during delivery of the combined indicator and the second calibration sample to the mixing chamber.
Figure 23:
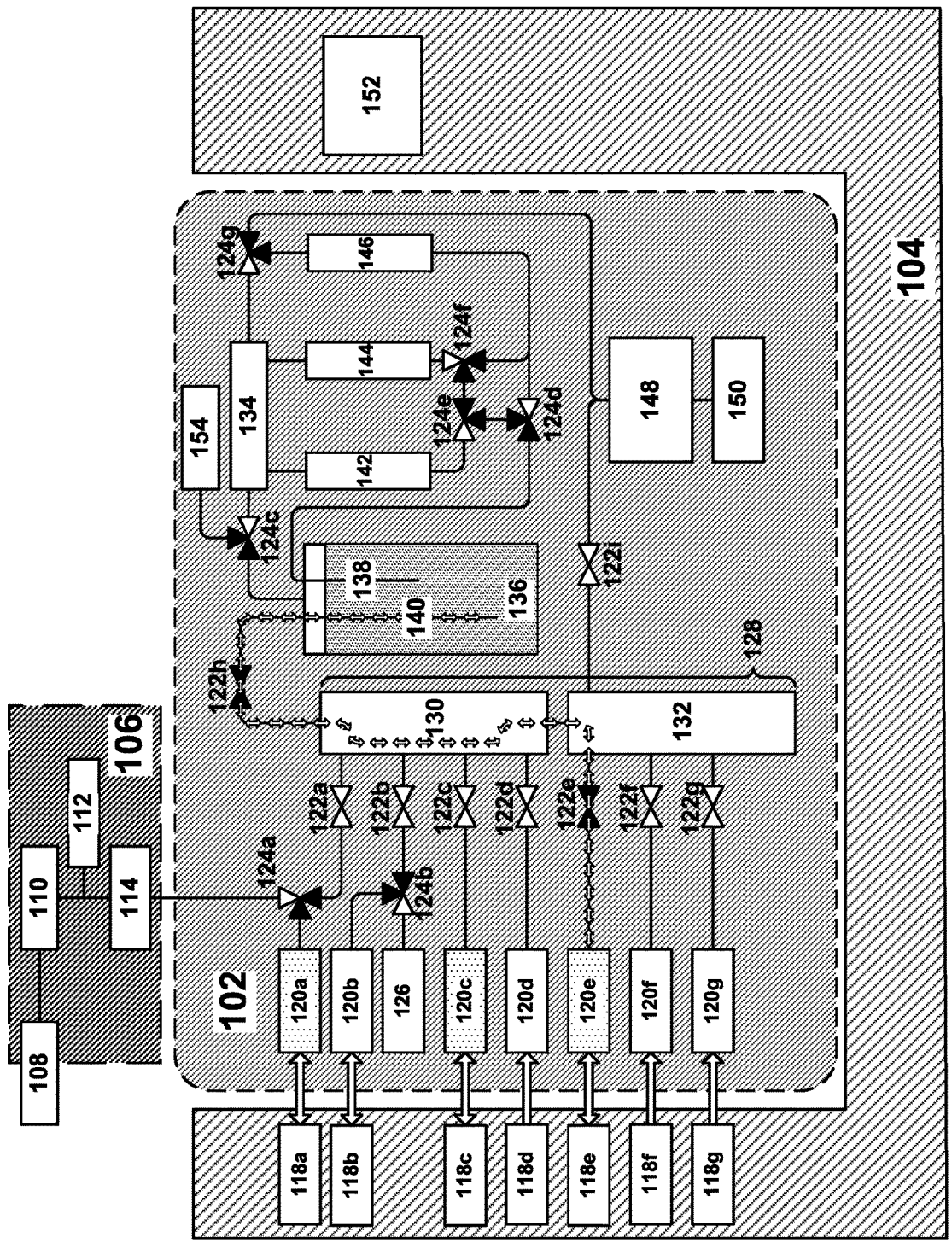
FIG. 23 depicts the example target substance analysis system of FIG. 1 during mixing of solvent and the combined indicator and second calibration sample.

Once the combined second calibration sample and liquid indicator have been delivered to the mixing chamber 136, the solvent from the solvent reservoir 120f may be delivered to the mixing chamber as shown in FIG. 22, essentially repeating the process depicted in FIG. 11. Once the solvent has been delivered to the mixing chamber 136, the solvent and the combined second calibration sample and liquid indicator may be mixed, as shown in FIG. 23 by reciprocating the second calibration sample actuator 118e to repeatedly draw the fluid in the mixing chamber 136 in and out of the second calibration sample reservoir 120a, similar to how the first calibration sample was mixed in FIG. 12.

Figure 24:
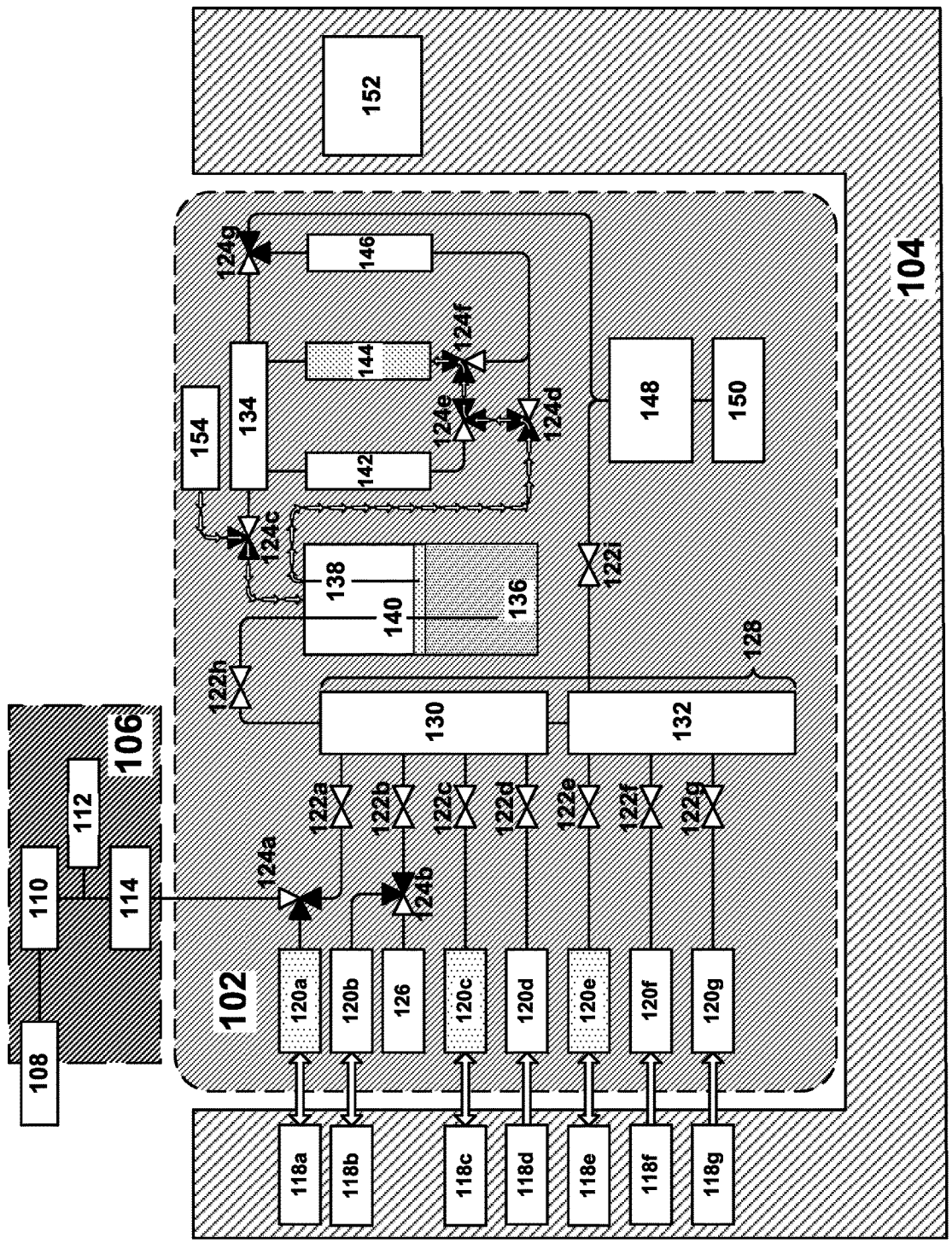
FIG. 24 depicts the example target substance analysis system of FIG. 1 during delivery of a separation layer from the mixing chamber to a second activation cell.

Once the mixing of the solvent and the combined second calibration sample and liquid indicator has been completed, the mixture may be allowed to separate, similar to the separation depicted in FIG. 13. Once the mixture has separated, the second calibration sample THC adduct may be siphoned off through the short siphon 138, e.g., by pressurizing the mixing chamber 136 using the air pump 154. The valves 124d, 124e, and 124f may be actuated such that the second calibration sample THC adduct is conveyed to the second activation cell 144, as shown in FIG. 24. The second activation cell 144 may be similar to the first activation cell 142 and serve a similar purpose, but with respect to the second calibration sample adduct, i.e., it may be used to activate the second calibration sample adduct.

Figure 25:
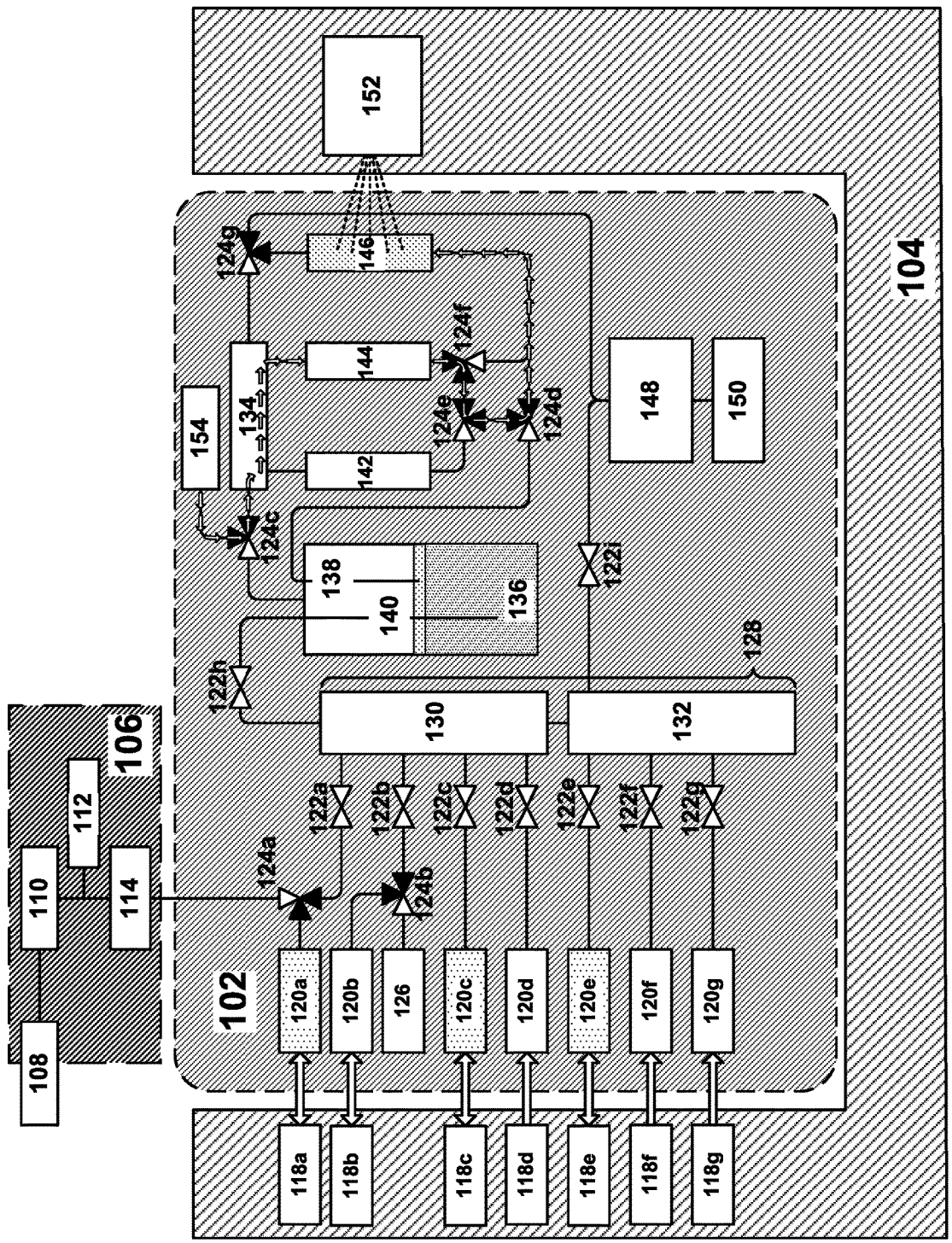
FIG. 25 depicts the example target substance analysis system of FIG. 1 during delivery of the separation layer in the second activation cell to the optical measurement chamber.

After the second calibration sample THC adduct has been activated in the second activation cell 144, the 3-way valve 124c may be actuated to put the air pump 154 in fluidic communication with the first activation cell 142 via a pneumatic manifold 134, and the 3-way valves 124f, 124e, and 124d may be actuated so as to put the second activation cell 144 into fluidic communication with the optical measurement chamber 146. The second calibration sample THC adduct may then be driven out of the second activation cell 144 by air from the air pump 154, as shown in FIG. 25, and into the optical measurement cell 146. Once the second calibration sample THC adduct is in the optical measurement cell 146, a measurement of the amount of THC adduct that is within the optical measurement cell 146 may be obtained in the same manner as described above with respect to FIG. 15, and then the analysis system 100 may be purged and cleaned, as discussed above with respect to FIGS. 16 and 17, and cleaned and dried, as also discussed above.

Figure 26:
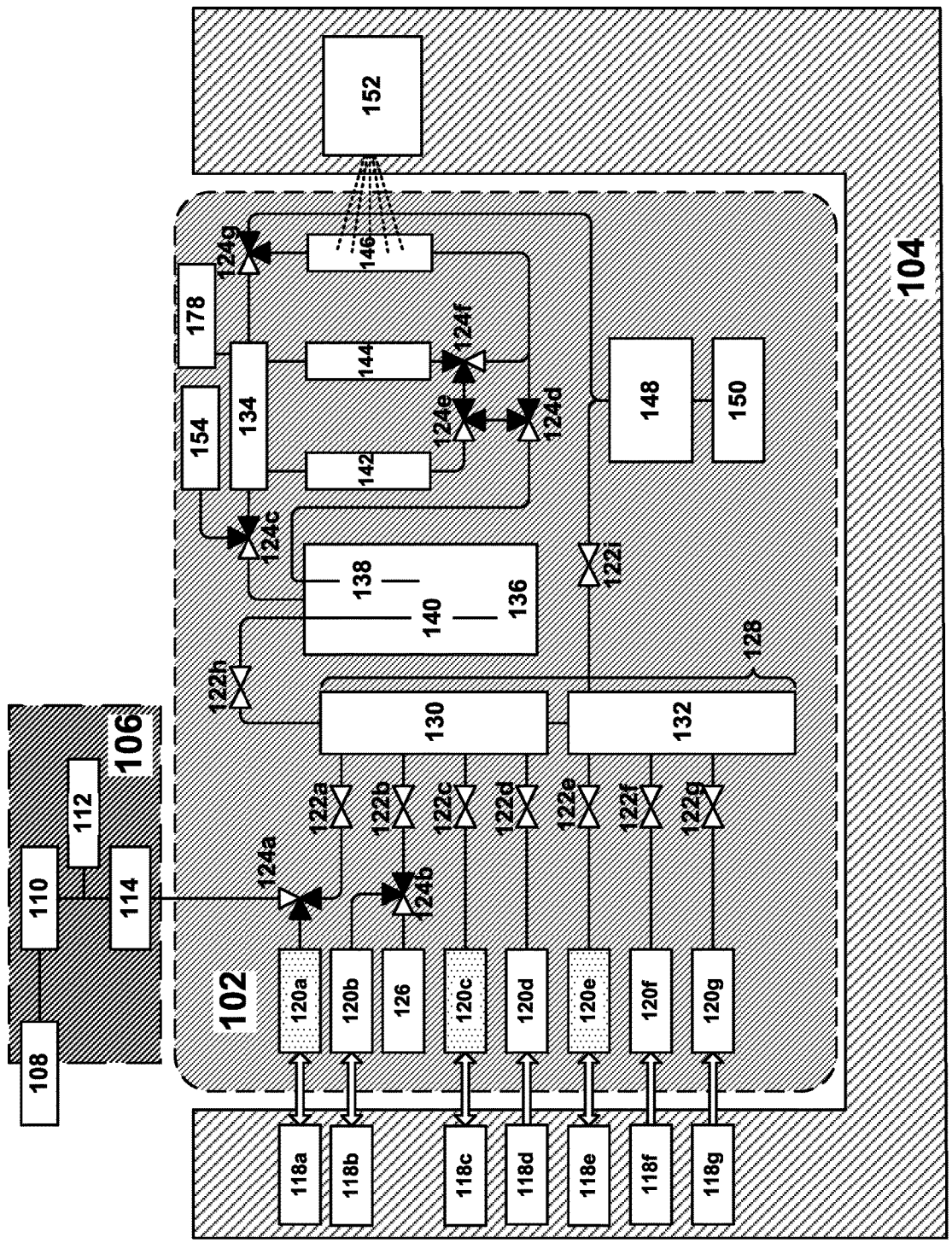
FIG. 26 depicts a variant of the target substance analysis system of FIG. 1.

FIG. 26 depicts a variant of the target substance analysis system of FIG. 1. In FIG. 26, a pressure relief valve 178 has been added to the pneumatic manifold 134 to allow pressure that may build up in the activation cells 142 or 144 to be relieved. Such a pressure valve may, for example, activate to release excess pressure when the pressure in the pneumatic manifold 134 exceeds 3 psi above ambient levels.

FIGS. 27 through 37 show various example views of an analysis system, or components thereof, that may be used in the manner described above with respect to FIGS. 1 through 24. For ease of reference, the components in FIGS. 27 through 37 that correspond to components in FIGS. 1 through 24 are identified by reference numbers having the same last two digits as the corresponding components or element in FIGS. 1 through 24.

Figure 27:
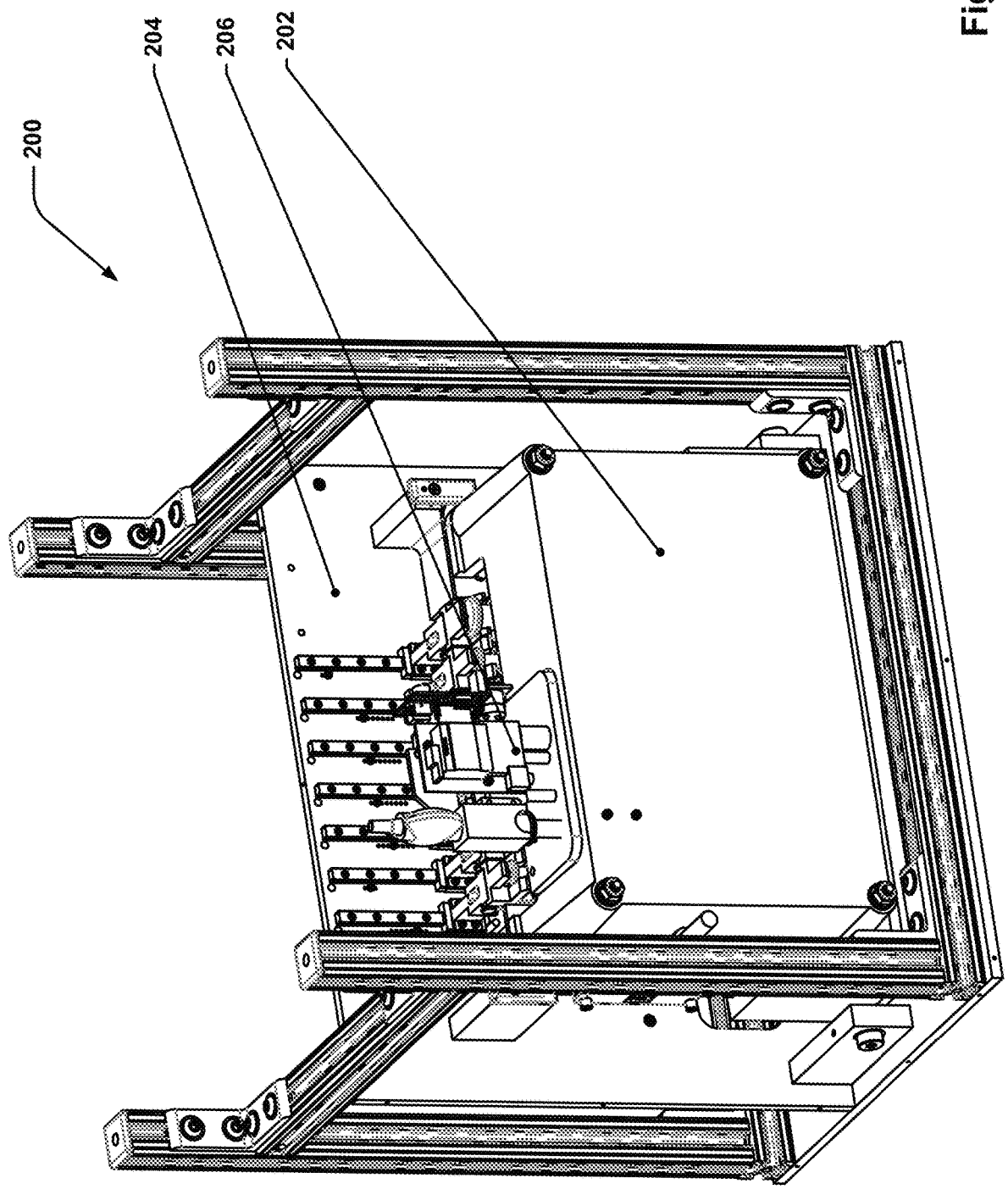
FIG. 27 depicts an isometric view of an example target substance analysis system.

FIG. 27 depicts an isometric view of an example target substance analysis system. The analysis system 200 may include, for example, three separate modules—a base station 204, a cartridge 202, and a handheld breath capture module (BCM) 206. The analysis system may have an exterior housing (not shown) that covers and protects the internal components during use.

Figure 28:
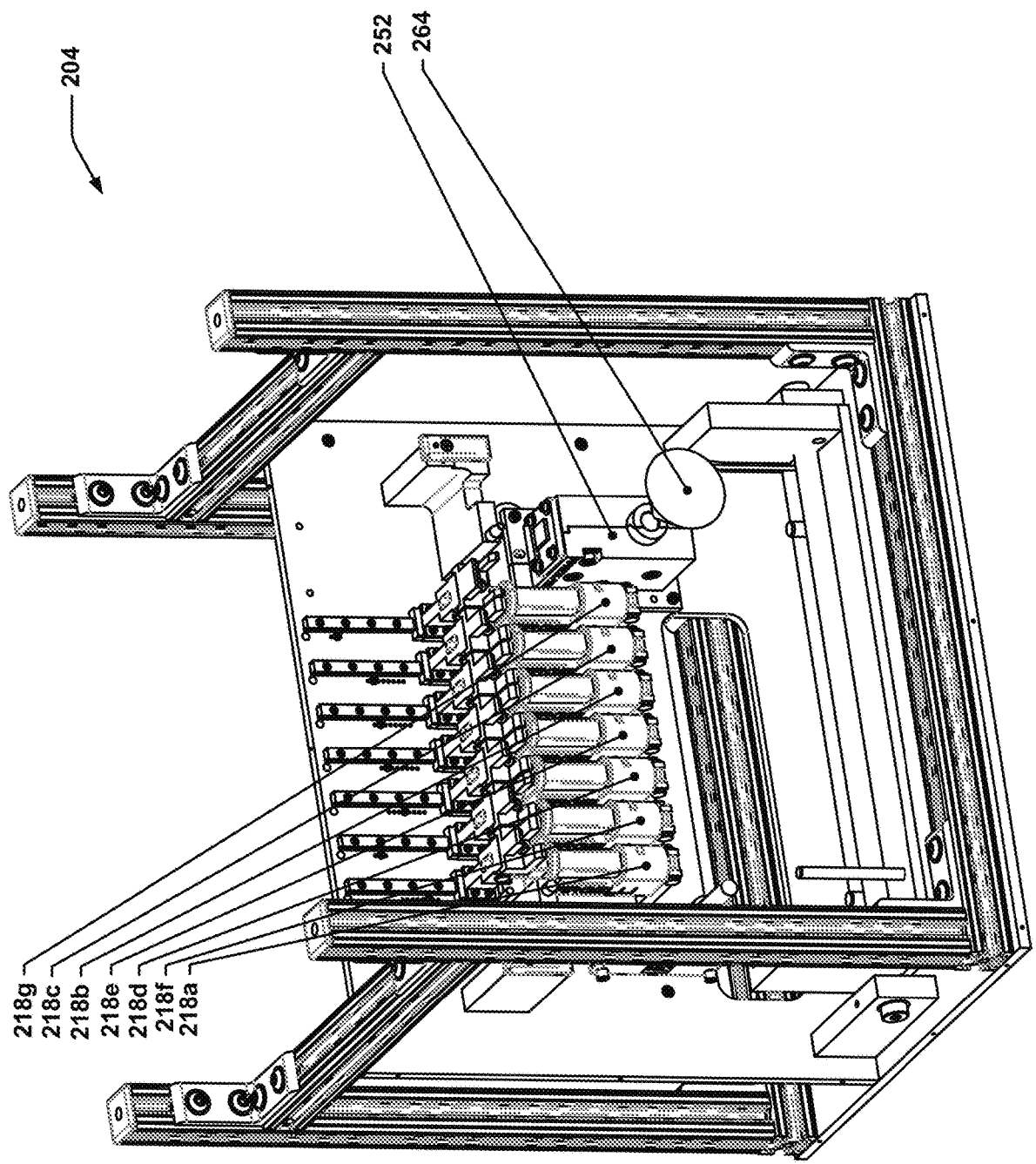
FIG. 28 depicts a base station of the example target substance analysis system without a cartridge or handheld breath collector module installed.

FIG. 28 depicts the base station 204 without the cartridge 202 or the handheld BCM 206 installed. As can be seen, the base station may include multiple actuators, such as actuators 218a through 218g, which may be used to control how fluids are dispensed from or drawn into the reservoirs that are included in the cartridge 202. In the cartridge 202, the reservoirs that are included are provided in the form of syringes; when the cartridge 202 is installed in the base station 204, each actuator 218 may interface with a plunger of a corresponding syringe and may be actuated so as to move the plunger into or out of the syringe, thus causing fluids to be driven from or sucked into the syringe/reservoir.

Figure 29:
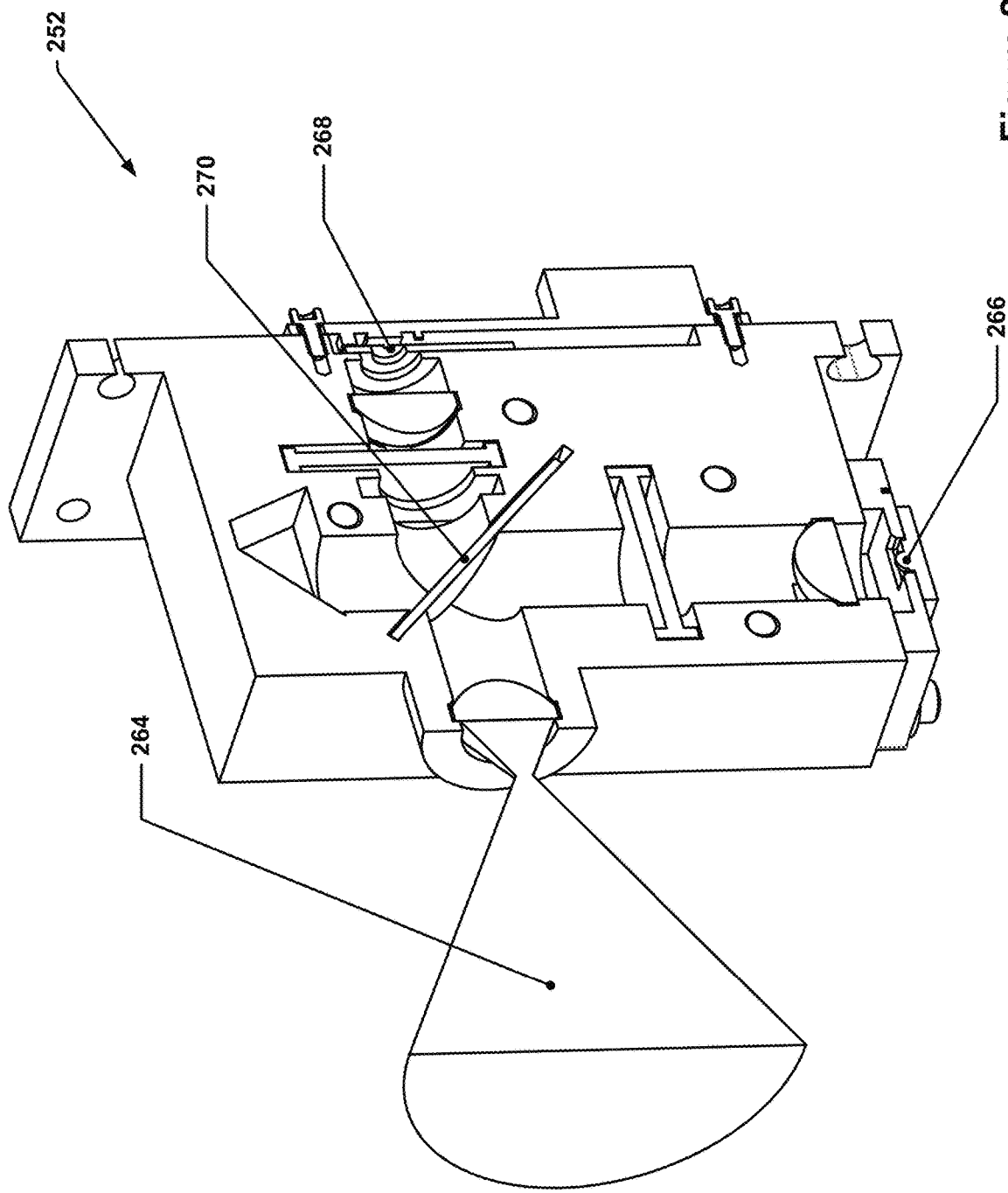
FIG. 29 depicts an isometric cutaway view of an example optical measurement sensor.

The base station may also include an optical measurement sensor 252 that may be configured to obtain luminescence readings from samples that are processed in the cartridge 202. The optical measurement sensor 252, in this implementations, projects an optical beam 264 having a first wavelength range that is selected so as to stimulate emission of light having a second wavelength range from the THC adduct. The emitted light may then be collected by the same optics used for projection and routed to a photodetector in the optical measurement sensor 252 for quantification. FIG. 29 depicts an isometric cutaway view of an example optical measurement sensor 252. A photoemitter 266 may be located so as to direct light along a first axis (the vertical axis with respect to the orientation of FIG. 29), and a photodetector 268 may be configured to receive light received along a second axis that is orthogonal to the first axis. A beam splitter 270, e.g., a window that is generally reflective to the first wavelength range but generally transmissive to the second wavelength range, may be located at the intersection of the first axis and the second axis, and may be positioned at a 45° angle to both axes so as to cause light from the photoemitter 266 to be turned 90° and directed out of the optical measurement sensor 252 to form the optical beam 264. At the same time, light that is emitted by the THC adduct in response to stimulation by the light of the first wavelength range may pass through the beam splitter 270 without being reflected and thus be received by the photodetector 268. When measurement of the amount of THC adduct present in a sample is desired, the photoemitter 266 may be turned on so that light of the first wavelength range is emitted to optically pump or stimulate the THC adduct; the light of the second wavelength range that is emitted by the THC adduct in response may then be measured by the photodetector 268, and the intensity of such detected light may be correlated with an amount or concentration of THC adduct (and thus THC) that is present in the sample.

It is to be understood that other types of optical sensors may be used as well, and that some optical sensors may, depending on the particular adduct used, not include a photoemitter, e.g., in implementations where the THC adduct does not require optical pumping in order to emit light.

Figure 30:
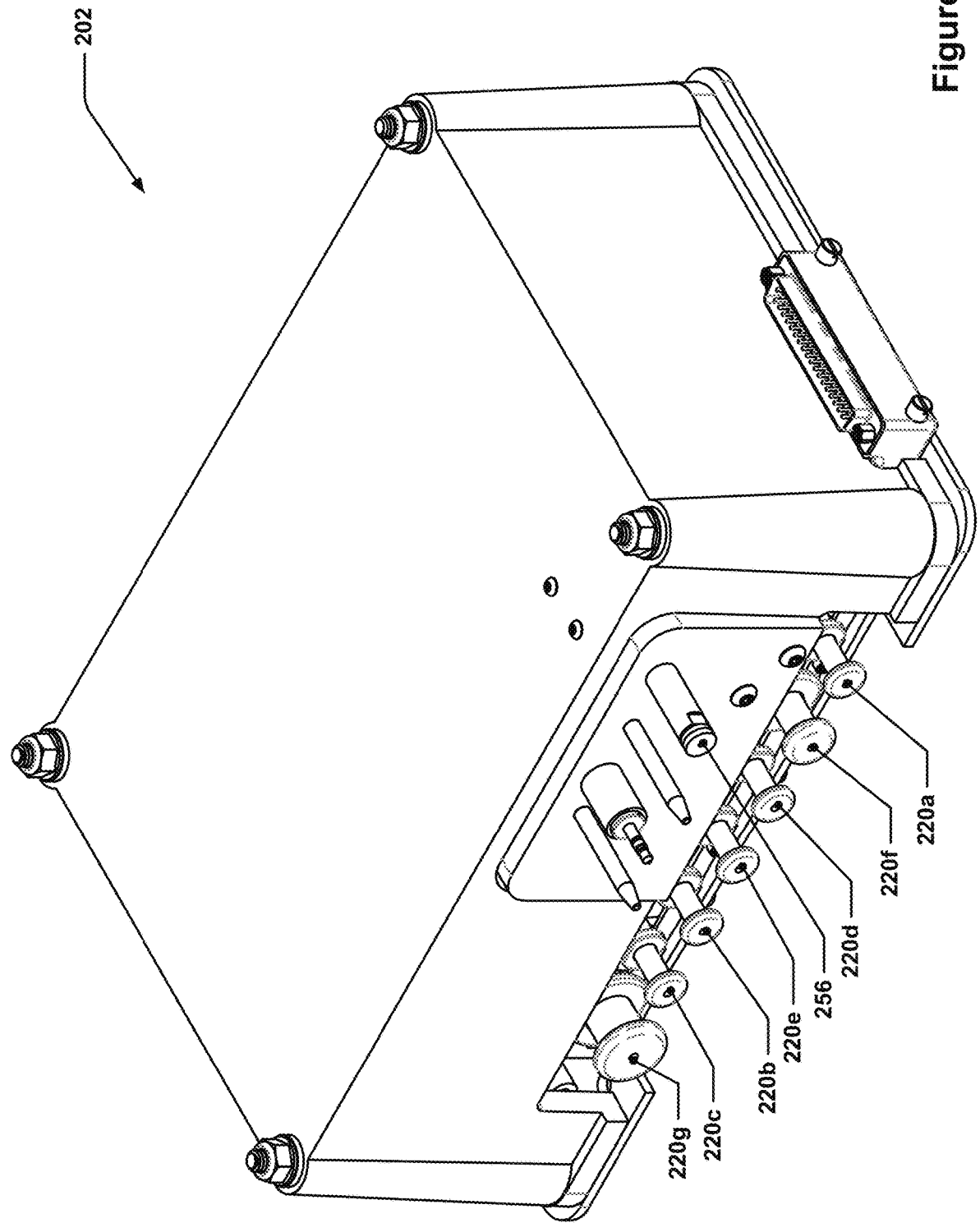
FIG. 30 depicts an example cartridge.

FIG. 30 depicts an example cartridge 202; the cartridge may have a protective cover (as depicted) and house within it most or all of the "wet" chemistry components that are used in the analysis process. In addition to reservoirs 220a through 220g, the cartridge 202 may also include an elution port 256 that may connect with a catch media of the handheld BCM 206. The cartridge 202 may also have mechanical features and electrical connections for interfacing the cartridge 202 with the base station 204 and with the handheld BCM 206.

Figure 31:
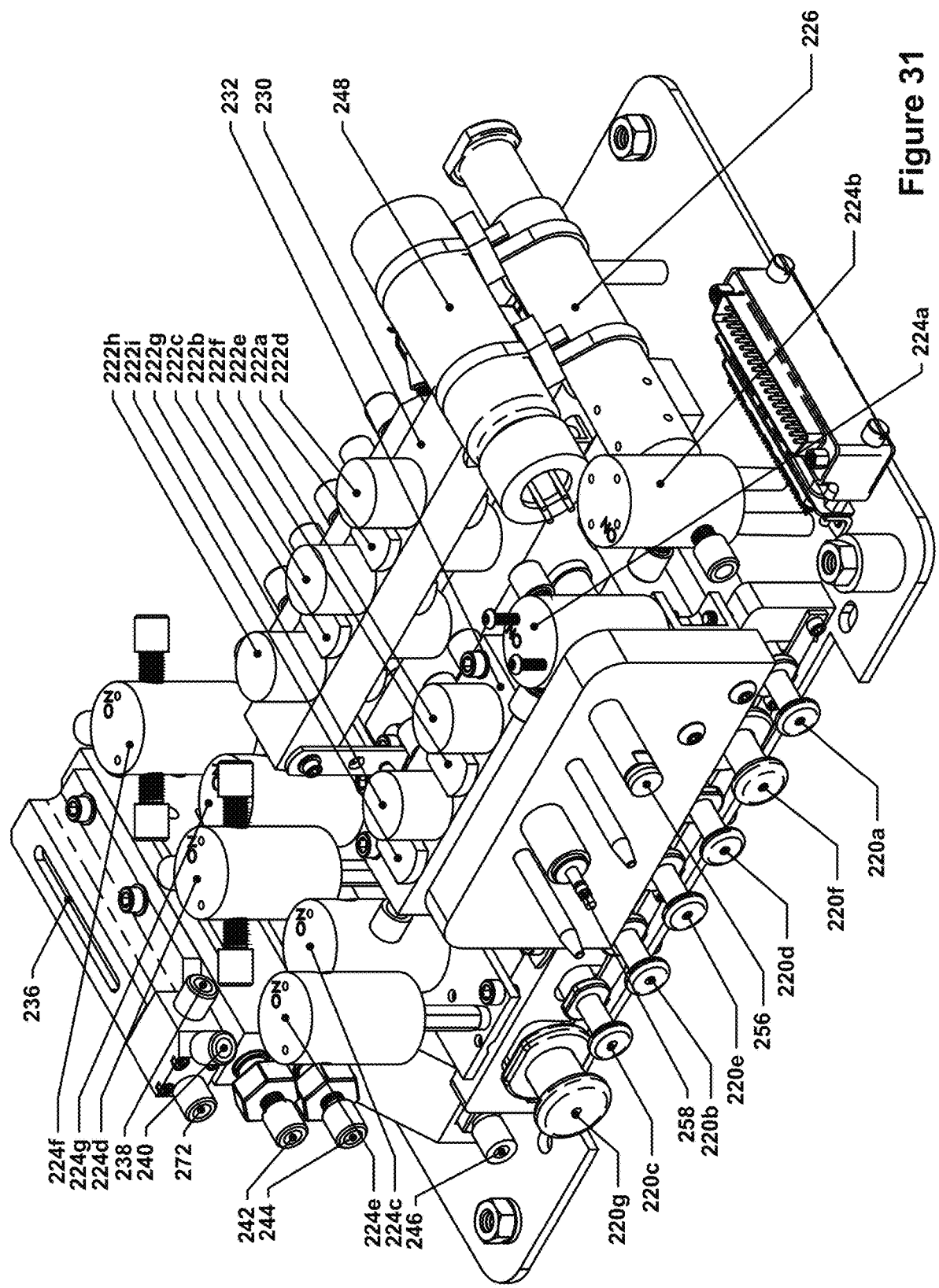
FIG. 31 depicts the example cartridge of FIG. 30 with the cover removed to allow the internal components to be more clearly seen.
Figure 32:
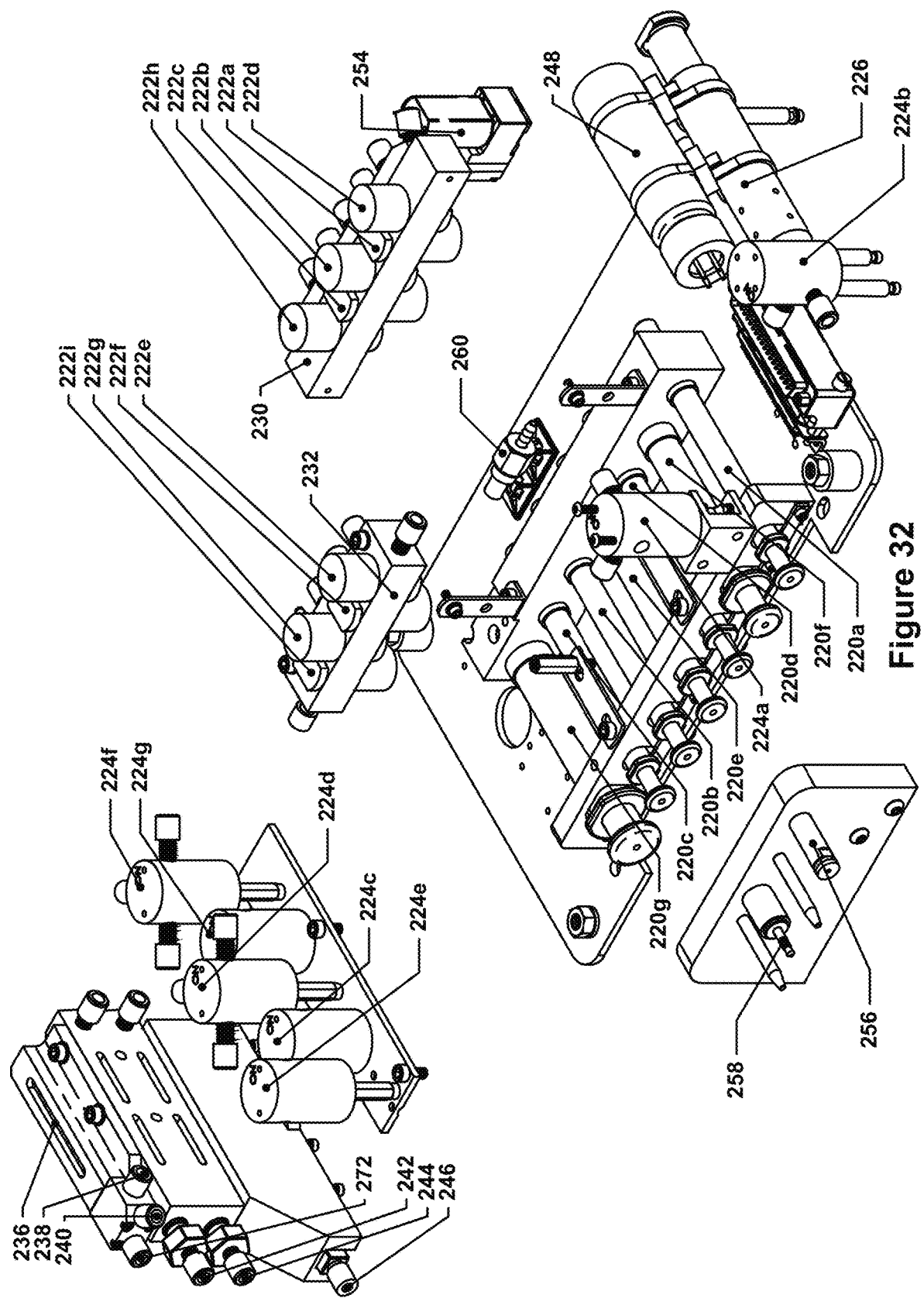
FIG. 32 depicts the same uncovered view of the example cartridge of FIG. 30, but with various subassemblies exploded to allow for clearer viewing.

FIG. 31 depicts the example cartridge 202 with the cover removed to allow the internal components to be more clearly seen. FIG. 32 depicts the same uncovered view of the example cartridge 202, but with various subassemblies exploded to allow for clearer viewing. It is to be understood that the components depicted and described below may be connected together by flexible tubing that provides fluidic connections between the various ports of the components depicted. Such tubing is not depicted in these Figures since the number of tubes and the routing of the tubes would clutter the Figures and impact their clarity. However, it is to be understood that the components depicted in FIGS. 31 and 32 are, in actual practice, connected by such tubing, and that such tubing routing/connections may be consistent with the fluidic connections and routing shown in FIG. 1.

In FIGS. 31 and 32, it may be seen that reservoirs 220 are arranged in a row and supported by a common interface block that positions each reservoir 220 in a particular position that allows each 220 to interface with a corresponding one of the actuators 218 when the cartridge 202 is installed in the base station 204. A sample reservoir 2020a, a solvent reservoir 2020f, a buffer reservoir 2020d, a second calibration sample reservoir 2020e, an indicator solvent reservoir 2020b, a first calibration sample reservoir 2020c, and a cleaning agent reservoir 2020g are depicted. It is to be understood that the order and relative positioning of these reservoirs may be different in various implementations, and that the particular placement of such reservoirs may be selected taking into account various considerations, such as minimization of tubing lengths (to reduce dead volumes), standardization of tubing lengths (to facilitate assembly), etc.

Also visible in FIGS. 31 and 32 are features for interfacing with the handheld BCM 206, e.g., the elution port 256, as well as an electrical interconnect 258 that may allow the cartridge 202 or the base station 204, via the cartridge 202, to communicate with the electronics of the handheld BCM 206.

In the implementation depicted in FIGS. 31 and 32, the valves 222 are integrated into the manifolds 230 and 232 (rather than being separate, as suggested in FIG. 1) to reduce the potential dead volume in the manifold that is formed by the two manifolds 230 and 232. Thus, the manifold 230 may include a buffer valve 222d, a sample valve 222a, an indicator solvent valve 222b, a first calibration sample valve 222c, and a manifold valve 222h. Correspondingly, the manifold 232 may include a second calibration sample valve 222e, a solvent valve 222f, a cleaning agent valve 222g, and a manifold waste valve 222i. 3-way valves 224a through 224g may also be included to allow fluid flow to be directed between two different end points (or be received from one of two sources).

The cartridge 202 may also include, for example, an indicator chamber 226 and a waste reservoir 248, as well as a mixing chamber 236, a first activation cell 242 (indicated by outlet port), a second activation cell 244 (indicated by outlet port), and an optical measurement chamber 246 (indicated by outlet port). The mixing chamber may have inlet ports for a short siphon 238, a long siphon 240, and a pressurization port 272.

Figure 34:
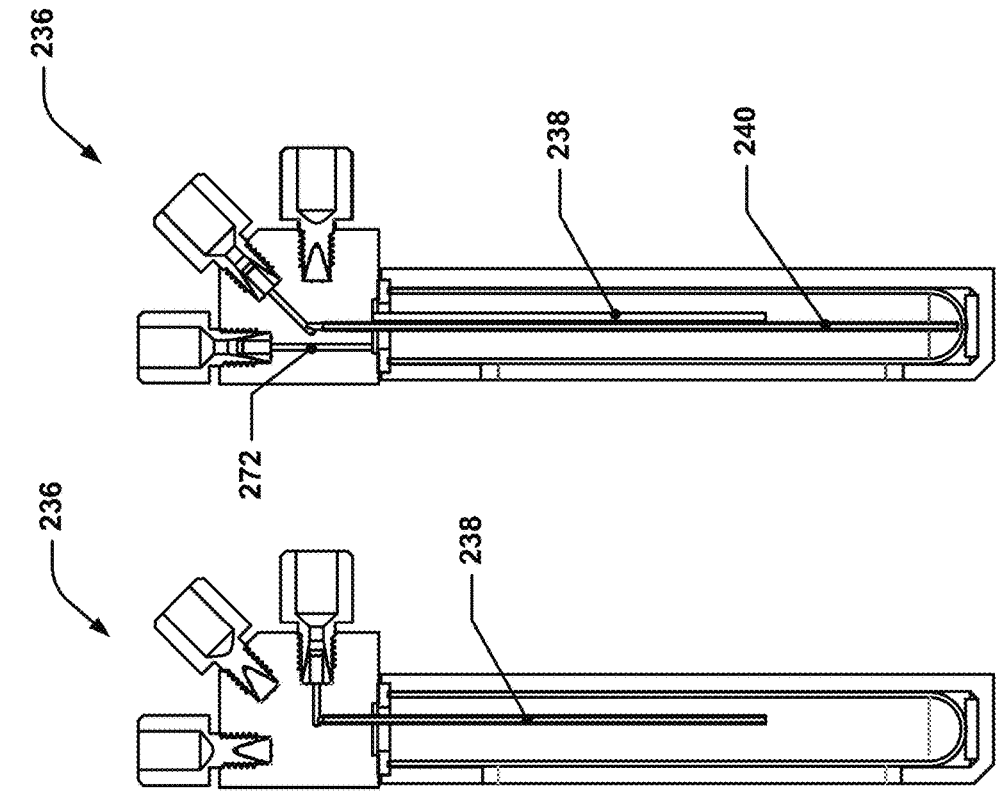
FIGS. 33 and 34 depict section views of an example mixing chamber.
Figure 33:
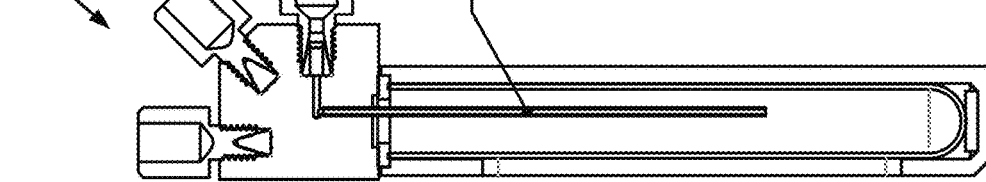

FIGS. 33 and 34 depict section views of the mixing chamber 236. As can be seen, the long siphon 240 extends nearly all the way to the bottom of the mixing chamber 236, thereby allowing fluids to be delivered to the mixing chamber 236 and completely removed from the mixing chamber 236. The mixing chamber 236 also includes a short siphon 238 that may also be used to introduce fluids to the mixing chamber, if desired, but which may only be used to extract fluids above a predefined level from the mixing chamber, i.e., the short siphon 238 cannot be used to completely empty the mixing chamber 236 (the above discussion assumes that the mixing chamber is used in the orientation depicted with respect to the figure, with the ports located uppermost). The length of the short siphon 238 may be selected such that the end of the short siphon 238 is just above the level at which the THC adduct may be located after separation of the solvent, indicator, THC adduct, buffer, and sample has occurred. Since the amounts of each substance other than the THC adduct are generally known quantities, the length of the short siphon 238 can be set once for a given analysis protocol and then left alone.

Figure 35:
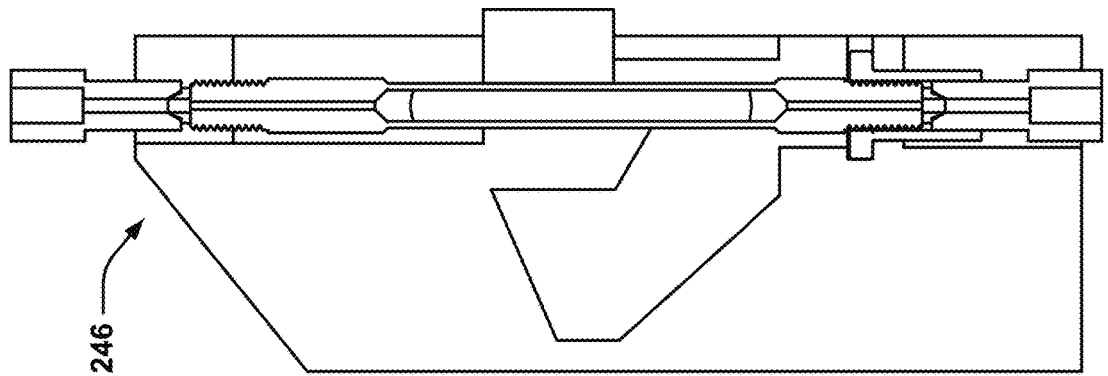
FIG. 35 depicts a section view of an optical measurement chamber.

FIG. 35 depicts a section view of the optical measurement chamber 246. The optical measurement chamber 246 may be provided, for example, by a cuvette or other optically clear vessel or passage that is suitable for exposing the samples contained within to excitation light and transmitting emitted light out for detection by the optical measurement sensor 252.

Figure 36:
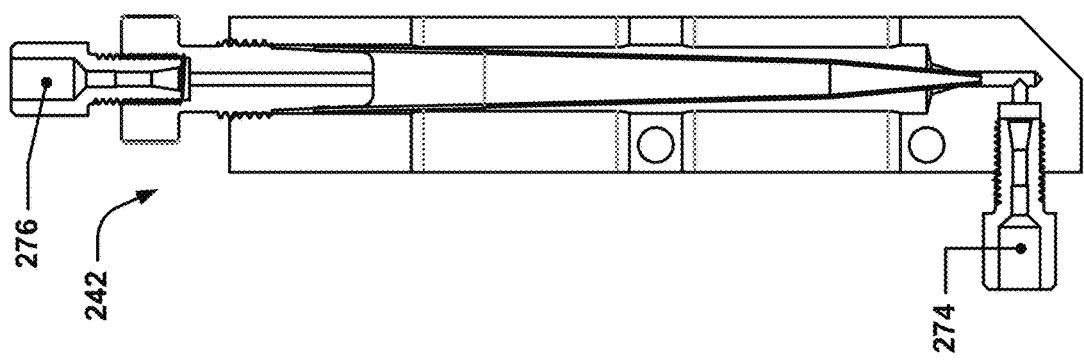
FIG. 36 depicts a section view of a first activation cell.

FIG. 36 depicts a section view of the first activation cell 242; the second activation cell 244 may be similar. The first activation cell 242, in this case, is a pipette that is held in a housing and that is interfaced with an activation cell fluid port 274 and an activation cell pneumatic port 276. The activation cell fluid port 274 may be connected to the fluid handling systems of the analysis system 200, whereas the activation cell pneumatic port 276 may be connected to a pneumatic system, e.g., such as an air pump 254 (which may, in turn, be connected with a muffler/filter 260, if desired). The air pump 254 may also be connectable with the pressurization port 272 of the mixing chamber, as well as other locations, similar to the implementation shown in FIG. 1.

Figure 37:
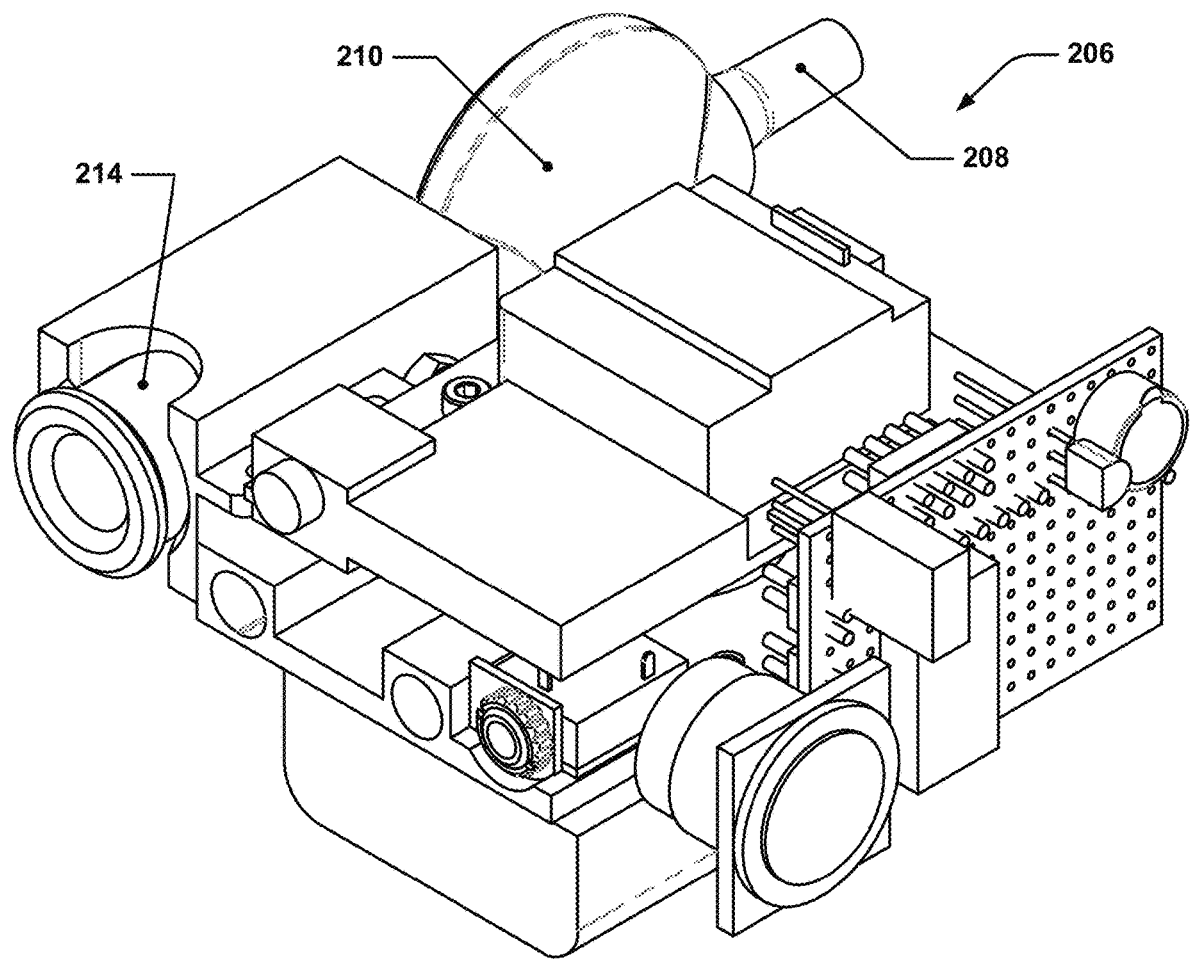
FIG. 37 depicts an example handheld breath collector module.

FIG. 37 depicts the handheld BCM (a prototype) 206. The handheld BCM 206 may include a saliva trap 210, such as may be used with alcohol breath-analyzer testing units. An example of a suitable saliva trap 210 is the ULTRAP II, described in U.S. Pat. No. 4,292,978, which is sold by Guth Laboratories, Inc. The handheld BCM 206 may also include a mouthpiece 208 (provided, in this case, by one end of the saliva trap 210), as well as catch media 214. Catch media 214 may include a porous media that has a high surface area to volume ratio, and may be as generally described in U.S. Patent Application No. 62/337,286. The handheld BCM 206 may also include on-board electronics 216 that may be configured to monitor how much breath has been breathed through the saliva trap 210 and catch media 214 via a pressure sensor (not shown, but see FIG. 1).

Figure 38:
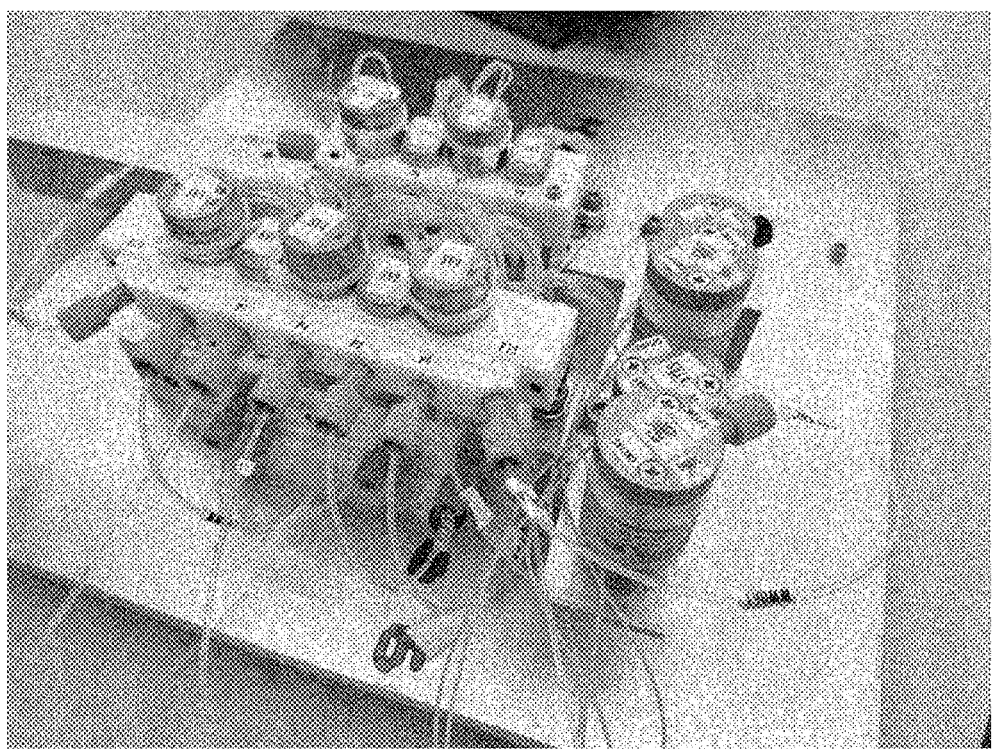
FIG. 38 is a photograph of a prototype cartridge during assembly; this view gives some idea of the nature of the tubing connections between the components.
Figure 39:
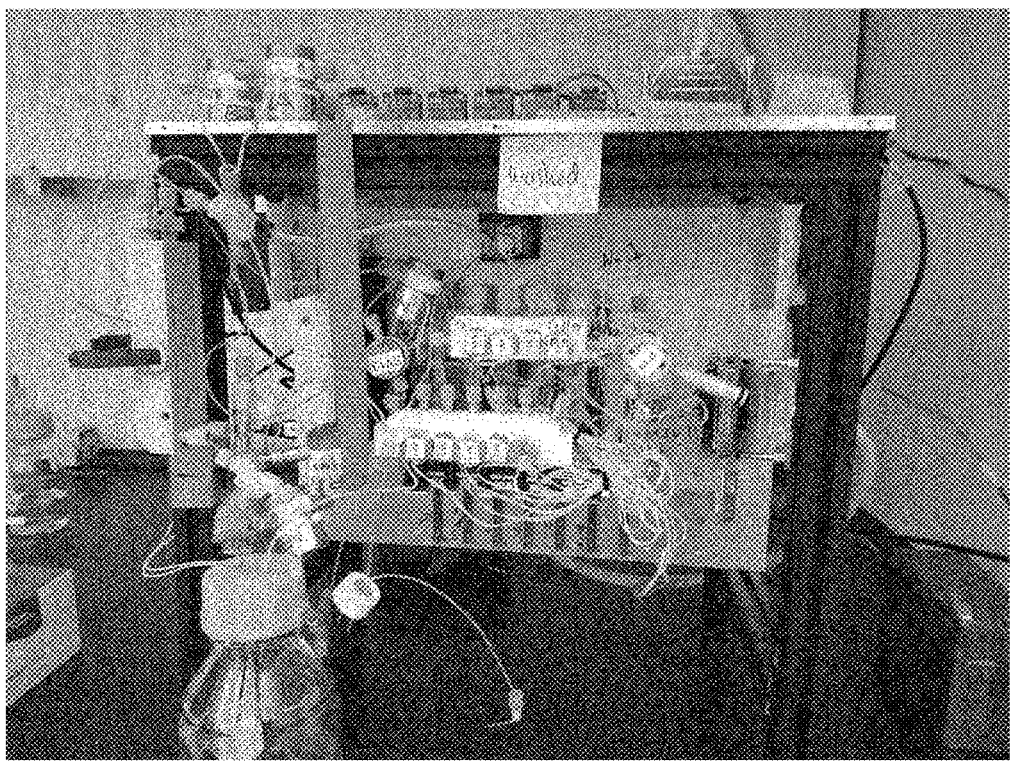
FIG. 39 is a photograph of a prototype cartridge mounted into a prototype base station.
Figure 40:
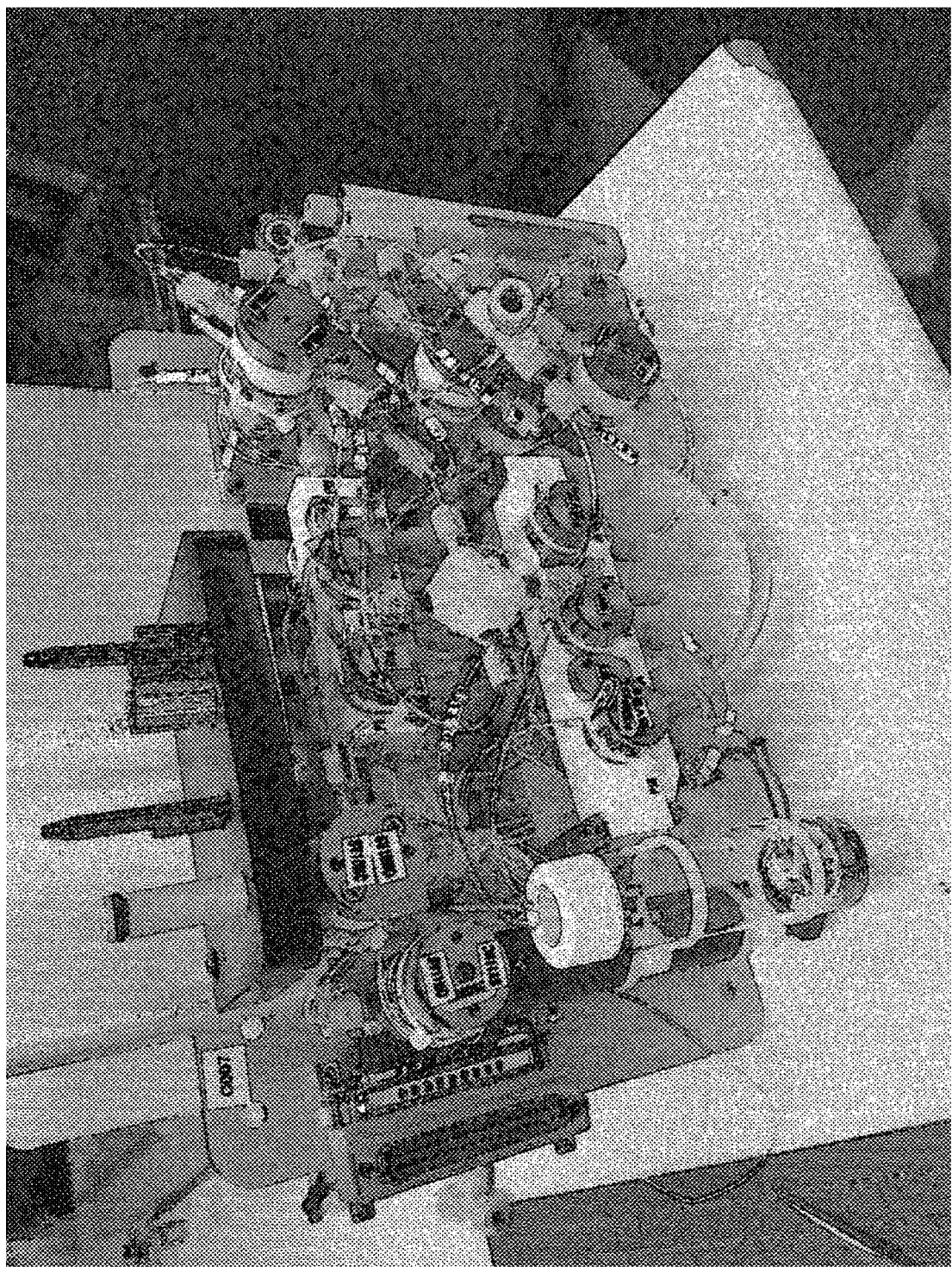
FIG. 40 is a photograph of another variant of a prototype cartridge with a layout similar to that in FIG. 26.
Figure 41:
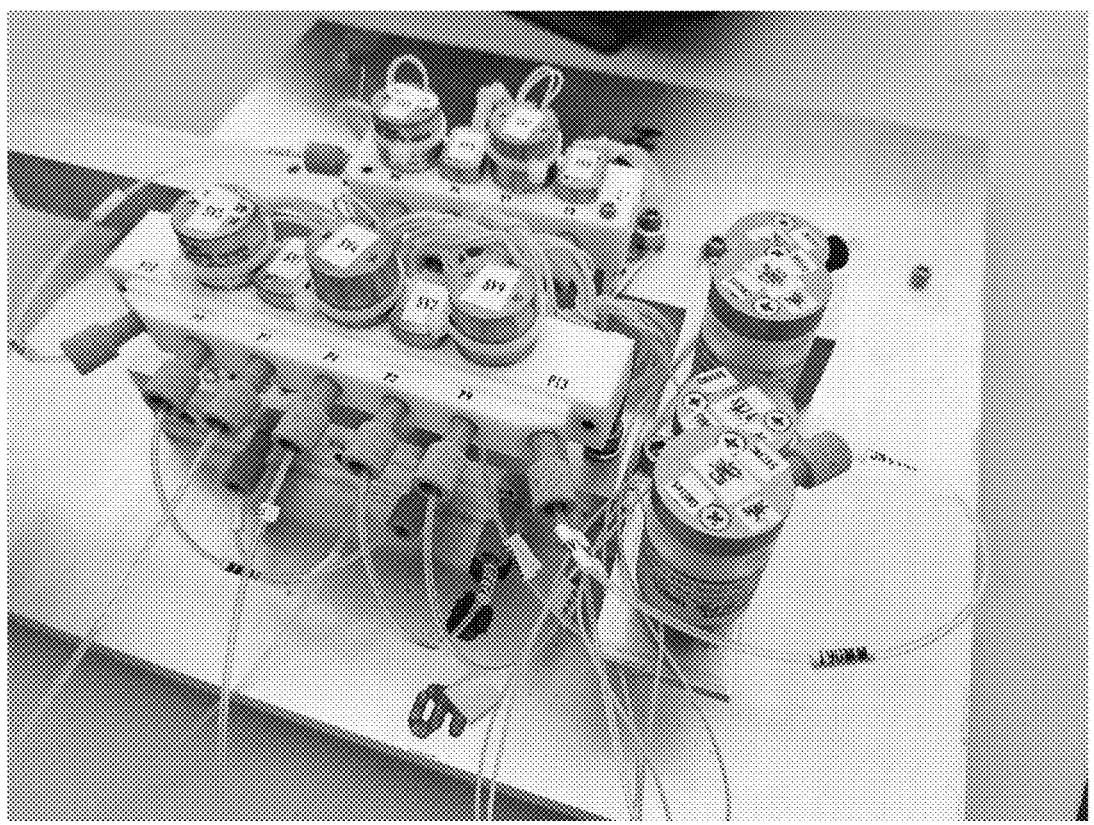
FIGS. 41 through 43 are color versions of FIGS. 38 through 40.
Figure 42:
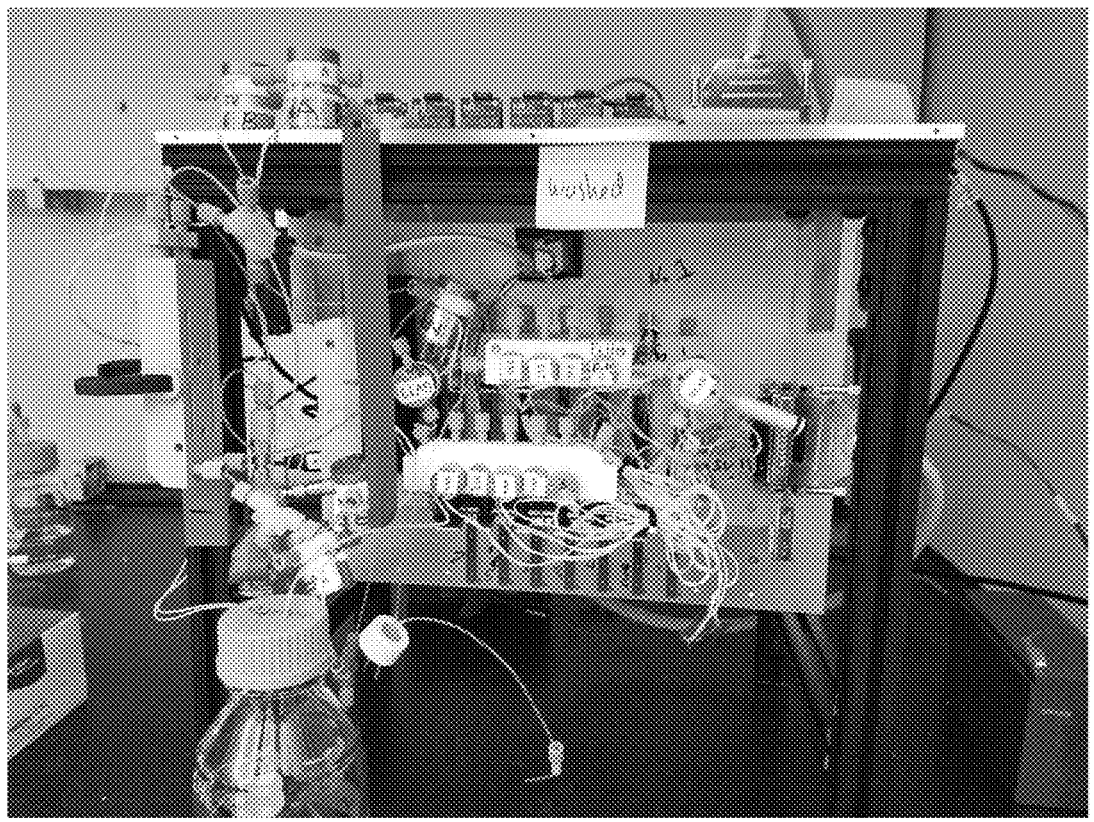
Figure 43:
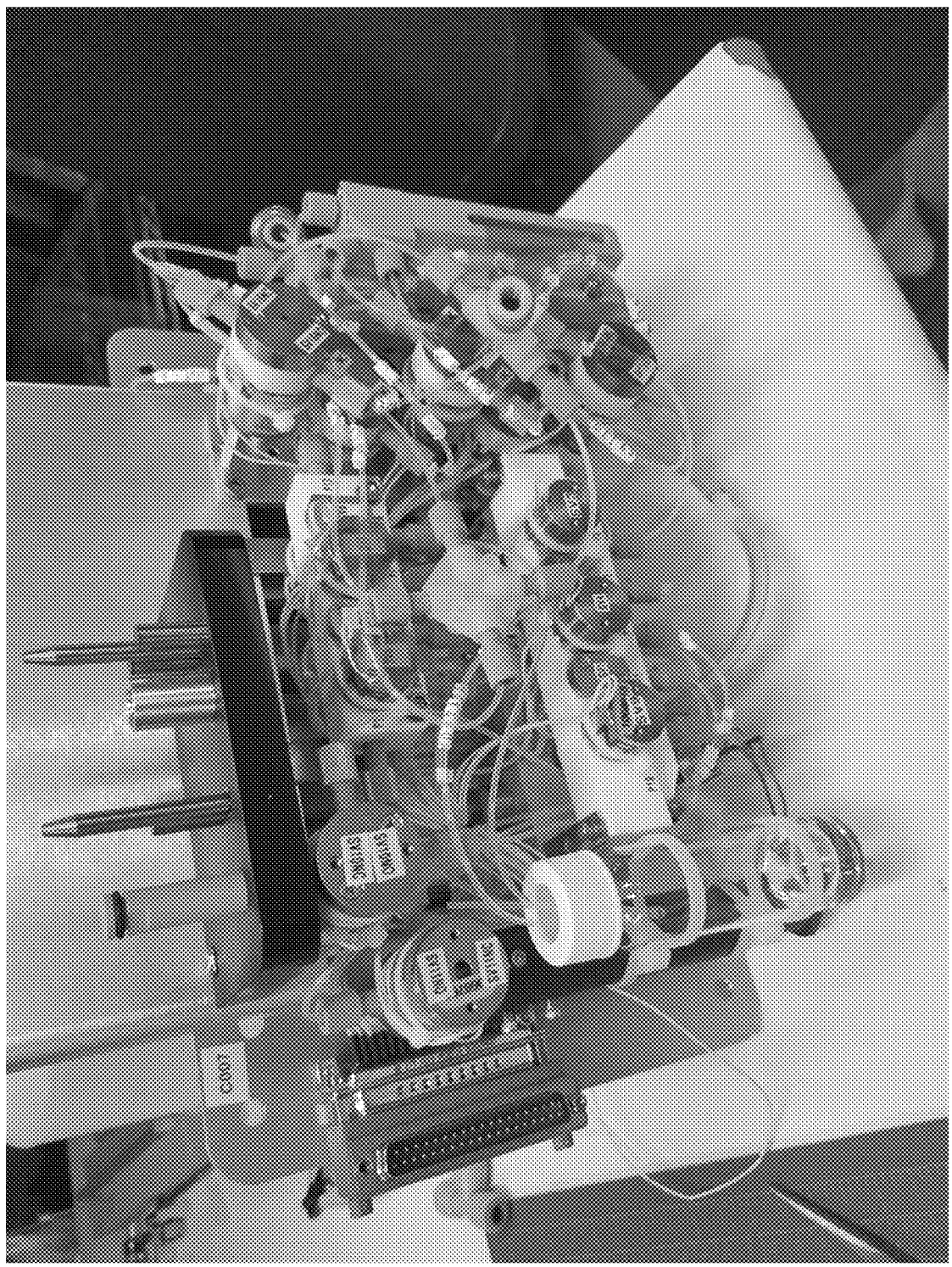

FIG. 38 is a photograph of a prototype cartridge during assembly; this view gives some idea of the nature of the tubing connections between the components. FIG. 39 is a photograph of a prototype cartridge mounted into a prototype base station.

The analysis system discussed herein may also include one or more processors, memory, and associated electronics to allow the one or more processors to control the valves, actuators, optical measurement sensor, air pump, and any other controllable elements of the analysis system in order to carry out the operations discussed herein. The memory may store computer-executable instructions for controlling the one or more processors to cause such operations to occur. It is to be understood that the present disclosure relates not only to system and apparatus implementations of the analysis system discussed herein, but also to techniques, methods, and processes for using such analysis systems, as well as to embodiments in which computer-executable instructions for controlling a processor or processors to cause such techniques to be practiced are stored on some form of computer-readable media, e.g., non-transitory, computer-readable media such as a hard disk, solid state drive, or non-volatile flash memory.

In some instances, the one or more processors and memory may include at least one processor and memory that are part of the BCM 106 and/or the cartridge 102 and/or the base station 104. In such cases, there may be processors and memory distributed between two or more of such components, and the components may communicate with one another, either through a wireless communications interface or a wired connection. In some implementations, one or more of the above components may also have a wireless communications interface, e.g., a cellular interface, that allows the one or more processors to wirelessly communicate information to a remote device, e.g., a server. For example, the BCM 106 may include a wireless interface that may transmit information relating to a sample, including, for example, metrics regarding the volume of exhaled breath, the time taken to obtain the sample, the time that the sample was obtained, the location where the sample was obtained (as either entered manually by a user or as obtained automatically, e.g., through use of a GPS receiver located in the BCM 106 or in another nearby piece of equipment, such as a paired smartphone or police car, and/or a picture of the subject providing the sample, e.g., as taken by a paired smartphone or by a camera that may be built in to the BCM 106. The same wireless communications interface, or a different wireless communications interface, may also communicate test results from the analysis system 100 to the same remote device in association with such information or in association with a record identifier linking such further information to previously transmitted information, allowing test results to be associated with a particular subject and sampling time/location.

In one embodiment consistent with the discussion provided above with respect to FIGS. 1 through 25 and FIGS. 27 through 38, the following quantities and compositions of chemicals may be used (the table below is with reference to the quantities and compositions present prior to analysis):

| Reservoir/Chamber | Composition | Amount |
|---|---|---|
| Sample | Ethanol (EtOH) | 250 µL |
| First Calibration Sample | EtOH + Buffer | 750 µL (250 µL EtOH + 500 µL Buffer) |
| Second Calibration Sample | EtOH + THC + Buffer | 750 µL (250 µL EtOH + 500 µL Buffer + THC) |
| Buffer | $NaHCO_3$ + $Na_2CO_3$ | 500 µL @ 20 mM $NaHCO_3$ and 13 mM $Na_2CO_3$ |
| Solvent | Methyl tertiary butyl ether (MTBE) + Heptane | 3000 µL (2250 µL Heptane + 750 µL MTBE) |
| Indicator Solvent | Hydrochloric acid (HCl, 100 µM concentration) | 1500 µL |
| Indicator Chamber | Rhodamine + camphorsulfonic acid + sodium nitrite | 1 mg |
| Cleaning Agent | Acetonitrile or EtOH | 7500 µL |

In such an embodiment, each of the three samples (the breath constituent sample and the two calibration samples) will be approximately 750 µL prior to the addition of the liquid indicator; the two calibration samples start out at approximately 750 µL (the second calibration sample may be slightly larger in volume due to the additional presence of THC, although this is a negligible contributor to overall volume in view of the other volumes used), and the sample volume may be brought up to 750 µL after the elution is completed and the buffer is added to the eluted sample. After the buffer has been added to each sample, if not already present, 250 µL of liquid indicator may be added to each sample, bringing the overall sample volumes each to 1000 µL. Each combined indicator and sample may then be combined/mixed with 1000 µL of solvent (MTBE+Heptane), and the mixture allowed to separate out. Once separation is complete (or sufficiently complete), approximately 650 µL of the topmost separation layer may be extracted, e.g., by the short siphon, from each sample, activated, if necessary, and then subjected to optical measurement to determine the amount of THC adduct that is present in each sample.

It is to be understood that the above-described system may be implemented in a number of different ways, and that such different implementations are also considered within the scope of this disclosure. For example, calibration samples are used in the example system to provide baseline measurements that may be used to calibrate the unknown sample THC adduct measurement against THC adduct measurements obtained from known quantities of THC. However, such calibration samples (and the equipment for processing them) may be omitted in some cases, e.g., if the accuracy of the THC measurement is not of particular concern (such may be the case where any non-zero amount of THC in a person's breath may be considered to be sufficient grounds for prosecution under a "driving under the influence" statute—the exact amount may be immaterial). Furthermore, the use of a mixing chamber may, in some instances, be optional. For example, mixing may occur in other chambers or vessels of the analysis system instead, such as in the optical measurement chamber—the mixture may be reciprocated in and out of the optical measurement chamber repeatedly, and then allowed to separate within the optical measurement chamber. The optical measurement sensor may, in such implementations, be positioned such that the optically sensitive area of the sensor is aligned with a region of the optical measurement chamber where the THC adduct is expected to separate into a layer, thereby allowing the amount of the THC adduct present to be quantified. In yet further or additional implementations, the activation cells that are used may be omitted and other systems or techniques for activating the fluorophores in the THC adduct may be used. For example, the solution containing the THC adduct may be subjected to a light source of a particular wavelength, an electrical charge, or some other stimulus in order to activate the fluorophore. In the example discussed earlier in this disclosure, the activation of the fluorophores in the THC adduct is achieved by passing the THC adduct into a particular brand and model of pipette that was found, via experimentation, to activate the THC adduct, and then removing the activated THC adduct from the pipette. It will be appreciated that the functionality of the calibration cell may be integrated into other components, such as the optical measurement chamber, thereby obviating the need for a separate activation cell (or cells). For example, if the THC adduct is an adduct that can be activated by passing an electrical charge through it, then electrodes may be placed so as to come into contact with the THC adduct to allow such a charge to be delivered. By way of further example, such electrodes may be placed in the optical measurement chamber so that the THC adduct may be activated within the optical measurement chamber; the optical measurement chamber, in this sense, may be viewed as both the optical measurement chamber and the activation cell. If the activation of the THC adduct involves re-usable components, such as non-consumable electrodes, then separate activation cells for each sample to be activated may be avoided as well, and a single, common activation cell may be used.

It is also to be recognized that the various connections between reservoirs and other components may be made, for example, by way of integrated flow paths in a block of material, e.g., flow paths that are machined or cast in a block of material, thereby eliminating some or all of the tubing connections that are depicted in the photographs. It is also to be understood that the system that is discussed may potentially be implemented on a smaller scale, and that the apparatus depicted in photographs is a test prototype that uses many off-the-shelf parts, such as valves, fittings, reservoirs, etc., and may be refined to be more compact. In such cases, the amounts of the reactants and fluids used may be adjusted to accommodate potentially smaller sample sizes and working volumes. Such refined versions of the apparatus are also considered to be within the scope of this disclosure.

What is claimed is:

1. A tetrahydrocannabinol (THC) detection system comprising:
    a plurality of components, the plurality of components including;
    one or more chambers to elute and retain a breath constituent sample;
    one or more indicator chambers containing an indicator;
    a buffer reservoir containing a basic buffer;
    a THC reservoir containing a non-zero amount of THC;
    one or more optical measurement chambers and one or more optical measurement sensors configured to obtain optical measurements from substances in the one or more optical measurement chambers;
    a plurality of valves that are configured to fluidly connect the plurality of components; and
    a controller configured to control the plurality of components connected by the plurality of valves to:
        (i) combine at least a first portion of the basic buffer with the breath constituent sample to form a sample buffer mixture;
        (ii) combine at least a first portion of the indicator with sample buffer mixture to cause a first sample composition to be formed with any THC that is present in the breath constituent sample;
        (iii) deliver a first sample composition mixture that includes the first sample composition and the basic buffer to the optical measurement chamber;
        (iv) combine at least a second portion of indicator with a first amount of THC in the THC reservoir and the basic buffer to form a second sample composition mixture that includes a second sample composition formed by the indicator and the first amount of THC in the THC reservoir; and
        (v) deliver the second sample composition to the one or more optical measurement chambers.

2. The THC detection system of claim 1, wherein the indicator comprises a diazotized fluorophore.

3. The THC detection system of claim 1, wherein the indicator comprises rhodamine.

4. The THC detection system of claim 2, wherein the indicator comprises rhodamine 123.

5. The THC detection system of claim 1, further comprising a waste reservoir, wherein the controller is configured to operate one or more of the plurality of valves to: permit at least the first sample composition present in the one or more optical measurement chambers to be delivered to the waste reservoir.

6. The THC detection system of claim 1, further comprising a cleaning agent reservoir containing a cleaning agent, wherein the controller is configured to operate one or more of the plurality of valves to: permit the cleaning agent to flow through the one or more optical measurement chambers.

7. The THC detection system of claim 1, wherein the controller is configured to:
    cause the one or more optical measurement sensors to obtain a first optical measurement from the one or more optical measurement chambers while the first sample composition and the second sample composition are in the one or more optical measurement chambers.

8. The THC detection system of claim 1, wherein the plurality of components and the plurality of valves are located in a common cartridge; and
    wherein the common cartridge is configured to be inserted into an analysis unit having the one or more optical measurement sensors configured to obtain luminescence readings from contents of the one or more optical measurement chamber.

9. The THC detection system of claim 8, further comprising the analysis unit, wherein: the analysis unit is configured to receive the common cartridge.

10. The THC detection system of claim 1, wherein the indicator includes a functionalized fluorophore.

11. The THC detection system of claim 10, wherein the functionalized fluorophore is a rhodamine.

12. The THC detection system of claim 11, wherein the functionalized fluorophore is rhodamine 123.

13. The THC detection system of claim 1, wherein the indicator is hydrochloric acid.

14. The THC detection system of claim 1, wherein the indicator is a diazo-functionalized reactant.

* * * * *